(12) United States Patent
Lin et al.

(10) Patent No.: US 10,039,846 B2
(45) Date of Patent: Aug. 7, 2018

(54) COMPOSITIONS TARGETING BRADYKININ RECEPTOR B1 FOR MEDICAL IMAGING OF CANCER AND OTHER DISORDERS

(71) Applicant: BRITISH COLUMBIA CANCER AGENCY BRANCH, Vancouver (CA)

(72) Inventors: Kuo-shyan Lin, Surrey (CA); Francois Benard, Vancouver (CA); Jinhe Pan, Vancouver (CA); Felix Mesak, Irvine, CA (US); Zhengxing Zhang, Vancouver (CA)

(73) Assignee: BRITISH COLUMBIA CANCER AGENCY BRANCH (CA)

( * ) Notice: Subject to any disclaimer, the term of this patent is extended or adjusted under 35 U.S.C. 154(b) by 0 days.

(21) Appl. No.: 14/428,249

(22) PCT Filed: Sep. 13, 2013

(86) PCT No.: PCT/CA2013/050707
§ 371 (c)(1),
(2) Date: Mar. 13, 2015

(87) PCT Pub. No.: WO2014/040192
PCT Pub. Date: Mar. 20, 2014

(65) Prior Publication Data
US 2015/0238641 A1    Aug. 27, 2015

Related U.S. Application Data

(60) Provisional application No. 61/700,804, filed on Sep. 13, 2012.

(51) Int. Cl.
| | |
|---|---|
| *A61K 31/435* | (2006.01) |
| *A61K 31/496* | (2006.01) |
| *A61K 31/498* | (2006.01) |
| *A61K 38/08* | (2006.01) |
| *A61K 51/08* | (2006.01) |
| *C07K 7/18* | (2006.01) |
| *C07D 241/50* | (2006.01) |
| *C07D 241/04* | (2006.01) |
| *C07D 403/04* | (2006.01) |
| *A61K 38/04* | (2006.01) |
| *C07D 403/12* | (2006.01) |
| *A61K 51/04* | (2006.01) |

(52) U.S. Cl.
CPC .......... *A61K 51/088* (2013.01); *A61K 31/435* (2013.01); *A61K 31/496* (2013.01); *A61K 31/498* (2013.01); *A61K 38/043* (2013.01); *A61K 51/0455* (2013.01); *A61K 51/0459* (2013.01); *C07D 241/04* (2013.01); *C07D 241/50* (2013.01); *C07D 403/04* (2013.01); *C07D 403/12* (2013.01); *C07K 7/18* (2013.01)

(58) Field of Classification Search
CPC .... A61K 38/043; A61K 51/08; A61K 51/088; A61K 31/435; A61K 31/496; A61K 31/498; C07D 241/04; C07D 241/50; C07D 241/403; C07D 241/12
See application file for complete search history.

(56) References Cited

U.S. PATENT DOCUMENTS

| | | | |
|---|---|---|---|
| 7,041,785 B1 | 5/2006 | Recoli et al. | |
| 7,989,417 B2 | 8/2011 | De Haen et al. | |
| 2002/0115693 A1 | 8/2002 | Rachwal et al. | |
| 2005/0020591 A1* | 1/2005 | Su ................ | A61K 31/498 514/234.2 |
| 2007/0269375 A1* | 11/2007 | Chen ................ | A61K 51/12 424/1.69 |
| 2008/0064642 A1 | 3/2008 | Guerin et al. | |
| 2010/0028912 A1* | 2/2010 | Linder ............. | A61K 51/08 435/7.21 |
| 2010/0234344 A1 | 9/2010 | Gibson et al. | |

FOREIGN PATENT DOCUMENTS

| | | |
|---|---|---|
| CN | 101920024 | 12/2010 |
| WO | 1998/007746 | 2/1998 |
| WO | 2003/007958 | 1/2003 |
| WO | 2009/090055 | 7/2009 |
| WO | 2011/141188 | 11/2011 |

OTHER PUBLICATIONS

Hall. Bradykinin Receptors. General Pharmacology. 1997, vol. 28, No. 1, pp. 1-6.*
Murone et al. Characterization and localization of bradykinin B2 receptors in the guinea-pig using a radioiodinated HOE140 analogue. European Journal of Pharmacology. 1996, vol. 306, pp. 237-247.*
Pan et al. Design, synthesis and evaluation of a gallium-68-labeled bradykinin derivative . . . 20th International Symposium on Radiopharmaceutical Sciences. Journal of Labelled Compounds and Radiopharmaceuticals. May 2013, vol. 56, Suppl. 1, p. S393, abstract No. P-306.*
Tousignant et al. Characterization of a novel binding site for 125l-Tyr-D-Arg-[Hyp3, D-Phe7, Leu8]bradykinin . . . European Journal of Pharmacology—Molecular Pharmacology Section. 1992, vol. 225, pp. 235-244.*
Barki-Harrington et al, "Bradykinin induced mitogenesis of androgen independent prostate cancer cells," Journal of Urology 2001, 165, 2121-2125.

(Continued)

*Primary Examiner* — Jeffrey E. Russel
(74) *Attorney, Agent, or Firm* — Stoel Rives LLP; Zhi-Xiang (Alex) Oh

(57) ABSTRACT

Bradykinin B1 receptor (B1R) targeting peptides and compounds are radiolabelled with radioisotopes that are suitable for imaging and/or radiotherapy. The radiolabelled peptides and compounds have utility in imaging tissues expressing or overexpressing B1R and/or treating diseases or conditions in which B1R is expressed or overexpressed, including cancer.

11 Claims, 9 Drawing Sheets

(56) References Cited

OTHER PUBLICATIONS

Barki-Harrington et al. "Requirement for direct cross-talk between B1 and B2 kinin receptors for the proliferation of androgen-insensitive prostate cancer PC3 cells," Biochemical Journal 2003, 371, 581-587.
Calixto et al, "Kinin B1 receptors: key G-protein-coupled receptors and their role in inflammatory and painful processes," British Journal of Pharmacology 2004, 143, 803-818.
Campos et al, "Non-peptide antagonists for kinin B1 receptors: new insights into their therapeutic potential for the management of inflammation and pain," TRENDS in Pharmacological Sciences 2006, 27, 646-651.
Chan et al, "Bradykinin antagonist dimer, CU201, inhibits the growth of human lung cancer cell lines by a "biased agonist" mechanism," Proceedings of the National Academy of Sciences of the United States of America 2002, 99, 4608-4613.
Chee et al., "Expression of tissue and plasma kallikreins and kinin B1 and B2 receptors in lung cancer" Biological Chemistry 2008, 389:1225-1233.
Cote et al, "Novel kinin B1 receptor agonists with improved pharmacological profiles," Peptides 2009, 30, 788-795.
Coussens et al, "Matrix Metalloproteinase Inhibitors and Cancer: Trials and Tribulations," Science 2002, 295, 2387-2392.
Drube et al, "In various tumour cell lines the peptide bradykinin B2 receptor antagonist, Hoe 140 (Icatibant), may act mitogenic agonist," British Journal of Pharmacology 2000, 131, 1553-1560.
Duroux-Richard et al., "Crosslinking Photosensitized by a Ruthenium Chelate as a Tool for Labeling and Topographical Studies of G-Protein-Coupled Receptors", Chemistry and Biology, Current Biology, London, GB, vol. 12, No. 1, Jan. 1, 2005 (Jan. 1, 2005), pp. 15-24.
Ehrenfeld et al, "Activation of kinin B1 receptor increases the release of metalloproteases-2 and -9 from both estrogen-sensitive and -insensitive breast cancer cells," Cancer Letters 2011; 301; 106-118.
Emanueli et al., "Local Delivery of Human Tissue Kallikrein Gene Accelerates Spontaneous Angiogenesis in Mouse Model of Hindlimb Ischemia," Circulation 2001, 103, 125-132.
Fernandes et al., "The bradykinin B1 receptor antagonist R-954 inhibits Ehrlich tumor growth in rodents," Peptides 2011, 32: 1849-1854.
Fuchs, K et al. "In vivo PET imaging of Bradykinin Receptor 1 (B1R) expression in a mouse model of chronic inflammation," Presentation No. T103, Scientific Session 9: Infection and Inflammation, 2011 World Molecular Imaging Congress held in San Diego, USA, Sep. 8, 2011 / 14:00-14:15 / Room: 32 http://www.wmis.org/abstracts/2011/start.htm.
Gera et al, "Structural modification of the highly potent peptide bradykinin B1 receptor antagonist B9958" International Immunopharmacology 2008, 8, 289-292.
Gera et al, "Amidin neighbouring-group effect on the stability of B9870, a highly potent anti-cancer bradykinin B1/B2 antagonist peptide dimer," Journal of Peptide Science 2010, 16, 118-119.
Gera et al., "N-terminal extended conjugates of the agonists and antagonists of both bradykinin receptor subtypes: Structure-activity relationship, cell imaging using ligands conjugated with fluorophores and prospect for functionally active cargoes," Peptides 2012; 34: 433-336.
Gohla et al, "Differential Involvement of Gα12 and Gα13 in Receptor-mediated Stress Fiber Formation" Journal of Biological Chemistry 1999, 274, 17901-17907.
Greco et al, "Bradykinin stimulates cell proliferation through an extracellular-regulated kinase 1 and 2-dependent mechanism in breast cancer cells in primary culture," Journal of Endocrinology 2005, 186, 291-301.
Heppeler et al, "Receptor Targeting for Tumor Localisation and Therapy with Radiopeptides" Current Medicinal Chemistry 2000, 7, 971-994.

Hsieh et al, "Intracellular signalings underlying bradykinin-induced matrix metalloproteinase-9 expression in rat brain astrocyte-1," Cellular Signalling 2004, 16, 1163-1176.
Kelly et al, "The G12 family of heterotrimeric G proteins promotes breast cancer invasion and metastasis," Proceedings of the National Academy of Sciences of the United States of America 2006, 103, 8173-8178.
Khan et al, "Targeted Tumor Diagnosis and Therapy with Peptide Hormones as Radiopharmaceuticals," Anti-Cancer Agents in Medicinal Chemistry 2008, 8, 186-199.
Kimura et al, "Localization of Bradykinin B2 Receptor in the Follicles of Porcine Ovary and Increased Expression of Matrix Metalloproteinase-3 and -20 in Cultured Granulosa Cells by Bradykinin Treatment1" Biology of Reproduction 2001, 65, 1462-1470.
Kuduk et al, "Bradykinin B1 Receptor Antagonists as Novel Analgesics: A Retrospective of Selected Medicinal Chemistry Developments" Current Topics in Medicinal Chemistry 2008, 8:1420-1430.
Leeb-Lundberg et al, "International Union of Pharmacology. XLV. Classification of the Kinin Receptor Family: from Molecular Mechanisms to Pathophysiological Consequences" Pharmacological Reviews 2005, 57:27-77.
Lu et al. "Bradykinin-Induced Cell Migration and COX-2 Production Mediated by the Bradykinin B1 Receptor in Glioma Cells," Journal of Cellular Biochemistry 2010, 110, 141-150.
Mankoff et al., "Tumor Receptor Imaging," Journal of Nuclear Medicine, 2008, 49:149S-163S.
McLean et al, "Kinin B receptors and the cardiovascular system: regulation of expression 1 and function" Cardiovascular Research, 2000, 48:194-210).
Meigs et al, "Gα12 and Gα13 Negatively Regulate the Adhesive Functions of Cadherin" Journal of Biological Chemistry 2002, 277, 24594-24600.
Molina et al., "Stimulation of the bradykinin B-1 receptor induces the proliferation of estrogen-sensitive breast cancer cells and activates the ERK1/2 signaling pathway" Breast Cancer Research and Treatment 2009, 118:499-510.
Raidoo et al, "Kinin receptors are expressed in human astrocytic tumour cells," Immunopharmacology 1999, 43:255-263.
Reubi et al, "Peptide Receptors as Molecular Targets for Cancer Diagnosis and Therapy" Endocrine Reviews 2003, 24, 389-427.
Searovic et al, "Effect of Tamoxifen and Retinoic Acid on Bradykinin Induced Proliferation in MCF-7 Cells" Journal of Cellular Biochemistry 2009, 106, 473-481.
Stewart et al, "Bradykinin Antagonists as Anti-Cancer Agents," Current Pharmaceutical Design 2003, 9, 2036-2042.
Stewart et al., "Bradykinin antagonists: discovery and development," Peptides 2004, 25, 527-532.
Taub et al., "Bradykinin Receptor Subtype 1 Expression and Function in Prostate Cancer," Cancer Research 2003, 63:2037-2041.
Velarde et al., "Mechanisms of MAPK activation by bradykinin in vascular smooth muscle cells," American Journal of Physiology 1999, 277, C253-61.
Virgolini et al, "Vasoactive Intestinal Peptide-Receptor Imaging for the Localization of Intentinal Adenocarcinomas and Endocrine Tumors," New England Journal of Medicine 1994, 331, 1116-1121.
Wu et al, "Identification of Bradykinin Receptors in Clinical Cancer Specimens and Murine Tumor Tissues" International Journal of Cancer 2002, 98:29-35).
Yang et al, "Bradykinin Enhances Cell Migration in Human Chondrosarcoma Cells Through BK Receptor Signaling Pathways" Journal of Cellular Biochemistry 2010, 109:82-92.
Zhernosekov et al, "Processing of Generator-Produced 68Ga for Medical Application" J Nucl Med 2007, 48:1741-1748.
International Search Report for International Application No. PCT/CA2013/050707 dated Dec. 13, 2013.
Extended European Search Report for European Patent Application No. 13836701.6 dated Jun. 14, 2016.
Office Action for Chinese Patent Application No. 201380059035.6 dated Aug. 19, 2016.
Bawolak et al., "Fluorescent ligands of the bradykinin B1 receptors: Pharmacologic characterization and application to the study of

(56) References Cited

OTHER PUBLICATIONS agonist-induced receptor translocation and cell surface receptor expression." J. Pharmacol. and Exp. Therap. 2009. 329(1), pp. 159-168.
Chen et al., "Discovery of dihydroquinoxalinone acetamides containing bicyclic amines as potent Bradykinin B1 receptor antagonists." Bioorg. Med. Chem. Lett. 2008. 18, pp. 4477-4481.
Dziadulewicz et al., "Non-petide ligands for bradykinin receptors 1995-2004." Expert Opin. Ther. Patents. 2005, 1597), pp. 829-859.
Huang et al., "Bradykinin B1 receptor antagonists as potential therapeutic agents for pain." J. Med. Chem. 2010. 53, pp. 5383-5399.
Levesque et al., "Development of a binding assay for the B1 receptors for kinins." Immunopharmacology. 1995. 29, pp. 141-147.
Ransom et al., "Pharmacological characterization and radioligand binding properties of a high-affinity, nonpeptide, bradykinin B1 receptor antagonist." Eur. J. Pharmacol. 2004. 499, pp. 77-84.
Su et al., "Discovery of a potent, non-peptide bradykinin B1 receptor antagonist." J. Am. Chem. Soc., 2003. 125, pp. 7516-7517.
Talbot et al., "Cellular localization of kinin B receptor in the spinal cord of streptozotocin-diabetic rats with a fluorescent [Na-Biodipy]-des-Arg9-bradykinin." J. Neuroinflammation. 2009. 6, p. 11.
Yasujima et al., "Bradykinin receptors in rat uterine smooth muscle: Studies using radiolabeled ligand binding." Tohoku J. Exp. Med. 1984. 144, pp. 107-177.
Chinese Office Action dated Jun. 14, 2017 for CN application 201380059035.6.
European Office Action dated Nov. 24, 2017 for EP Application 13836701.6.

\* cited by examiner

A.

B.

HEK293T::GFP::(hBDKRB1, Blasticidin[R]-RFP)

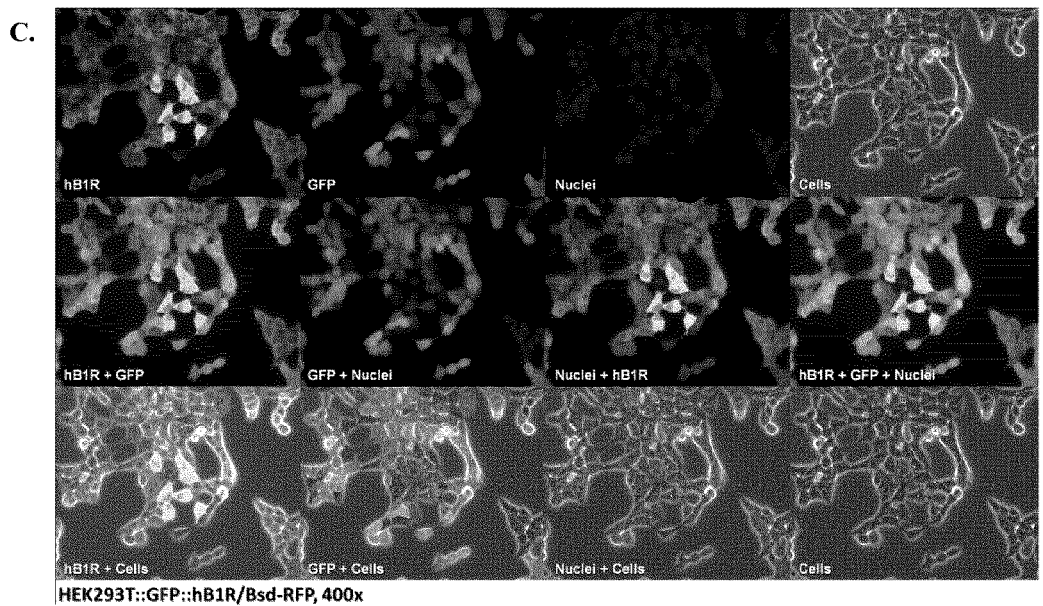
FIG. 2 (con.)

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial sequence
<220> FEATURE:
<223> OTHER INFORMATION: [Leu8]-des-Arg9-BK

<400> SEQUENCE: 1

Arg Pro Pro Gly Phe Ser Pro Leu
1               5

<210> SEQ ID NO 2
<211> LENGTH: 9
<212> TYPE: PRT
<213> ORGANISM: Artificial sequence
<220> FEATURE:
<223> OTHER INFORMATION: Lys[Leu8]-des-Arg9-BK

<400> SEQUENCE: 2

Lys Arg Pro Pro Gly Phe Ser Pro Leu
```

```
1               5

<210> SEQ ID NO 3
<211> LENGTH: 8
<212> TYPE: PRT
<213> ORGANISM: Artificial sequence
<220> FEATURE:
<223> OTHER INFORMATION: [des-Arg9]-BK

<400> SEQUENCE: 3

Arg Pro Pro Gly Phe Ser Pro Phe
1               5

<210> SEQ ID NO 4
<211> LENGTH: 9
<212> TYPE: PRT
<213> ORGANISM: Artificial sequence
<220> FEATURE:
<223> OTHER INFORMATION: [des-Arg10]-kallidin

<400> SEQUENCE: 4

Lys Arg Pro Pro Gly Phe Ser Pro Phe
1               5

<210> SEQ ID NO 5
<211> LENGTH: 9
<212> TYPE: PRT
<213> ORGANISM: Human
<220> FEATURE:
<221> NAME/KEY: MISC_FEATURE
<223> OTHER INFORMATION: bradykinin

<400> SEQUENCE: 5

Arg Pro Pro Gly Phe Ser Pro Phe Arg
1               5

<210> SEQ ID NO 6
<211> LENGTH: 10
<212> TYPE: PRT
<213> ORGANISM: Human
<220> FEATURE:
<221> NAME/KEY: MISC_FEATURE
<223> OTHER INFORMATION: kallidin

<400> SEQUENCE: 6

Lys Arg Pro Pro Gly Phe Ser Pro Phe Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Peptidic compound
<220> FEATURE:
<221> NAME/KEY: MOD_RES
<222> LOCATION: (1)..(1)
<223> OTHER INFORMATION: X is absent, Lys or D-Arg
<220> FEATURE:
<221> NAME/KEY: MOD_RES
<222> LOCATION: (4)..(4)
<223> OTHER INFORMATION: X is Pro or Hyp
<220> FEATURE:
<221> NAME/KEY: MOD_RES
<222> LOCATION: (6)..(6)
<223> OTHER INFORMATION: X is Phe, Cha, Thi, (alpha-Me)Phe, Igl or Cpg
<220> FEATURE:
<221> NAME/KEY: MOD_RES
<222> LOCATION: (8)..(8)
<223> OTHER INFORMATION: X is Pro, D-Tic, D-Hyp, D-beta-Nal or D-Igl
```

```
<220> FEATURE:
<221> NAME/KEY: MOD_RES
<222> LOCATION: (9)..(9)
<223> OTHER INFORMATION: X is Leu, Ile, D-Phe, Cpg or Oic

<400> SEQUENCE: 7

Xaa Arg Pro Xaa Gly Xaa Ser Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: B1R targeting compound
<220> FEATURE:
<221> NAME/KEY: MOD_RES
<222> LOCATION: (1)..(1)
<223> OTHER INFORMATION: Absent, Lys or D-Arg
<220> FEATURE:
<221> NAME/KEY: MOD_RES
<222> LOCATION: (4)..(4)
<223> OTHER INFORMATION: Pro or Hyp
<220> FEATURE:
<221> NAME/KEY: MOD_RES
<222> LOCATION: (6)..(6)
<223> OTHER INFORMATION: Phe, Cha, Thi, (alpha-Me)Phe, Igl or Cpg
<220> FEATURE:
<221> NAME/KEY: MOD_RES
<222> LOCATION: (8)..(8)
<223> OTHER INFORMATION: X is Pro, D-Tic, D-Hyp, D-beta Nal or D-Igl
<220> FEATURE:
<221> NAME/KEY: MOD_RES
<222> LOCATION: (9)..(9)
<223> OTHER INFORMATION: X is Leu, Ile, D-Phe, Cpg or Oic

<400> SEQUENCE: 8

Xaa Arg Pro Xaa Gly Xaa Ser Xaa Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: B1R targeting compound
<220> FEATURE:
<221> NAME/KEY: MOD_RES
<222> LOCATION: (1)..(1)
<223> OTHER INFORMATION: X is absent, Lys or D-Arg
<220> FEATURE:
<221> NAME/KEY: MOD_RES
<222> LOCATION: (4)..(4)
<223> OTHER INFORMATION: X is Pro or Hyp
<220> FEATURE:
<221> NAME/KEY: MOD_RES
<222> LOCATION: (6)..(6)
<223> OTHER INFORMATION: X is Phe, Cha, Thi, (alpha-Me)Phe, Igl or Cpg
<220> FEATURE:
<221> NAME/KEY: MOD_RES
<222> LOCATION: (8)..(8)
<223> OTHER INFORMATION: X is Pro, D-Tic, D-Hyp, D-beta Nal or D-Igl
<220> FEATURE:
<221> NAME/KEY: MOD_RES
<222> LOCATION: (9)..(9)
<223> OTHER INFORMATION: X is Leu, Ile, D-Phe, Cpg or Oic

<400> SEQUENCE: 9

Xaa Arg Pro Xaa Gly Xaa Ser Xaa Xaa
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (4)..(4)
<223> OTHER INFORMATION: X is Hyp
<220> FEATURE:
<221> NAME/KEY: MOD_RES
<222> LOCATION: (6)..(6)
<223> OTHER INFORMATION: X is Cha

<400> SEQUENCE: 10

Lys Arg Pro Xaa Gly Xaa Ser Pro Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (1)..(1)
<223> OTHER INFORMATION: Xaa is D-Arg
<220> FEATURE:
<221> NAME/KEY: MOD_RES
<222> LOCATION: (4)..(4)
<223> OTHER INFORMATION: Xaa is Hyp
<220> FEATURE:
<221> NAME/KEY: MOD_RES
<222> LOCATION: (6)..(6)
<223> OTHER INFORMATION: Xaa is Thi
<220> FEATURE:
<221> NAME/KEY: MOD_RES
<222> LOCATION: (8)..(8)
<223> OTHER INFORMATION: Xaa is D-Tic
<220> FEATURE:
<221> NAME/KEY: MOD_RES
<222> LOCATION: (9)..(9)
<223> OTHER INFORMATION: Xaa is Oic

<400> SEQUENCE: 11

Xaa Arg Pro Xaa Gly Xaa Ser Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (1)..(1)
<223> OTHER INFORMATION: Xaa is D-Arg
<220> FEATURE:
<221> NAME/KEY: MOD_RES
<222> LOCATION: (4)..(4)
<223> OTHER INFORMATION: Xaa is Hyp
<220> FEATURE:
<221> NAME/KEY: MOD_RES
<222> LOCATION: (8)..(8)
<223> OTHER INFORMATION: Xaa is D-Hyp
<220> FEATURE:
<221> NAME/KEY: MOD_RES
<222> LOCATION: (9)..(9)
<223> OTHER INFORMATION: Xaa is (transpropyl-Oic)

<400> SEQUENCE: 12

Xaa Arg Pro Xaa Gly Phe Ser Xaa Xaa
1               5
```

<210> SEQ ID NO 13
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (8)..(8)
<223> OTHER INFORMATION: X is D-beta-Nal

<400> SEQUENCE: 13

Lys Arg Pro Pro Gly Phe Ser Xaa Ile
1               5

<210> SEQ ID NO 14
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (6)..(6)
<223> OTHER INFORMATION: X is (alpha-Me)Phe
<220> FEATURE:
<221> NAME/KEY: MOD_RES
<222> LOCATION: (8)..(8)
<223> OTHER INFORMATION: X is D-beta-Nal

<400> SEQUENCE: 14

Lys Arg Pro Pro Gly Xaa Ser Xaa Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (1)..(1)
<223> OTHER INFORMATION: Xaa is N-acetyl Orn
<220> FEATURE:
<221> NAME/KEY: MOD_RES
<222> LOCATION: (3)..(3)
<223> OTHER INFORMATION: Xaa is Oic
<220> FEATURE:
<221> NAME/KEY: MOD_RES
<222> LOCATION: (6)..(6)
<223> OTHER INFORMATION: Xaa is (alpha-Me)Phe
<220> FEATURE:
<221> NAME/KEY: MOD_RES
<222> LOCATION: (8)..(8)
<223> OTHER INFORMATION: Xaa is D-beta Nal

<400> SEQUENCE: 15

Xaa Arg Xaa Pro Gly Xaa Ser Xaa Ile
1               5

<210> SEQ ID NO 16
<211> LENGTH: 10
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (5)..(5)
<223> OTHER INFORMATION: X is Hyp

```
<220> FEATURE:
<221> NAME/KEY: MOD_RES
<222> LOCATION: (7)..(7)
<223> OTHER INFORMATION: X is Igl
<220> FEATURE:
<221> NAME/KEY: MOD_RES
<222> LOCATION: (9)..(9)
<223> OTHER INFORMATION: X is D-Igl

<400> SEQUENCE: 16

Lys Lys Arg Pro Xaa Gly Xaa Ser Xaa Ile
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (5)..(5)
<223> OTHER INFORMATION: X is Hyp
<220> FEATURE:
<221> NAME/KEY: MOD_RES
<222> LOCATION: (7)..(7)
<223> OTHER INFORMATION: X is Cpg
<220> FEATURE:
<221> NAME/KEY: MOD_RES
<222> LOCATION: (9)..(9)
<223> OTHER INFORMATION: X is D-Tic
<220> FEATURE:
<221> NAME/KEY: MOD_RES
<222> LOCATION: (10)..(10)
<223> OTHER INFORMATION: X is Cpg

<400> SEQUENCE: 17

Lys Lys Arg Pro Xaa Gly Xaa Ser Xaa Xaa
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Peptidic B1R Antagonists
<220> FEATURE:
<221> NAME/KEY: MOD_RES
<222> LOCATION: (1)..(1)
<223> OTHER INFORMATION: Xaa is Sar
<220> FEATURE:
<221> NAME/KEY: MOD_RES
<222> LOCATION: (9)..(9)
<223> OTHER INFORMATION: Xaa is D-Phe

<400> SEQUENCE: 18

Xaa Arg Pro Pro Gly Phe Ser Pro Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Peptidic B1R Agonists
<220> FEATURE:
<221> NAME/KEY: MOD_RES
<222> LOCATION: (4)..(4)
<223> OTHER INFORMATION: X is Hyp
<220> FEATURE:
<221> NAME/KEY: MOD_RES
<222> LOCATION: (6)..(6)
<223> OTHER INFORMATION: X is Cha
```

```
<220> FEATURE:
<221> NAME/KEY: MOD_RES
<222> LOCATION: (9)..(9)
<223> OTHER INFORMATION: X is D-Phe

<400> SEQUENCE: 19

Lys Arg Pro Xaa Gly Xaa Ser Pro Xaa
1               5

<210> SEQ ID NO 20
<211> LENGTH: 10
<212> TYPE: PRT
<213> ORGANISM: Artificial Sequence
<220> FEATURE:
<223> OTHER INFORMATION: Peptidic B1R Agonists
<220> FEATURE:
<221> NAME/KEY: MOD_RES
<222> LOCATION: (1)..(1)
<223> OTHER INFORMATION: Xaa is Sar
<220> FEATURE:
<221> NAME/KEY: MOD_RES
<222> LOCATION: (5)..(5)
<223> OTHER INFORMATION: Xaa is Hyp
<220> FEATURE:
<221> NAME/KEY: MOD_RES
<222> LOCATION: (7)..(7)
<223> OTHER INFORMATION: Xaa is Cha
<220> FEATURE:
<221> NAME/KEY: MOD_RES
<222> LOCATION: (10)..(10)
<223> OTHER INFORMATION: Xaa is D-Phe

<400> SEQUENCE: 20

Xaa Lys Arg Pro Xaa Gly Xaa Ser Pro Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptidic B1R Agonists
<220> FEATURE:
<221> NAME/KEY: MOD_RES
<222> LOCATION: (1)..(1)
<223> OTHER INFORMATION: Xaa is Sar
<220> FEATURE:
<221> NAME/KEY: MOD_RES
<222> LOCATION: (5)..(5)
<223> OTHER INFORMATION: Xaa is Hyp
<220> FEATURE:
<221> NAME/KEY: MOD_RES
<222> LOCATION: (7)..(7)
<223> OTHER INFORMATION: Xaa is Igl
<220> FEATURE:
<221> NAME/KEY: MOD_RES
<222> LOCATION: (10)..(10)
<223> OTHER INFORMATION: Xaa is D-Phe

<400> SEQUENCE: 21

Xaa Lys Arg Pro Xaa Gly Xaa Ser Pro Xaa
1               5                   10

<210> SEQ ID NO 22

<400> SEQUENCE: 22

000

<210> SEQ ID NO 23
<211> LENGTH: 10
<212> TYPE: PRT
```

```
<213> ORGANISM: Artificial Sequence
<220> FEATURE:
<223> OTHER INFORMATION: B1R targeting moiety
<220> FEATURE:
<221> NAME/KEY: MOD_RES
<222> LOCATION: (1)..(1)
<223> OTHER INFORMATION: Xaa is absent, Lys or Sar
<220> FEATURE:
<221> NAME/KEY: MOD_RES
<222> LOCATION: (2)..(2)
<223> OTHER INFORMATION: Xaa is absent, Lys, Sar or D-Arg
<220> FEATURE:
<221> NAME/KEY: MOD_RES
<222> LOCATION: (5)..(5)
<223> OTHER INFORMATION: Xaa is Pro or Hyp
<220> FEATURE:
<221> NAME/KEY: MOD_RES
<222> LOCATION: (7)..(7)
<223> OTHER INFORMATION: Xaa is Phe, Cha, Thi, (alpha-Me)Phe, Igl or Cpg
<220> FEATURE:
<221> NAME/KEY: MOD_RES
<222> LOCATION: (9)..(9)
<223> OTHER INFORMATION: Xaa is Pro, D-Tic, D-Hyp, D-beta Nal or D-Igl
<220> FEATURE:
<221> NAME/KEY: MOD_RES
<222> LOCATION: (10)..(10)
<223> OTHER INFORMATION: Xaa is Leu, Ile, D-Phe, Cpg or Oic

<400> SEQUENCE: 23

Xaa Xaa Arg Pro Xaa Gly Xaa Ser Xaa Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: B1R targeting moiety
<220> FEATURE:
<221> NAME/KEY: MOD_RES
<222> LOCATION: (1)..(1)
<223> OTHER INFORMATION: Xaa is absent or Sar
<220> FEATURE:
<221> NAME/KEY: MOD_RES
<222> LOCATION: (2)..(2)
<223> OTHER INFORMATION: Xaa is Lys
<220> FEATURE:
<221> NAME/KEY: MOD_RES
<222> LOCATION: (5)..(5)
<223> OTHER INFORMATION: Xaa is Pro or Hyp
<220> FEATURE:
<221> NAME/KEY: MOD_RES
<222> LOCATION: (7)..(7)
<223> OTHER INFORMATION: Xaa is Phe, Cha or Cpg
<220> FEATURE:
<221> NAME/KEY: MOD_RES
<222> LOCATION: (9)..(9)
<223> OTHER INFORMATION: Xaa is Pro
<220> FEATURE:
<221> NAME/KEY: MOD_RES
<222> LOCATION: (10)..(10)
<223> OTHER INFORMATION: Xaa is Leu, Ile or D-Phe

<400> SEQUENCE: 24

Xaa Xaa Arg Pro Xaa Gly Xaa Ser Xaa Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: B1R targeting moiety
<220> FEATURE:
<221> NAME/KEY: MOD_RES
```

```
<222> LOCATION: (1)..(1)
<223> OTHER INFORMATION: X is absent
<220> FEATURE:
<221> NAME/KEY: MOD_RES
<222> LOCATION: (2)..(2)
<223> OTHER INFORMATION: X is Lys
<220> FEATURE:
<221> NAME/KEY: MOD_RES
<222> LOCATION: (5)..(5)
<223> OTHER INFORMATION: X is Pro or Hyp
<220> FEATURE:
<221> NAME/KEY: MOD_RES
<222> LOCATION: (7)..(7)
<223> OTHER INFORMATION: X is Phe or Cha
<220> FEATURE:
<221> NAME/KEY: MOD_RES
<222> LOCATION: (9)..(9)
<223> OTHER INFORMATION: X is Pro
<220> FEATURE:
<221> NAME/KEY: MOD_RES
<222> LOCATION: (10)..(10)
<223> OTHER INFORMATION: X is Leu or D-Phe

<400> SEQUENCE: 25

Xaa Xaa Arg Pro Xaa Gly Xaa Ser Xaa Xaa
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Peptidic B1R targeting comp

```
<223> OTHER INFORMATION: X is Phe, Cha, or Cpg
<220> FEATURE:
<221> NAME/KEY: MOD_RES
<222> LOCATION: (8)..(8)
<223> OTHER INFORMATION: X is Pro
<220> FEATURE:
<221> NAME/KEY: MOD_RES
<222> LOCATION: (9)..(9)
<223> OTHER INFORMATION: X is Leu, Ile or D-Phe

<400> SEQUENCE: 27

Xaa Arg Pro Xaa Gly Xaa Ser Xaa Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is Lys
<220> FEATURE:
<221> NAME/KEY: MOD_RES
<222> LOCATION: (4)..(4)
<223> OTHER INFORMATION: X is Pro or Hyp
<220> FEATURE:
<221> NAME/KEY: MOD_RES
<222> LOCATION: (6)..(6)
<223> OTHER INFORMATION: X is Phe or Cha;
<220> FEATURE:
<221> NAME/KEY: MOD_RES
<222> LOCATION: (8)..(8)
<223> OTHER INFORMATION: X is Pro
<220> FEATURE:
<221> NAME/KEY: MOD_RES
<222> LOCATION: (9)..(9)
<223> OTHER INFORMATION: X is Leu or D-Phe

<400> SEQUENCE: 28

Xaa Arg Pro Xaa Gly Xaa Ser Xaa Xaa
1               5

<210> SEQ ID NO 29
<211> LENGTH: 11
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (6)..(6)
<223> OTHER INFORMATION: X is Hyp
<220> FEATURE:
<221> NAME/KEY: MOD_RES
<222> LOCATION: (8)..(8)
<223> OTHER INFORMATION: X is Cha

<400> SEQUENCE: 29

Gly Gly Lys Arg Pro Xaa Gly Xaa Ser Pro Leu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: B1R targeting compound
<220> FEATURE:
<221> NAME/KEY: MOD_RES
<222> LOCATION: (6)..(6)
```

```
<223> OTHER INFORMATION: X is Hyp
<220> FEATURE:
<221> NAME/KEY: MOD_RES
<222> LOCATION: (8)..(8)
<223> OTHER INFORMATION: X is Cha
<220> FEATURE:
<221> NAME/KEY: MOD_RES
<222> LOCATION: (11)..(11)
<223> OTHER INFORMATION: X is D-Phe

<400> SEQUENCE: 30

Gly Gly Lys Arg Pro Xaa Gly Xaa Ser Pro Xaa
1               5                   10

<210> SEQ ID NO 31
<211> LENGTH: 10
<212> TYPE: PRT
<213> ORGANISM: Artificial Sequence
<220> FEATURE:
<223> OTHER INFORMATION: B1R targeting moiety
<220> FEATURE:
<221> NAME/KEY: MOD_RES
<222> LOCATION: (1)..(1)
<223> OTHER INFORMATION: X is Lys or Sar
<220> FEATURE:
<221> NAME/KEY: MOD_RES
<222> LOCATION: (2)..(2)
<223> OTHER INFORMATION: X is Lys or D-Arg
<220> FEATURE:
<221> NAME/KEY: MOD_RES
<222> LOCATION: (5)..(5)
<223> OTHER INFORMATION: X is Pro or Hyp
<220> FEATURE:
<221> NAME/KEY: MOD_RES
<222> LOCATION: (7)..(7)
<223> OTHER INFORMATION: X is Phe, Cha, Thi, (alpha-Me)Phe, Igl or Cpg
<220> FEATURE:
<221> NAME/KEY: MOD_RES
<222> LOCATION: (9)..(9)
<223> OTHER INFORMATION: X is Pro, D-Tic, D-Hyp, D-betaNal or D-Igl
<220> FEATURE:
<221> NAME/KEY: MOD_RES
<222> LOCATION: (10)..(10)
<223> OTHER INFORMATION: X is Leu, Ile, D-Phe, Cpg or Oic

<400> SEQUENCE: 31

Xaa Xaa Arg Pro Xaa Gly Xaa Ser Xaa Xaa
1               5                   10

<210> SEQ ID NO 32
<211> LENGTH: 4
<212> TYPE: PRT
<213> ORGANISM: artificial sequence
<220> FEATURE:
<223> OTHER INFORMATION: linker peptide

<400> SEQUENCE: 32

Arg Arg Arg Arg
1

<210> SEQ ID NO 33
<211> LENGTH: 11
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is D-Pra
<220> FEATURE:
<221> NAME/KEY: MOD_RES
<222> LOCATION: (2)..(2)
```

```
<223> OTHER INFORMATION: X is Ahx
<220> FEATURE:
<221> NAME/KEY: MOD_RES
<222> LOCATION: (6)..(6)
<223> OTHER INFORMATION: X is Hyp
<220> FEATURE:
<221> NAME/KEY: MOD_RES
<222> LOCATION: (8)..(8)
<223> OTHER INFORMATION: X is Cha
<220> FEATURE:
<221> NAME/KEY: MOD_RES
<222> LOCATION: (11)..(11)
<223> OTHER INFORMATION: X is D-Phe

<400> SEQUENCE: 33

Xaa Xaa Lys Arg Pro Xaa Gly Xaa Ser Pro Xaa
1               5                   10

<210> SEQ ID NO 34
<211> LENGTH: 10
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is Ahx
<220> FEATURE:
<221> NAME/KEY: MOD_RES
<222> LOCATION: (5)..(5)
<223> OTHER INFORMATION: X is Hyp
<220> FEATURE:
<221> NAME/KEY: MOD_RES
<222> LOCATION: (7)..(7)
<223> OTHER INFORMATION: X is Cha
<220> FEATURE:
<221> NAME/KEY: MOD_RES
<222> LOCATION: (10)..(10)
<223> OTHER INFORMATION: X is D-Phe

<400> SEQUENCE: 34

Xaa Lys Arg Pro Xaa Gly Xaa Ser Pro Xaa
1               5                   10

<210> SEQ ID NO 35
<211> LENGTH: 10
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is Ahx

<400> SEQUENCE: 35

Xaa Lys Arg Pro Pro Gly Phe Ser Pro Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is Ahx
<220> FEATURE:
<221> NAME/KEY: MOD_RES
<222> LOCATION: (5)..(5)
```

```
<223> OTHER INFORMATION: X is Hyp
<220> FEATURE:
<221> NAME/KEY: MOD_RES
<222> LOCATION: (7)..(7)
<223> OTHER INFORMATION: X is Cha

<400> SEQUENCE: 36

Xaa Lys Arg Pro Xaa Gly Xaa Ser Pro Leu
1               5                   10

<210> SEQ ID NO 37
<211> LENGTH: 6
<212> TYPE: PRT
<213> ORGANISM: artificial sequence
<220> FEATURE:
<223> OTHER INFORMATION: linker peptide

<400> SEQUENCE: 37

Gly Gly Ser Gly Gly Ser
1               5

<210> SEQ ID NO 38
<211> LENGTH: 5
<212> TYPE: PRT
<213> ORGANISM: artificial sequence
<220> FEATURE:
<223> OTHER INFORMATION: linker peptide

<400> SEQUENCE: 38

Ala Ser Ala Ser Ala
1               5

<210> SEQ ID NO 39
<211> LENGTH: 5
<212> TYPE: PRT
<213> ORGANISM: artificial sequence
<220> FEATURE:
<223> OTHER INFORMATION: linker peptide

<400> SEQUENCE: 39

Pro Ser Gly Ser Pro
1               5

<210> SEQ ID NO 40
<211> LENGTH: 5
<212> TYPE: PRT
<213> ORGANISM: artificial sequence
<220> FEATURE:
<223> OTHER INFORMATION: linker peptide

<400> SEQUENCE: 40

Pro Ser Pro Ser Pro
1               5

<210> SEQ ID NO 41
<211> LENGTH: 10
<212> TYPE: PRT
<213> ORGANISM: Artificial Sequence
<220> FEATURE:
<223> OTHER INFORMATION: Peptidic B1R Agonists
<220> FEATURE:
<221> NAME/KEY: MOD_RES
<222> LOCATION: (1)..(1)
<223> OTHER INFORMATION: Xaa is Sar
<220> FEATURE:
<221> NAME/KEY: MOD_RES
<222> LOCATION: (5)..(5)
<223> OTHER INFORMATION: Xaa is Hyp
<220> FEATURE:
```

```
<221> NAME/KEY: MOD_RES
<222> LOCATION: (7)..(7)
<223> OTHER INFORMATION: Xaa is Cpg
<220> FEATURE:
<221> NAME/KEY: MOD_RES
<222> LOCATION: (10)..(10)
<223> OTHER INFORMATION: Xaa is D-Phe

<400> SEQUENCE: 41

Xaa Lys Arg Pro Xaa Gly Xaa Ser Pro Xaa
1               5                   10

<210> SEQ ID NO 42
<211> LENGTH: 4
<212> TYPE: PRT
<213> ORGANISM: artificial sequence
<220> FEATURE:
<223> OTHER INFORMATION: linker peptide

<400> SEQUENCE: 42

Gly Gly Gly Gly
1

<210> SEQ ID NO 43
<211> LENGTH: 5
<212> TYPE: PRT
<213> ORGANISM: artificial sequence
<220> FEATURE:
<223> OTHER INFORMATION: linker peptide

<400> SEQUENCE: 43

Gly Gly Gly Gly Ser
1               5

<210> SEQ ID NO 44
<211> LENGTH: 10
<212> TYPE: PRT
<213> ORGANISM: artificial sequence
<220> FEATURE:
<223> OTHER INFORMATION: linker peptide

<400> SEQUENCE: 44

Gly Gly Gly Gly Ser Gly Gly Gly Gly Ser
1               5                   10

<210> SEQ ID NO 45
<211> LENGTH: 15
<212> TYPE: PRT
<213> ORGANISM: artificial sequence
<220> FEATURE:
<223> OTHER INFORMATION: linker peptide

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 20
<212> TYPE: PRT
<213> ORGANISM: artificial sequence
<220> FEATURE:
<223> OTHER INFORMATION: linker peptide

<400> SEQUENCE: 46

Gly Gly Gly Gly Ser Gly Gly Gly Gly Ser Gly Gly Gly Gly Ser Gly
1               5                   10                  15

Gly Gly Gly Ser
```

```
                              20

<210> SEQ ID NO 47
<211> LENGTH: 25
<212> TYPE: PRT
<213> ORGANISM: artificial sequence
<220> FEATURE:
<223> OTHER INFORMATION: linker peptide

<400> SEQUENCE: 47

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 48
<211> LENGTH: 30
<212> TYPE: PRT
<213> ORGANISM: artificial sequence
<220> FEATURE:
<223> OTHER INFORMATION: linker peptide

<400> SEQUENCE: 48

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 49
<211> LENGTH: 10
<212> TYPE: PRT
<213> ORGANISM: Artificial sequence
<220> FEATURE:
<223> OTHER INFORMATION: B1R targeting compounds
<220> FEATURE:
<221> NAME/KEY: MOD_RES
<222> LOCATION: (1)..(1)
<223> OTHER INFORMATION: X is Ahx

<400> SEQUENCE: 49

Xaa Lys Arg Pro Pro Gly Phe Ser Pro Leu
1               5                   10

<210> SEQ ID NO 50
<211> LENGTH: 5
<212> TYPE: PRT
<213> ORGANISM: artificial sequence
<220> FEATURE:
<223> OTHER INFORMATION: linker peptide

<400> SEQUENCE: 50

Gly Gly Gly Gly Gly
1               5

<210> SEQ ID NO 51
<211> LENGTH: 4
<212> TYPE: PRT
<213> ORGANISM: artificial sequence
<220> FEATURE:
<223> OTHER INFORMATION: linker peptide

<400> SEQUENCE: 51

Lys Lys Lys Lys
1
```

COMPOSITIONS TARGETING BRADYKININ RECEPTOR B1 FOR MEDICAL IMAGING OF CANCER AND OTHER DISORDERS

This application is a U.S. national stage application under 35 U.S.C. § 371 of International Application No. PCT/CA2013/050707, titled COMPOSITIONS TARGETING BRADYKININ RECEPTOR B1 FOR MEDICAL IMAGING OF CANCER AND OTHER DISORDERS, filed Sep. 13, 2013, hereby incorporated by reference in its entirety, which claims priority to U.S. Provisional Application No. 61/700,804, filed Sep. 13, 2012.

FIELD OF THE INVENTION

The present invention relates to the fields of medical imaging and radiotherapy and, in particular, to compositions comprising radiolabelled peptidic and non-peptidic compounds for imaging tissues or tumours expressing the bradykinin B1 receptor.

BACKGROUND OF THE INVENTION

Bradykinin B1 and B2 receptors (B1R and B2R) are G protein-coupled receptors (GPCRs) and have long been known to have an important role in pain and inflammation pathways (Campos et al, *TRENDS in Pharmacological Sciences* 2006, 27:646-651; Calixto et al, *British Journal of Pharmacology* 2004, 143:803-818). The peptides, bradykinin (BK; Arg-Pro-Pro-Gly-Phe-Ser-Pro-Phe-Arg [SEQ ID NO:5]) and kallidin (Lys-BK; Lys-Arg-Pro-Pro-Gly-Phe-Ser-Pro-Phe-Arg [SEQ ID NO:6]), are produced by enzymatic cleavage of kininogens and act as the endogenous agonists for the constitutively expressed and widely distributed B2R (Leeb-Lundberg et al, *Pharmacological Reviews* 2005, 57:27-77). The removal of the C-terminal Arg from BK and kallidin by carboxypeptidase N generates [des-Arg$^9$]BK and [des-Arg$^{10}$]kallidin, respectively, which are the natural agonists for the inducible B1R (Leeb-Lundberg et al, ibid.).

B1R is known to be involved in various types of pain and inflammatory syndromes (Calixto et al, *British Journal of Pharmacology,* 2004, 143:803-818), cardiovascular inflammatory pathologies, such as endotoxic shock, atheromatous disease and myocardial ischemia (McLean et al, *Cardiovascular Research,* 2000, 48:194-210) and a variety of cancers (Molina et al. *Breast Cancer Research and Treatment* 2009, 118:499-510; Taub et al. *Cancer Research* 2003, 63:2037-2041; Chee et al. *Biological Chemistry* 2008, 389:1225-1233; Yang et al, *Journal of Cellular Biochemistry* 2010, 109:82-92; Raidoo et al, *Immunopharmacology* 1999, 43:255-263; and Wu et al, *International Journal of Cancer* 2002, 98:29-35).

Receptors can be useful targets for various in vivo imaging techniques (see, Mankoff et al., *Journal of Nuclear Medicine,* 2008, 49:149S-163S). Receptor imaging, however, presents certain challenges. For example, receptor imaging probes need to have high specific activity, so that these compounds can be used in low quantities to provide an imaging signal, in order to avoid saturating the receptors. Techniques such as positron emission tomography (PET) and single-photon emission computed tomography (SPECT) are, therefore, preferred for molecular imaging of receptors as these techniques employ radionuclides and can generate images using nano- to picomolar amounts of imaging probes. Even with techniques such as PET and SPECT, however, it is important that the imaging probe exhibits sufficiently low nonspecific binding to avoid interference with visualization at the target site(s), as well as clearance rates that are sufficiently slow to allow for uptake at the target site(s) but rapid enough to allow the uptake to be visualized without interference from unbound probe.

Radionuclides that can be used in SPECT typically have longer half-lives than those used in PET. Typical radionuclides for SPECT imaging include $^{123}$I, $^{99m}$Tc, $^{67}$Ga, $^{111}$In, and $^{201}$Tl, whereas the primary radionuclides for PET imaging are $^{11}$C, $^{18}$F, $^{44}$Sc, $^{64}$Cu, and $^{68}$Ga. While $^{11}$C provides versatility with respect to the type of compound that may be labelled, its use in synthesis is limited due to the availability of only limited precursors and the short half-life (20.3 minutes) of this isotope, which requires its introduction as late as possible in the synthetic pathway as well as an on-site cyclotron to generate the isotope.

SUMMARY OF THE INVENTION

The present invention relates generally to compositions targeting bradykinin receptor B1 for in vivo medical imaging of cancer and other disorders. In accordance with one aspect, the invention relates to a radio-labelled bradykinin B1 receptor (B1R) targeting compound comprising a peptidic or non-peptidic compound that selectively binds to B1R and a radiolabel suitable for in vivo imaging or radiotherapy, or a precursor of said B1R targeting compound.

In one embodiment, the radio-labelled B1R targeting compound, or precursor thereof, comprises a peptidic compound having general Formula (II) or a non-peptidic compound having general Formula (III):

B-L-Xaa$^2$-Arg-Pro-Xaa$^3$-Gly-Xaa$^4$-Ser-Xaa$^5$-Xaa$^6$ (II)

wherein:
B is a radio-labelled moiety, radiometal chelating agent, N-succinimidyl-4-[$^{18}$F]fluorobenzoate (SFB), D-Pra or

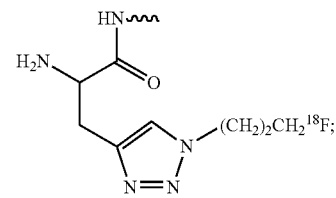

L is a linker;
Xaa$^2$ is absent, Lys or D-Arg;
Xaa$^3$ is Pro or Hyp;
Xaa$^4$ is Phe, Cha, Thi, (α-Me)Phe, Igl or Cpg;
Xaa$^5$ is Pro, D-Tic, D-Hyp, D-βNal or D-Igl, and
Xaa$^6$ is Leu, Ile, D-Phe, Cpg or Oic, [SEQ ID NO:7] and
wherein when B is a radiometal chelating agent, it is optionally chelated to a radiolabel;

(III)

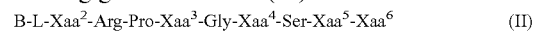

wherein:
R$^1$, R$^4$ and R$^5$ are each independently H or Me;
R$^2$ is H or halo;
R$^3$ is H, Me, halo or OMe;
~NR$^6$R$^7$ is:

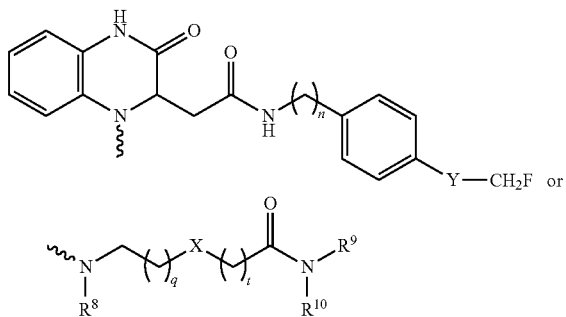

Y is (CH$_2$)$_m$NHR or

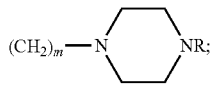

R is (CH$_2$)$_p$;
R$^8$ is Me or Et;
X is O or CH$_2$;
NR$^9$R$^{10}$ is

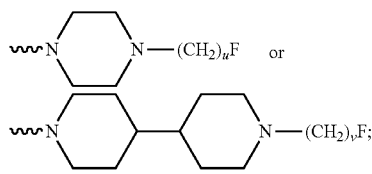

n, m, p, q and t are each independently 0, 1 or 2, and
u and v are each independently 1 or 2, and
wherein F is optionally $^{18}$F.

In accordance with another aspect, the invention relates to a use of a radio-labelled bradykinin B1 receptor (B1R) targeting compound for in vivo imaging of a tissue or cancer expressing or overexpressing B1R, the radio-labelled B1R targeting compound comprising a peptidic or non-peptidic compound that selectively binds to B1R and a radiolabel suitable for in vivo imaging.

In accordance with another aspect, the invention relates to a method for imaging a tissue or cancer expressing or overexpressing bradykinin B1 receptor (B1R) in a patient, comprising administering to the patient a radio-labelled B1R targeting compound comprising a peptidic or non-peptidic compound that selectively binds to B1R and a radiolabel suitable for in vivo imaging.

In certain embodiments, in the uses for, and methods of, in vivo imaging, the radio-labelled B1R targeting compound is a peptidic compound having general Formula (II) or a non-peptidic compound having general Formula (III):

B-L-Xaa$^2$-Arg-Pro-Xaa$^3$-Gly-Xaa$^4$-Ser-Xaa$^5$-Xaa$^6$     (II)

wherein:
B is a radio-labelled moiety or a radiometal chelating agent chelated to a radiolabel;
L is a linker;
Xaa$^2$ is absent, Lys or D-Arg;
Xaa$^3$ is Pro or Hyp;
Xaa$^4$ is Phe, Cha, Thi, (α-Me)Phe, Igl or Cpg;
Xaa$^5$ is Pro, D-Tic, D-Hyp, D-βNal or D-Igl, and
Xaa$^6$ is Leu, Ile, D-Phe, Cpg or Oic, [SEQ ID NO:8]

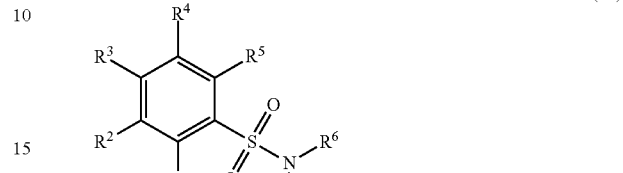

wherein:
R$^1$, R$^4$ and R$^5$ are each independently H or Me;
R$^2$ is H or halo;
R$^3$ is H, Me, halo or OMe;
~NR$^6$R$^7$ is:

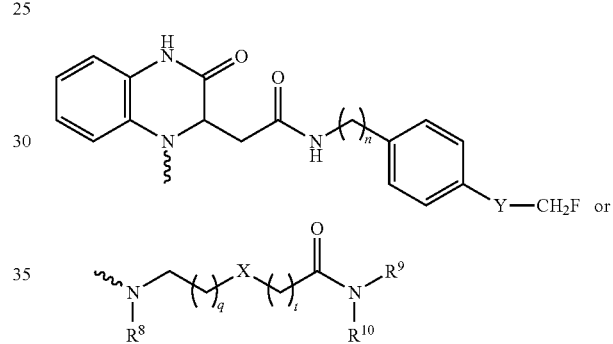

Y is (CH$_2$)$_m$NHR or

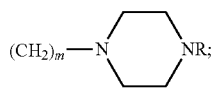

R is (CH$_2$)$_p$;
R$^8$ is Me or Et;
X is O or CH$_2$;
NR$^9$R$^{10}$ is

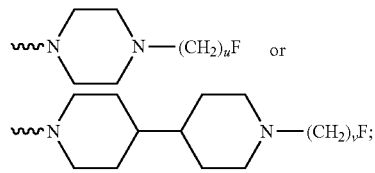

n, m, p, q and t are each independently 0, 1 or 2, and
u and v are each independently 1 or 2, and
wherein F is $^{18}$F.

In accordance with another aspect, the invention relates to a use of a radio-labelled bradykinin B1 receptor (B1R) targeting compound in radiotherapy for treatment of a disease or condition in which B1R is expressed or overexpressed, wherein the radio-labelled B1R targeting compound comprises a peptidic or non-peptidic compound that selectively binds to B1R and a radiolabel suitable for radiotherapy.

In accordance with another aspect, the invention relates to a method of radiotherapy to treat a disease or condition in which bradykinin B1 receptor (B1R) is expressed or overexpressed in a patient, comprising administering to the patient a radio-labelled B1R targeting compound comprising a peptidic or non-peptidic compound that selectively binds to B1R and a radiolabel suitable for radiotherapy.

In certain embodiments, in the uses for, and methods of, radiotherapy, the radio-labelled B1R targeting compound has general Formula (II):

$$B\text{-}L\text{-}Xaa^2\text{-}Arg\text{-}Pro\text{-}Xaa^3\text{-}Gly\text{-}Xaa^4\text{-}Ser\text{-}Xaa^5\text{-}Xaa^6 \quad (II)$$

wherein:
B is a radio-labelled moiety or a radiometal chelating agent chelated to a radiolabel;
L is a linker;
$Xaa^2$ is absent, Lys or D-Arg;
$Xaa^3$ is Pro or Hyp;
$Xaa^4$ is Phe, Cha, Thi, (α-Me)Phe, Igl or Cpg;
$Xaa^5$ is Pro, D-Tic, D-Hyp, D-βNal or D-Igl, and
$Xaa^6$ is Leu, Ile, D-Phe, Cpg or Oic. [SEQ ID NO:9]

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
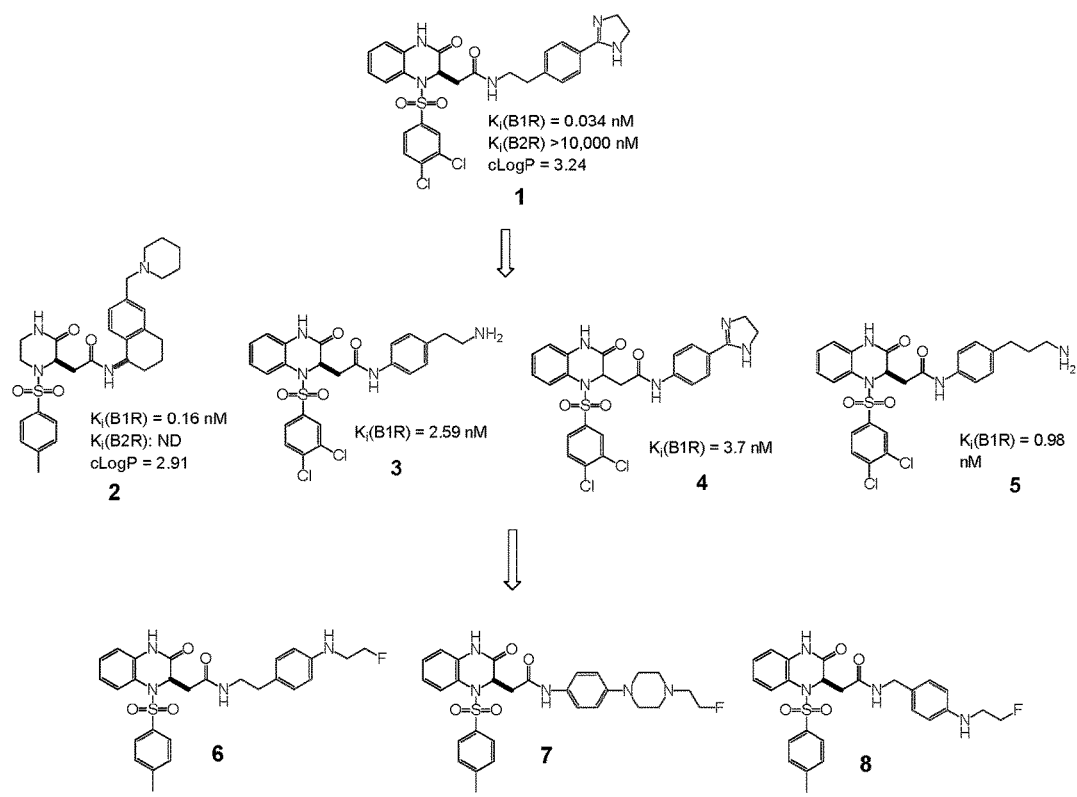
FIG. 1 presents a schematic of the design of B1R targeting small molecules amenable to $^{18}F$ labelling.

In a broad aspect, the invention relates to radio-labelled bradykinin B1 receptor (B1R) targeting compounds and their use in in vivo medical imaging applications for imaging tissues or tumours expressing B1R, or in radiotherapy for treatment of a disease or condition in which B1R is expressed or overexpressed. Accordingly, in certain embodiments, the invention relates to radio-labelled B1R targeting compounds comprising a peptidic or non-peptidic compound that selectively binds to B1R and a radiolabel suitable for in vivo imaging or radiotherapy, and to precursors of such B1R targeting compounds that may subsequently be radio-labelled.

In one aspect, radio-labelled peptide and non-peptide based imaging probes, which selectively bind to B1R and are suitable for in vivo imaging, for example positron emission tomography (PET) or single photon emission computed tomography (SPECT) based imaging, of patients having a disease or disorder in which B1R is expressed such as, for example, cancer, an inflammatory condition, an infection or cardiovascular disease.

In another broad aspect, the invention relates to radio-labelled peptide and non-peptide based compositions, which selectively bind to B1R and are suitable for treatment of patients having a disease or disorder in which B1R is expressed such as, for example, cancer, an inflammatory condition, an infection or cardiovascular disease.

Certain embodiments relate to precursors of the above probes and compositions, which can subsequently be radio-labelled and used as probes or therapeutic compositions. The radiolabel may be introduced, for example, via a group comprised by the precursor which can be modified to incorporate a radiolabel by readily available synthetic procedures, such as "click" chemistry, or via a chelating moiety comprised by the precursor which is capable of chelating a suitable radiolabel.

In certain embodiments, the invention relates to B1R targeting compounds that incorporate or are capable of being labelled with a radioisotope other than $^{11}C$.

In certain embodiments, the invention relates to the use of the peptidic and non-peptidic imaging probes for the detection and early diagnosis of breast cancer, prostate cancer, lung cancer or other malignancies. In some embodiments, the invention relates to the use of the peptidic and non-peptidic imaging probes as adjunct imaging agents for the diagnosis of breast cancer.

In certain embodiments, the invention relates to the use of the peptidic and non-peptidic imaging probes for monitoring response to therapy for a disease or condition in which B1R is expressed such as, for example, cancer, inflammatory disease, infection or cardiovascular disease.

In certain embodiments, the invention relates to the use of the peptidic and non-peptidic imaging probes in diagnostic procedures (non-invasive detection of B1R expression by diagnostic imaging) for predicting response of patients to treatment with B1R antagonists and selecting patients for treatment accordingly.

Based on the data provided in the Examples, radio-labelled B1R compounds are expected to show high contrast, rapid renal clearance, minimal non-target organ uptake, and high tumour to normal tissue ratios, which properties make these compounds well-suited for use as diagnostic imaging agents and for radiotherapy applications.

Definitions

Unless defined otherwise, all technical and scientific terms used herein have the same meaning as commonly understood by one of ordinary skill in the art to which this invention belongs.

It is contemplated that any embodiment discussed herein can be implemented with respect to any method, use or composition of the invention, and vice versa. Furthermore, compositions and kits of the invention can be used to achieve methods and uses of the invention.

As used herein, the term "about" refers to an approximately +/−10% variation from a given value. It is to be understood that such a variation is always included in any given value provided herein, whether or not it is specifically referred to.

The terms "subject" and "patient" as used herein refer to an animal in need of treatment.

The term "animal," as used herein, refers to both human and non-human animals, including, but not limited to, mammals, birds and fish, and encompasses domestic, farm, zoo, laboratory and wild animals, such as, for example, cows, pigs, horses, goats, sheep and other hoofed animals; dogs; cats; chickens; ducks; non-human primates; guinea pigs; rabbits; ferrets; rats; hamsters and mice.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

Naturally occurring amino acids are identified throughout by the conventional three- or one-letter abbreviations indicated in Table 1 below, which are as generally accepted in the peptide art and recommended by the IUPAC-IUB commission in biochemical nomenclature.

TABLE 1

Amino acid codes

| Name | 3-Letter Code | 1-Letter Code |
| --- | --- | --- |
| Alanine | Ala | A |
| Arginine | Arg | R |
| Asparagine | Asp | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptide sequences set out herein are written according to the generally accepted convention whereby the N-terminal amino acid is on the left and the C-terminal amino acid is on the right. By convention, L-amino acids are represented by upper case letters and D-amino acids by lower case letters or preceded by the designation "D."

Bradykinin B1 Receptor (B1R) Targeting Compounds

The bradykinin B1 receptor (B1R) targeting compounds that are radio-labelled as described herein may be peptidic or non-peptidic compounds that specifically bind to B1R.

Peptidic Compounds

In certain embodiments, the B1R targeting compounds are peptidic compounds. The radio-labelled peptidic B1R targeting compounds comprise a B1R targeting moiety that is capable of binding to B1R attached via a linker to a radiolabelled moiety. The radiolabel may be incorporated into the radiolabelled moiety via a covalent bond or via chelation.

Various peptide-based compounds that are capable of binding to B1R are known in the art and may serve as B1R targeting moieties in accordance with certain embodiments of the invention. These compounds include known peptide agonists and antagonists of B1R.

In certain embodiments, the B1R targeting moiety for radio-labelling is derived from a potent agonist or antagonist peptidic compound with high binding affinity and selectivity for B1R. In certain embodiments, the B1R targeting moiety used to prepare the radio-labelled peptidic compounds is a modified version of one of the natural B1R agonists: [des-Arg$^9$]-BK and [des-Arg$^{10}$]-kallidin. Non-limiting examples of such compounds are provided in Tables 2 and 3.

TABLE 2

Peptidic B1R Antagonists

| Name | Sequence[1] |
| --- | --- |
| [Leu$^8$]-des-Arg$^9$-BK | Arg-Pro-Pro-Gly-Phe-Ser-Pro-Leu [SEQ ID NO: 1] |
| Lys[Leu$^8$]-des-Arg$^9$-BK | Lys-Arg-Pro-Pro-Gly-Phe-Ser-Pro-Leu [SEQ ID NO: 2] |
| — | Lys-Arg-Pro-Hyp-Gly-Cha-Ser-Pro-Leu [SEQ ID NO: 10] |
| des-Arg$^9$-HOE 140 | D-Arg-Arg-Pro-Hyp-Gly-Thi-Ser-(D-Tic)-Oic [SEQ ID NO: 11] |

TABLE 2-continued

Peptidic B1R Antagonists

| Name | Sequence[1] |
|---|---|
| des-Arg[9]-NPC 17731 | D-Arg-Arg-Pro-Hyp-Gly-Phe-Ser-(D-Hyp)-(transpropyl-Oic) [SEQ ID NO: 12] |
| R-715 | Ac-Lys-Arg-Pro-Pro-Gly-Phe-Ser-(D-βNal)-Ile [SEQ ID NO: 13] |
| R-892 | Ac-Lys-Arg-Pro-Pro-Gly-(αMe)Phe-Ser-(D-βNal)-Ile [SEQ ID NO: 14] |
| R-954 | Ac-Orn-Arg-Oic-Pro-Gly-(αMe)Phe-Ser-(D-βNal)-Ile [SEQ ID NO: 15] |
| B-9858 | Lys-Lys-Arg-Pro-Hyp-Gly-Igl-Ser-(D-Igl)-Ile [SEQ ID NO: 16] |
| B-9958 | Lys-Lys-Arg-Pro-Hyp-Gly-Cpg-Ser-(D-Tic)-Cpg [SEQ ID NO: 17] |

[1]Abbreviations for non-naturally occurring amino acids are as follows:
Cha: β-cyclohexylalanine;
Cpg: α-cyclopentylglycine
Hyp: hydroxyproline
Igl: 2-indanylglycine
(αMe)Phe: α-methylphenylalanine
βNal: β-napthylalanine
Oic: octahydroindole-2-carboxylic acid
Orn: ornithine
Thi: 2-thienylalanine
Tic: 1,2,3,4-tetrahydroisoquinoline-3-carboxylic acid

TABLE 3

Peptidic B1R Agonists

| Name | Structure[1] |
|---|---|
| [des-Arg[9]]-BK | Arg-Pro-Pro-Gly-Phe-Ser-Pro-Phe [SEQ ID NO: 3] |
| [des-Arg[10]]-kallidin | Lys-Arg-Pro-Pro-Gly-Phe-Ser-Pro-Phe [SEQ ID NO: 4] |
| Sar[D-Phe[8]]-des-Arg[9]-BK | Sar-Arg-Pro-Pro-Gly-Phe-Ser-Pro-(D-Phe) [SEQ ID NO: 18] |
| — | Lys-Arg-Pro-Hyp-Gly-Cha-Ser-Pro-(D-Phe) [SEQ ID NO: 19] |
| SarLys[Hyp[3], Cha[5], Phe[8]]-des-Arg[9]-BK | D-Sar-Lys-Arg-Pro-Hyp-Gly-Cha-Ser-Pro-(D-Phe) [SEQ ID NO: 20] |
| SarLys[Hyp[3], Igl[5], Phe[8]]-des-Arg[9]-BK | D-Sar-Lys-Arg-Pro-Hyp-Gly-Igl-Ser-Pro-(D-Phe) [SEQ ID NO: 21] |
| SarLys[Hyp[3], Cpg[5], Phe[8]]-des-Arg[9]-BK | D-Sar-Lys-Arg-Pro-Hyp-Gly-Cpg-Ser-Pro-(D-Phe) [SEQ ID NO: 41] |

[1]Abbreviations for non-naturally occurring amino acids are as in Table 2; Sar: sarcosine.

Other examples include, but are not limited to, the peptidic B1R antagonists described in International Patent Application Publication No. WO98/07746 and in U.S. Patent Application Publication No. US2008/0064642.

In certain embodiments, the B1R targeting moiety is a B1R antagonist. In some embodiments, the B1R targeting moiety comprises the amino acid sequence as set forth in SEQ ID NO: 1 or 2, or a modified version thereof that retains the ability to bind to B1R. In some embodiments, the B1R targeting moiety comprises the amino acid sequence as set forth in SEQ ID NO: 1, or a modified version thereof that retains the ability to bind to B1R.

In certain embodiments, the B1R targeting moiety is a B1R agonist. In some embodiments, the B1R targeting moiety comprises the amino acid sequence as set forth in SEQ ID NO: 3 or 4, or a modified version thereof that retains the ability to bind to B1R. In some embodiments, the B1R targeting moiety comprises the amino acid sequence as set forth in SEQ ID NO: 3, or a modified version thereof that retains the ability to bind to B1R.

Modified amino acid sequences include, for example, sequences that differ from a parental amino acid sequence in that they comprise one or more amino acid substitutions, additions and/or deletions. Substitutions include substitution of a naturally occurring amino acid with a different naturally occurring amino acid, as well as substitution of a naturally occurring amino acid with a non-naturally occurring amino acid. The non-naturally occurring amino acid may provide the same functionality as the amino acid it replaces or it may provide a different or additional functionality.

Examples of non-naturally occurring amino acids include, but are not limited to, D-amino acids (i.e. an amino acid of an opposite chirality to the naturally occurring form), N-α-methyl amino acids, C-α-methyl amino acids, β-methyl amino acids and D- or L-β-amino acids. More specific examples include, but are not limited to, 2-aminobutyric acid (Abu), 4-aminobutyric acid (γ-Abu), 6-aminohexanoic acid (ε-Ahx or Ahx), α-aminoisobutyric acid (Aib), β-alanine (β-Ala), β-aspartic acid (β-Asp), β-cyclohexylalanine (Cha), α-cyclohexylglycine (Chg), citrulline (Cit), diaminobutyric acid (Dab), diaminopimelic acid (Dap), γ-glutamic acid (γ-Glu), pyroglutamic acid (pGlu), homocysteine (Hcy), homoserine (Hse), hydroxyproline (Hyp), N-ε-dinitrophenyl-lysine (Lys(Dnp)), N-ε-methyl-lysine (Lys(Me)), N,N-ε-dimethyl-lysine (Lys(Me$_2$)), N,N,N-ε-trimethyl-lysine (Lys(Me$_3$)), 3-mercaptopropionic acid (Mpa), L-1-naphthylalanine (L-1-Nal), L-2-naphthylalanine (L-2-Nal), norleucine (Nle), norvaline (Nva), norleucine (Nle), ornithine (Orn), 3-(2-pyridyl)-L-alanine (L-2-Pal), 3-(3-pyridyl)-L-alanine (L-2-Pal), 3-(4-pyridyl)-L-alanine (L-4-Pal), penicillamine (Pen), 4-chlorophenyl-L-alanine (L-4-Cl-Phe), 4-fluorophenyl-L-alanine (L-4-F-Phe), 4-iodophenyl-L-alanine (L-4-I-Phe), 4-nitrophenyl-L-alanine (L-4-NO$_2$-Phe), phenylglycine (Phg), sarcosine (Sar), D-2-methyl-tryptophan (D-2-Me-Trp), phospho-serine (pSer), phospho-threonine (pThr), phospho-tyrosine (pTyr), 11-amino-3.6.9,-trioxa-undecanoic acid (mini-PEG), cysteic acid, cyclohexylalanine, t-butylglycine, t-butylalanine, 3-aminopropionic acid, 2,3-diaminopropionic acid (2,3-diaP), D-2-naphthylalanine (D-2-Nal), 1,2,3,4-tetrahydroisoquinoline-3-carboxylic acid (Tic), octahydroindole-2-carboxylic acid (Oic), α-cyclopentylglycine (Cpg), 2-indanylglycine (Igl), D- or L-2-thienylalanine (Thi), D- or L-3-thienylalanine, D- or L-1-, 2-, 3- or 4-pyrenylalanine, D-(2-pyridinyl)-alanine, D-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har). Other examples include substituted β-alanine (β-Ala) comprising one or more substituents selected from arylsulphonyl (such as benzenesulphonyl or 2-naphthalene sulphonyl) and alkoxycarbonyl (such as t-butoxycarbonyl); phosphono- or sulphated (e.g. —SO$_3$H) non-carboxylate amino acids; D- or L-2-indole(alkyl)alanines, and D- or L-alkylalanines, wherein alkyl is substituted or unsubstituted methyl, ethyl, propyl, hexyl, butyl, pentyl, hexyl, octyl, isopropyl, iso-butyl, or iso-pentyl.

In certain embodiments of the invention, the B1R targeting moiety comprises at least one non-naturally occurring amino acid.

When the sequence contains substitution of a naturally occurring amino acid with a different naturally occurring amino acid, this can be a "conservative" substitution or "non-conservative" substitution. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group. A non-conservative substitution involves the replacement of one amino acid residue by another residue having different side chain properties, for example, replacement of an acidic residue with a neutral or basic residue, replacement of a neutral residue with an acidic or basic residue, replacement of a hydrophobic residue with a hydrophilic residue, and the like.

In certain embodiments, when a B1R targeting moiety comprises substitution of a naturally occurring amino acid with a different naturally occurring amino acid, the substitution is a conservative substitution.

Additions and deletion that may be comprised by a modified amino acid sequence include addition or deletion of one or more amino acid at the N-terminus, the C-terminus or both termini of the parental peptide, as well as addition or deletion of one or more internal amino acids.

In certain embodiments of the invention, the B1R targeting moiety comprises a modified version of the parental peptide Lys[$Leu^8$]-des-$Arg^9$-BK (SEQ ID NO:2). In some embodiments, the B1R targeting moiety comprises a modified version of the parental peptide Lys[$Leu^8$]-des-$Arg^9$-BK (SEQ ID NO:2) that comprises addition of one or more amino acids at the N-terminus. In some embodiments, the B1R targeting moiety comprises a modified version of the parental peptide Lys[$Leu^8$]-des-$Arg^9$-BK (SEQ ID NO:2) that comprises substitution of the amino acid at one or both of positions 3 and 5 with a non-naturally occurring amino acid. In certain embodiments, the B1R targeting moiety comprises a modified version of the parental peptide Lys [$Leu^8$]-des-$Arg^9$-BK (SEQ ID NO:2) that comprises substitution of the amino acid at each of positions 3 and 5 with a non-naturally occurring amino acid. In some embodiments, the B1R targeting moiety comprises a modified version of the parental peptide Lys[$Leu^8$]-des-$Arg^9$-BK (SEQ ID NO:2) that comprises addition of one or more amino acids at the N-terminus and substitution of the amino acid at one or both of positions 3 and 5 with a non-naturally occurring amino acid.

In certain embodiments of the invention, the B1R targeting moiety comprises a modified version of the parental peptide [des-$Arg^{10}$]-kallidin (SEQ ID NO:4). In some embodiments, the B1R targeting moiety comprises a modified version of the parental peptide [des-$Arg^{10}$]-kallidin (SEQ ID NO:4) that comprises substitution of the amino acid at one or more of positions 4, 6 and 9 with a non-naturally occurring amino acid. In certain embodiments, the B1R targeting moiety comprises a modified version of the parental peptide [des-$Arg^{10}$]-kallidin (SEQ ID NO:4) that comprises substitution of the amino acid at each of positions 4, 6 and 9 with a non-naturally occurring amino acid.

In certain embodiments of the invention, the B1R targeting moiety comprises a modified version of the parental peptide [des-$Arg^9$]-BK (SEQ ID NO:3). In some embodiments, the B1R targeting moiety comprises a modified version of the parental peptide [des-$Arg^9$]-BK (SEQ ID NO:3) that comprises addition of one or more amino acids at the N-terminus and substitution of the amino acid at one or more of positions 3, 5 and 8 with a non-naturally occurring amino acid. In certain embodiments, the B1R targeting moiety comprises a modified version of the parental peptide [des-$Arg^9$]-BK (SEQ ID NO:3) that comprises addition of one or more amino acids at the N-terminus and substitution of the amino acid at each of positions 3, 5 and 8 with a non-naturally occurring amino acid.

In some embodiments, certain amino acids of the peptidic B1R targeting compounds disclosed herein may be replaced with alternative amino acids, for example, to improve the biological properties of these agents for their desired diagnostic or therapeutic end uses. In a non-limiting example, the amino acid proline (Pro) may be replaced with the unnatural amino acid hydroxyproline (Hyp) and the amino acid phenylalanine (Phe) may be replaced with the unnatural amino acid cyclohexylalanine (Cha). In another non-limiting example one or more L-form/conformation amino-acids may be replaced with D-form/conformation amino-acids.

Certain embodiments of the invention relate to peptidic B1R-specific PET/SPECT imaging or radio-therapeutic probes for diagnosis or treatment of diseases (including but not limited to cancer, inflammation, infection and cardio-vascular disease) having an amino-acid sequence that is 70%, 80%, 90%, 95% or 99% identical to the amino-acid sequences of the compounds explicitly disclosed herein (see Tables 2 and 3).

Certain embodiments of the invention relate to peptidic B1R targeting compounds in which the amino-acid sequences are reversed relative to the amino-acid sequence orientation of the compounds explicitly disclosed herein (see Tables 2 and 3).

In certain embodiments, the B1R targeting moiety is a peptidic compound of general Formula (I):

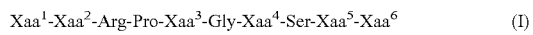
$$Xaa^1\text{-}Xaa^2\text{-}Arg\text{-}Pro\text{-}Xaa^3\text{-}Gly\text{-}Xaa^4\text{-}Ser\text{-}Xaa^5\text{-}Xaa^6 \quad (I)$$

wherein:
$Xaa^1$ is absent, Lys or Sar;
$Xaa^2$ is absent, Lys, Sar or D-Arg;
$Xaa^3$ is Pro or Hyp;
$Xaa^4$ is Phe, Cha, Thi, (α-Me)Phe, Igl or Cpg;
$Xaa^5$ is Pro, D-Tic, D-Hyp, D-βNal or D-Igl, and
$Xaa^6$ is Leu, Ile, D-Phe, Cpg or Oic. [SEQ ID NO:23]

In certain embodiments, in the B1R targeting moiety of general Formula (I):
$Xaa^1$ is absent or Sar;
$Xaa^2$ is Lys;
$Xaa^3$ is Pro or Hyp;
$Xaa^4$ is Phe, Cha, or Cpg;
$Xaa^5$ is Pro, and
$Xaa^6$ is Leu, Ile or D-Phe. [SEQ ID NO:24]

In certain embodiments, in the B1R targeting moiety of general Formula (I):
$Xaa^1$ is absent;
$Xaa^2$ is Lys;
$Xaa^3$ is Pro or Hyp;
$Xaa^4$ is Phe or Cha;
$Xaa^5$ is Pro, and
$Xaa^6$ is Leu or D-Phe. [SEQ ID NO:25]

The peptidic B1R targeting compounds are radio-labelled at a position which is not required for receptor binding and which is separated from the B1R targeting moiety via a linker of appropriate length to minimize interference of the radiolabelled moiety with receptor binding.

In general, suitable linkers are between about 2 and about 50 atoms in length, for example, between about 2 and about 45 atoms in length, between about 2 and about 40 atoms in length, between about 2 and about 35 atoms in length, between about 2 and about 30 atoms in length, between about 2 and about 25 atoms in length, or between about 2 and about 20 atoms in length, or any amount therebetween. In certain embodiments, the linker is at least 2 atoms in length, for example, at least 2, 3, 4, 5, 6, 7, 8, 9, 10, 11, 12, 13, 14, 15, 16, 17, 18, 19 or 20 atoms in length.

It has been shown that modification at the N-terminus of known peptidic B1R agonists and antagonists does not affect their overall binding affinity to B1R (Levesque et al, *Immunopharmacology* 1995, 29:141-147; Bawolak et al, *Journal of Pharmacology and Experimental Therapeutics* 2009, 329:159-168; Talbot et al, *Journal of Neuroinflammation* 2009, 6:11; Gera et al, *International Immunopharmacology* 2008, 8:289-292). Accordingly, in certain embodiments of the invention, the peptidic B1R targeting compounds are modified at their N-terminus to include a suitable linker as described above.

Suitable linkers are typically capable of forming covalent bonds to both the B1R targeting moiety and the radiolabelled moiety. The linker thus comprises functional groups capable of forming covalent bonds, such as primary or secondary amines, hydroxyl groups, carboxylic acid groups or thiol-reactive groups (for example, maleimido groups and chloroacetyl, bromoacetyl and iodoacetyl groups). c3

In certain embodiments, the linker comprises carboxylic acid and amine reactive groups. Examples of such linkers are well known to those of skill in the art and include, but are not limited to, 2-aminobutyric acid (Abu), 4-aminobutyric acid (γ-Abu or Aba), α-aminoisobutyric acid (Aib), 5-aminovaleric acid (5-Ava), 6-aminohexanoic acid (ε-Ahx or Ahx), 7-aminoheptanoic acid, 8-aminooctanoic acid (8-Aoc), 9-aminononanoic acid, 10-aminodecanoic acid, 11-aminoundecanoic acid (11-Aun), [2-(2-amino-ethoxy)-ethoxy]-acetic acid (mini-PEG), {2-[2-(2-amino-ethoxy)-ethoxy]-ethoxy}-acetic acid (mini-PEG3), 3-[2-(2-aminoethoxy)ethoxy]propanoic acid (PEG2), PEG4, and the like. Other examples include peptide linkers such as glycine linkers (for example, GG, GGG, GGGG [SEQ ID NO:42], GGGGG [SEQ ID NO:50]); AAA; SAT; PYP; ASA; SGG; GGSGGS [SEQ ID NO: 37]; ASASA [SEQ ID NO: 38]; PSGSP [SEQ ID NO: 39]; PSPSP [SEQ ID NO: 40]; KKKK [SEQ ID NO:51]; RRRR [SEQ ID NO:32]; Gly$_4$Ser [SEQ ID NO: 43]; (Gly$_4$Ser)$_2$ [SEQ ID NO: 44]; (Gly$_4$Ser)$_3$ [SEQ ID NO: 45]; (Gly$_4$Ser)$_4$ [SEQ ID NO: 46]; (Gly$_4$Ser)$_5$ [SEQ ID NO: 47] and (Gly$_4$Ser)$_6$ [SEQ ID NO: 48].

Various linkers are commercially available, for example, from Pierce Chemical Company (Rockford Ill.), Peptides International (Louisville, Ky.) and Sigma-Aldrich (St Louis, Mo.).

The radiolabelled moiety incorporated into the peptidic B1R targeting compounds via the linker may be a chelating agent that is chelated to a radiolabel or it may be a chemical group covalently bound to a radiolabel. The exact group selected for incorporation into the peptidic B1R targeting compound will depend on the radiolabel to be used and can be readily determined by one skilled in the art. Examples of chelating agents include, but are not limited to, diethylenetriamine pentaacetic acid (DTPA), 1,4,7,10-tetraazacyclotetradecane-1,4,7,10-tetraacetic acid (DOTA), ethylenediaminetetraacetic acid (EDTA), 1,4,7-triazacyclononanetriacetic acid (NOTA), 1,4,7-triazacyclononane-1-glutaric acid-4,7-diacetic acid (NODAGA), 1,8-N,N'-bis-(carboxymethyl)-1,4,8,11-tetraazacyclotetradecane (TE2A), 3,6,9,15-tetraazabicyclo[9.3.1]pentadeca-1(15),11,13-triene-3,6,9-triacetic acid (PCTA), 1-substituted 1,4,7,-tricarboxymethyl-1,4,7,10-teraazacyclododecane triacetic acid (DO3A), DEDPA (6,6'-[1,2-ethanediylbis(iminomethylene)]bis(2-pyridinecarboxylic acid) and 1,4,8,11-tetraazacyclotetradecane-1,4,8,11-tetraacetic acid (TETA). Examples of chemical groups include, but are not limited to, N-succinimidyl-4-[$^{18}$F]fluorobenzoate (SFB) and D-propargylglycine (D-Pra) labelled with $^{18}$F via an $^{18}$F-labelled azide-containing synthon such as 1-azido-3-[$^{18}$F]fluoropropane.

Certain embodiments of the invention, therefore, also provide for unlabelled precursors of the radio-labelled B1R targeting compounds, for example, compounds comprising a chelating agent without a radiolabel, and compounds comprising a reactive moiety (such as D-Pra) that may be reacted with a suitable radio-labelled synthon in order to incorporate the radiolabel. In certain embodiments, the reactive moiety comprises an alkyne group that can be reacted with a radio-labelled synthon comprising an azide group via click chemistry. For example, the reactive moiety may be D-Pra and the radio-labelled synthon may be 1-azido-3-[$^{18}$F]fluoropropane.

Non-limiting examples of radio-labelled peptidic B1R targeting compounds and precursors include compounds of general Formula (II):

B-L-Xaa$^2$-Arg-Pro-Xaa$^3$-Gly-Xaa$^4$-Ser-Xaa$^5$-Xaa$^6$     (II)

wherein:
B is a radio-labelled moiety, radiometal chelating agent optionally chelated to a radiolabel, or D-Pra;
L is a linker;
Xaa$^2$ is absent, Lys or D-Arg;
Xaa$^3$ is Pro or Hyp;
Xaa$^4$ is Phe, Cha, Thi, (α-Me)Phe, Igl or Cpg;
Xaa$^5$ is Pro, D-Tic, D-Hyp, D-βNal or D-Igl, and
Xaa$^6$ is Leu, Ile, D-Phe, Cpg or Oic. [SEQ ID NO:25]

In certain embodiments, in the B1R targeting compounds of general Formula (II), the radio-labelled moiety is N-succinimidyl-4-[$^{18}$F]fluorobenzoate (SFB) or

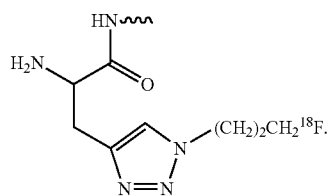

In certain embodiments, in the B1R targeting compounds of general Formula (II), the radiometal chelating agent is DTPA, DOTA, NOTA, NODAGA, TE2A, PCTA, DO3A, DEDPA or TETA.

In certain embodiments, in the B1R targeting compounds of general Formula (II), the linker is Abu, Aba, Aib, 5-Ava, Ahx, 7-aminoheptanoic acid, 8-Aoc, 9-aminononanoic acid, 10-aminodecanoic acid, 11-Aun, a glycine linker (such as GG, GGG or GGGG [SEQ ID NO:42]), mini-PEG, mini-PEG3, PEG2 or PEG4.

In certain embodiments, in the B1R targeting compounds of general Formula (II):
B is DTPA, DOTA, NOTA, D-Pra or

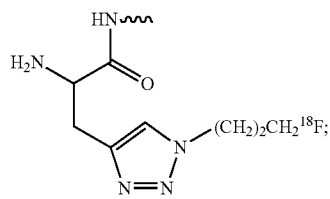

L is Ahx, a glycine linker, mini-PEG, mini-PEG3, PEG2 or PEG4;
Xaa$^2$ is Lys;
Xaa$^3$ is Pro or Hyp;
Xaa$^4$ is Phe, Cha, or Cpg;
Xaa$^5$ is Pro, and
Xaa$^6$ is Leu, Ile or D-Phe. [SEQ ID NO:27]

In certain embodiments, in the B1R targeting compounds of general Formula (II):
B is DTPA, DOTA, NOTA, D-Pra or

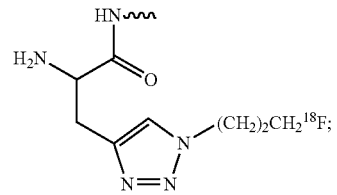

L is Ahx, a glycine linker, mini-PEG, mini-PEG3, PEG2 or PEG4;
Xaa$^2$ is Lys;
Xaa$^3$ is Pro or Hyp;
Xaa$^4$ is Phe or Cha;
Xaa$^5$ is Pro, and
Xaa$^6$ is Leu or D-Phe. [SEQ ID NO:28]

In certain embodiments, the B1R targeting compounds of general Formula (II) have Formula (IV) or (V):

B-L-Lys-Arg-Pro-Hyp-Gly-Cha-Ser-Pro-Leu    (IV) SEQ ID NO:10

B-L-Lys-Arg-Pro-Hyp-Gly-Cha-Ser-Pro-(D-Phe)(V) SEQ ID NO:19 wherein:
B is a radio-labelled moiety, radiometal chelating agent optionally chelated to a radiolabel, or D-Pra, and
L is a linker.

In certain embodiments, in the B1R targeting compounds of Formula (IV) or (V):
is DTPA, DOTA, NOTA, D-Pra or

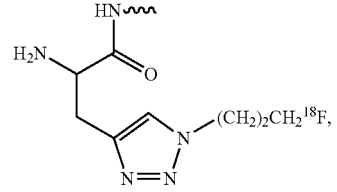

and
L is Ahx, a glycine linker, mini-PEG, mini-PEGS, PEG2 or PEG4.

Suitable radiolabels for incorporation into the peptidic B1R targeting compounds include for example $^{18}$F, $^{123}$I, $^{99m}$Tc, $^{111}$In, $^{68}$Ga, $^{66}$Ga, $^{61}$Cu, $^{64}$Cu, $^{67}$Cu, $^{86}$Y, $^{90}$Y, $^{213}$Bi, $^{177}$Lu, $^{186}$Re, $^{188}$Re and $^{44}$Sc. The exact radiolabel selected for incorporation into the peptidic B1R targeting compound will be dependent on the nature of the chelating agent or chemical group present in the compound for radiolabel attachment and the intended use of the final compound. For example, $^{18}$F, $^{123}$I, $^{99m}$Tc, $^{111}$In, $^{68}$Ga, $^{66}$Ga, $^{64}$Cu and $^{44}$Sc are suitable for PET and/or SPECT imaging, and $^{111}$In, $^{64}$Cu, $^{67}$Cu, $^{90}$Y, $^{213}$Bi, $^{177}$Lu, $^{186}$Re and $^{188}$Re are suitable for radiotherapy applications. Selection of an appropriate label taking these factors into account can be readily made by one skilled in the art. One skilled in the art will also appreciate the certain radioisotopes may require modification to facilitate their incorporation into the peptides and/or for stabilization. For example, $^{18}$F may be used in the form of $^{18}$F—Al to allow for chelation by a chelating group on the peptide. Likewise, $^{186}$Re and $^{188}$Re may be used in the form of Re(CO)$_3$.

In certain embodiments of the invention, the radio-labelled peptidic B1R targeting compounds and precursors include peptides selected from the group of:

D-Pra-Ahx-Lys-Arg-Pro-Hyp-Gly-Cha-Ser-Pro-(D-Phe) [SEQ ID NO: 33] (Peptide 1);
DTPA-Ahx-Lys-Arg-Pro-Hyp-Gly-Cha-Ser-Pro-(D-Phe) [SEQ ID NO: 34] (Peptide 2);
Ga-DOTA-PEG2-Lys-Arg-Pro-Hyp-Gly-Cha-Ser-Pro-Leu [SEQ ID NO: 10] (Peptide 3);
Ga-DOTA-Ahx-Lys-Arg-Pro-Pro-Gly-Phe-Ser-Pro-Leu [SEQ ID NO: 35] (Peptide 4);

appropriate tissue(s) or organ(s). Conjugates include peptidic compounds fused to one or more biological moieties as well as peptidic compounds in which the amino-terminus and/or carboxy-terminus and/or one or more amino acid side chain has been derivatized with a suitable chemical substituent group for conjugation to one or more chemical or biological moieties. Examples of such chemical or biological moieties include, but are not limited to, various carriers,

[SEQ ID NO: 34]

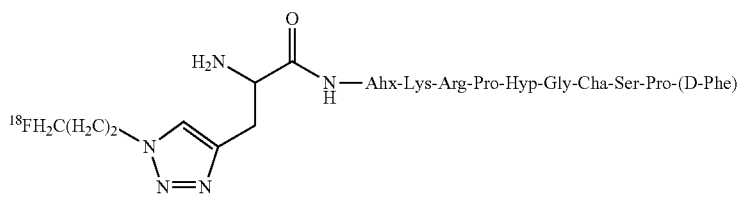

(Peptide 5)

DOTA-PEG2-Lys-Arg-Pro-Hyp-Gly-Cha-Ser-Pro-Leu [SEQ ID NO:10] (Peptide 6);
DOTA-Ahx-Lys-Arg-Pro-Pro-Gly-Phe-Ser-Pro-Leu [SEQ ID NO: 35] (Peptide 7);
Ga-DOTA-Gly-Gly-Lys-Arg-Pro-Hyp-Gly-Cha-Ser-Pro-Leu [SEQ ID NO: 29] (Peptide 8);
DOTA-Gly-Gly-Lys-Arg-Pro-Hyp-Gly-Cha-Ser-Pro-Leu [SEQ ID NO: 29] (Peptide 9);
Ga-DOTA-Gly-Gly-Lys-Arg-Pro-Hyp-Gly-Cha-Ser-Pro-Leu [SEQ ID NO: 29];
DOTA-Gly-Gly-Lys-Arg-Pro-Hyp-Gly-Cha-Ser-Pro-Leu [SEQ ID NO: 29] (Peptide 11);
Ga-DOTA-Ahx-Lys-Arg-Pro-Hyp-Gly-Cha-Ser-Pro-(D-Phe) [SEQ ID NO: 34] (Peptide 12);
DOTA-Gly-Gly-Lys-Arg-Pro-Hyp-Gly-Cha-Ser-Pro-(D-Phe) [SEQ ID NO: 30] (Peptide 13);
In-DTPA-Gly-Gly-Lys-Arg-Pro-Hyp-Gly-Cha-Ser-Pro-Leu [SEQ ID NO: 29] (Peptide 14);
DTPA-Gly-Gly-Lys-Arg-Pro-Hyp-Gly-Cha-Ser-Pro-Leu [SEQ ID NO: 29] (Peptide 15);
Re(CO)$_3$-DTPA-Gly-Gly-Lys-Arg-Pro-Hyp-Gly-Cha-Ser-Pro-Leu [SEQ ID NO:29] (Peptide 16);
DOTA-Gly-Gly-Lys-Arg-Pro-Hyp-Gly-Cha-Ser-Pro-Leu [SEQ ID NO: 29] (Peptide 17);
Al—F-NOTA-Gly-Gly-Lys-Arg-Pro-Hyp-Gly-Cha-Ser-Pro-Leu [SEQ ID NO: 29] (Peptide 18); and
NOTA-Gly-Gly-Lys-Arg-Pro-Hyp-Gly-Cha-Ser-Pro-Leu [SEQ ID NO: 29] (Peptide 19).
The non-labelled peptides listed above can be optionally chelated to a radio-metal such as $^{18}$F, $^{123}$I, $^{99m}$Tc, $^{111}$In, $^{68}$Ga, $^{66}$Ga, $^{64}$Cu, $^{67}$Cu, $^{90}$Y, $^{213}$Bi, $^{177}$Lu, $^{186}$Re, $^{188}$Re and $^{44}$Sc.

The radio-labelled peptidic B1R targeting compounds according to the invention may be prepared by standard peptide and synthetic chemistry procedures from commercially available starting materials. Exemplary, non-limiting procedures are provided in the Examples.

In certain embodiments, the invention relates to conjugates of the above-described peptidic compounds, in which the peptidic compound is conjugated to one or more additional chemical or biochemical moieties that provide additional functionality to the peptide, for example, increased stability, improved bioavailability or improved pharmacokinetics and/or that assist in delivery of the peptide to the appropriate tissue(s) or organ(s). Conjugates include peptidic compounds fused to one or more biological moieties as well as peptidic compounds in which the amino-terminus and/or carboxy-terminus and/or one or more amino acid side chain has been derivatized with a suitable chemical substituent group for conjugation to one or more chemical or biological moieties. Examples of such chemical or biological moieties include, but are not limited to, various carriers, lipophilic moieties, antibodies and other biological ligands, liposomes, polymeric matrices, non-polymeric matrices, particles such as gold particles, microdevices and nanodevices, and nano-scale semiconductor materials.

Non-Peptidic Compounds

In certain embodiments, the B1R targeting compounds are non-peptidic compounds. While peptidic radiotracers offer the possibility of manipulation at the non-receptor-binding domain for radio-labelling and to optimize pharmacokinetics, they are less likely to cross the blood-brain barrier for brain tumour imaging and in certain cases may be prone to cleavage by peptidases. Conversely, radio-labelled small molecule antagonists offer the possibility of imaging brain tumours such as gliomas that express B1R, and likely have higher in vivo stability. The radio-labelled B1R-targeting non-peptidic compounds may be derived, for example, from pharmacophores with high binding affinity and selectivity to B1R. The modification of the pharmacophores for radio-labelling should be within a moiety not critical for receptor binding such that the modification does not significantly affect the B1R binding affinity and selectivity of the compound.

A large number of potent and selective small molecule B1R antagonists have been developed by pharmaceutical companies for the management of chronic pain (see, for example, Huang et al, Journal of Medicinal Chemistry 2010, 53:5383-5399; Kuduk et al, Current Topics in Medicinal Chemistry 2008, 8:1420-1430; Dziadulewicz et al, Expert Opinion on Therapeutic Patents 2005, 15:829-859). Certain embodiments of the invention relate to the modification of the pharmacophores of these B1R antagonists for the design of B1R targeting radiotracers.

In certain embodiments of the invention, the non-peptidic B1R targeting compounds are based on a arylsulfonamide-containing pharmacophore and have the general Formula (III):

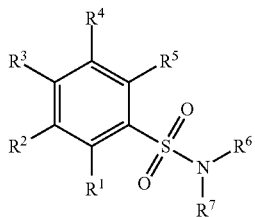

(III)

wherein:

$R^1$, $R^4$ and $R^5$ are each independently H or Me;

$R^2$ is H or halo;

$R^3$ is H, Me, halo or OMe;

~$NR^6R^7$ is:

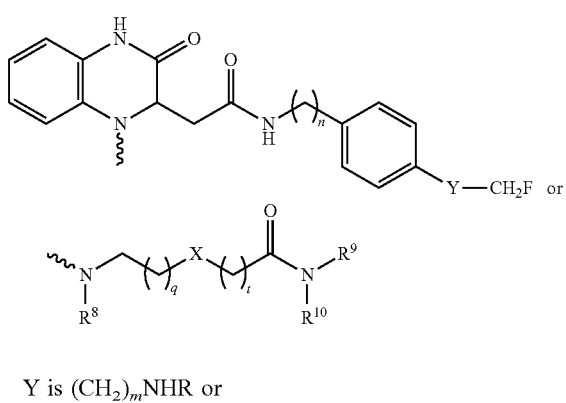

Y is $(CH_2)_m NHR$ or

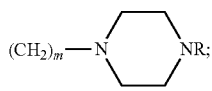

R is $(CH_2)_p$;

$R^8$ is Me or Et;

X is O or $CH_2$;

$NR^9R^{10}$ is

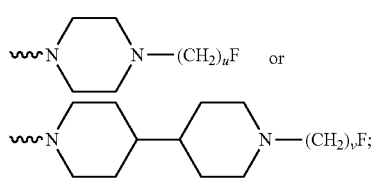

n, m, p, q and t are each independently 0, 1 or 2, and u and v are each independently 1 or 2, and wherein F is optionally $^{18}F$.

In certain embodiments, the non-peptidic compounds of general Formula III are based on a pharmacophore derived from compound 1 (see FIG. 1), which is an arylsulfonamide dihydroquinoxalinone derivative developed by Merck (Su et al, *Journal of American Chemical Society* 2003, 125:7516-7517) and have the general Formula (VI):

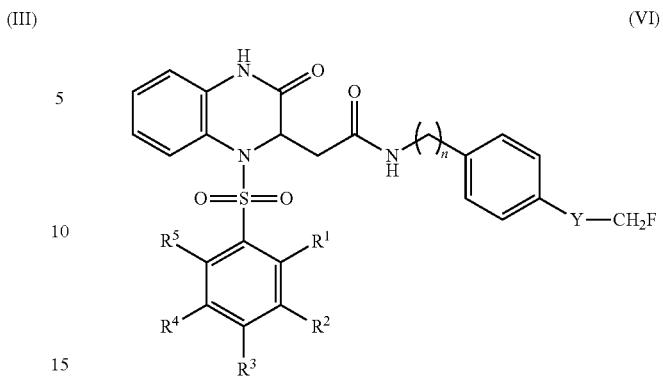

(VI)

wherein:

$R^1$, $R^4$ and $R^5$ are each independently H or Me;

$R^2$ is H or halo;

$R^3$ is H, Me, halo or OMe;

Y is $(CH_2)_m NHR$ or

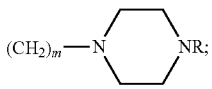

R is $(CH_2)_p$;

n, m and p are each independently 0, 1 or 2, and wherein F is optionally $^{18}F$.

In certain embodiments, in the compounds of general Formula (VI):

$R^1$ is H;

$R^2$ is H or halo;

$R^3$ is H, Me or halo, and $R^4$ and $R^5$ are each H.

In certain embodiments, in the compounds of general Formula (VI):

$R^1$ is H;

$R^2$ is H or Cl, and $R^3$ is Me or Cl.

In certain embodiments, in the compounds of general Formula (VI):

$R^1$ is H;

$R^2$ and $R^3$ are halo, and $R^4$ and $R^5$ are each H.

In certain embodiments, in the compounds of general Formula (VI):

$R^1$ and $R^2$ are H;

$R^3$ is Me, and $R^4$ and $R^5$ are each H.

In certain embodiments, in the compounds of general Formula (VI):

m is 0, and p is 1.

In certain embodiments, in the compounds of general Formula (VI):

$R^1$ is H;

$R^2$ is H or Cl;

$R^3$ is Me or Cl;

$R^4$ and $R^5$ are each H;

m is 0, and p is 1.

In certain embodiments, in the compounds of general Formula (VI) of any of the preceding embodiments, halo is Cl.

In certain embodiments, the compounds of general Formula (VI) include compounds 6, 7 and 8:

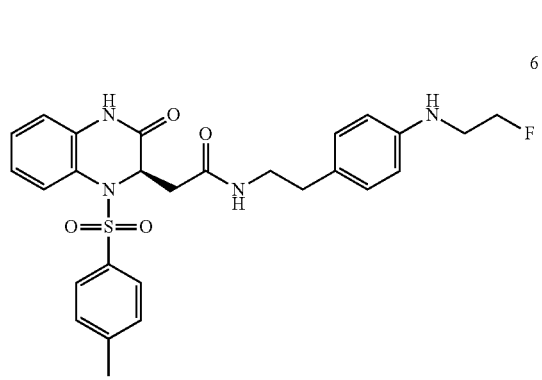

6

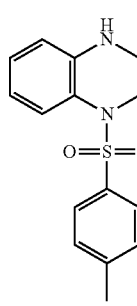

7

8

In certain embodiments, the compounds of general Formula (VI) include compounds 6, 7 and 8 in which F is $^{18}$F (i.e. compounds 6a, 7a and 8a):

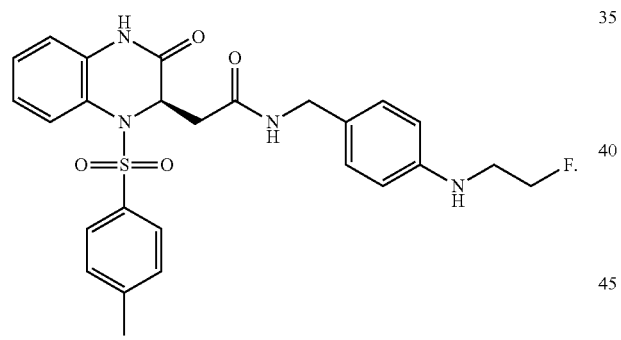

6a

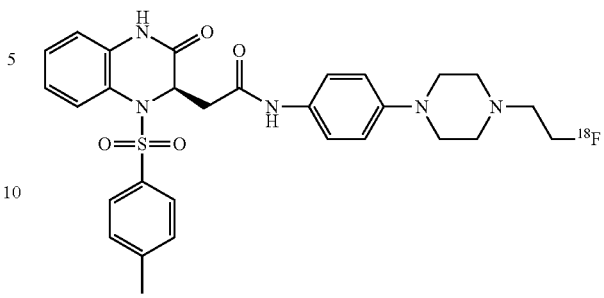

7a

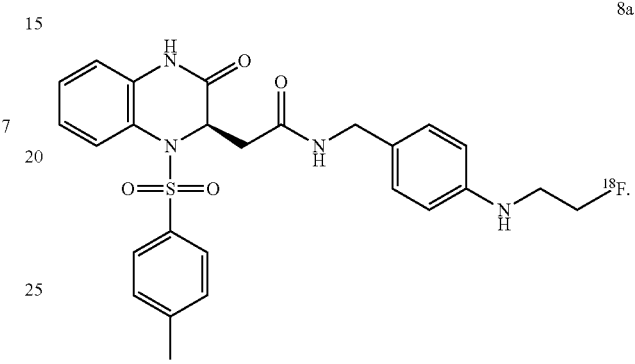

8a

Compounds of general Formula (VI) may be prepared from commercially available starting materials using standard synthetic chemistry protocols. Exemplary, non-limiting synthetic pathways are provided as Schemes 1-3 in the Examples.

In certain embodiments, the non-peptidic compounds of general Formula (III) have the general Formula (VII):

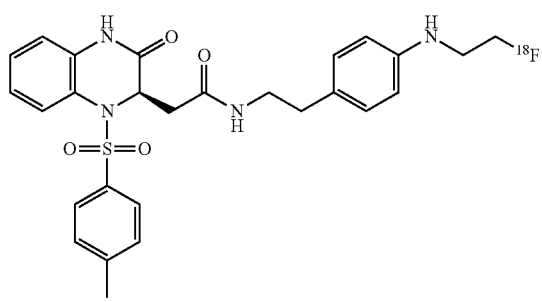

(VII)

wherein:
$R^1$, $R^4$ and $R^5$ are each independently H or Me;
$R^2$ is H or halo;
$R^3$ is H, Me, halo or OMe;
$R^8$ is Me or Et;
X is O or $CH_2$;
~$NR^9R^{10}$ is

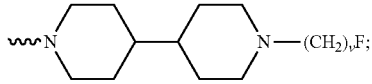

q and t are each independently 0, 1 or 2;
u and v are each independently 1 or 2;
wherein F is optionally $^{18}$F.

In certain embodiments, in the compounds of general Formula (VII), halo is Cl.

In certain embodiments, in the compounds of general Formula (VII):
$R^1$ is H or Me;
$R^2$ is H;
$R^3$ is OMe;
$R^4$ is H, and
$R^5$ is H or Me.

In certain embodiments, in the compounds of general Formula (VII), X is O.

In certain embodiments, in the compounds of general Formula (VII):
$R^1$ and $R^5$ are each independently H or Me;
$R^2$ is H;
$R^3$ is OMe;
$R^4$ is H;
X is O, and
t is 1 or 2.

In certain embodiments, in the compounds of general Formula (VII):
$R^1$ is H or Me;
$R^2$ is H;
$R^3$ is OMe;
$R^4$ is H;
$R^5$ is H or Me;
X is O;
$NR^9R^{10}$ is

[structure: ⁓N—piperidine—piperidine—N—(CH$_2$)$_t$F]

and
t is 1 or 2.

In certain embodiments, in the compounds of general Formula (VII):
$R^1$ is Me;
$R^2$ is H;
$R^3$ is OMe;
$R^4$ is H, and
$R^5$ is Me.

In certain embodiments, in the compounds of general Formula (VII):
$R^1$ is Me;
$R^2$ is H;
$R^3$ is OMe;
$R^4$ is H, and
$R^5$ is Me.
X is O;
t is 1 or 2.

In certain embodiments, the compounds of general Formula (VII) include compounds 15 and 15a:

[structure 15]

[structure 15a]

Compounds of general Formula (VII) may be prepared from commercially available starting materials using standard synthetic chemistry protocols. An exemplary, non-limiting synthetic pathway is provided as Scheme 4 in the Examples.

In certain embodiments, compounds of general Formula (III), (VI) or (VII) may possess a sufficiently acidic group, a sufficiently basic group, or both functional groups, and accordingly react with a number of organic and inorganic bases, or organic and inorganic acids, to form pharmaceutically acceptable salts. The term "pharmaceutically acceptable salt" as used herein, refers to a salt of a compound of Formula (III), (VI) or (VII), which is substantially non-toxic to living organisms. Typical pharmaceutically acceptable salts include those salts prepared by reaction of the compound of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napthalene-2-sulfonate, mandelate and the like. Pharmaceutically acceptable acid addition salts of particular interest are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing pharmaceutically acceptable salts thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a pharmaceutically acceptable salt is usually not of a critical nature, so long as the salt as a whole is pharmacologically acceptable and as long as the counterion does not contribute undesired qualities to the salt as a whole.

In some embodiments, the present invention further encompasses pharmaceutically acceptable solvates of a compound of Formula (III), (VI) or (VII). Many of the compounds of Formula (III), (VI) or (VII) can combine with solvents such as water, methanol, ethanol and acetonitrile to form pharmaceutically acceptable solvates such as the corresponding hydrate, methanolate, ethanolate and acetonitrilate.

Pharmaceutical Compositions

The radio-labelled B1R targeting compounds are typically formulated for administration to a patient. Certain embodiments of the invention thus relate to pharmaceutical compositions comprising one or more of the radio-labelled B1R targeting compounds and a pharmaceutically acceptable carrier, diluent, or excipient. The pharmaceutical compositions are prepared by known procedures using well-known and readily available ingredients.

The pharmaceutical compositions comprising the radio-labelled B1R targeting compounds are typically formulated for parenteral administration. The term parenteral as used herein includes subcutaneous, intradermal, intra-articular, intravenous, intraperitoneal, intramuscular, intravascular, intrasternal, intrathecal injection or infusion techniques.

In certain embodiments, the pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

Uses

In certain embodiments, the invention relates to the use of the radio-labelled B1R targeting compounds in in vivo medical imaging applications or in radiotherapy in patients having a disease or disorder associated with expression or overexpression of B1R.

Diagnostic Applications

Certain embodiments relate to diagnostic applications of the radio-labelled B1R targeting compounds for imaging a cancer or tissue in which B1R is expressed or overexpressed, for example, in oncology, inflammation or cardiovascular disease.

Oncology

Overexpression of B1R has been demonstrated in many malignancies, including early breast and prostate cancers (prostatic intraepithelial neoplasia and malignancy), lung cancers and brain cancers. Certain embodiments of the invention thus contemplate that the radio-labelled B1R targeting compounds could be used as imaging probes for cancers of the breast, prostate, lung and brain.

In the breast, ductal carcinomas in situ also overexpress the B1R receptor. Overexpression of B1R has been observed in 76% of primary breast cancers. In the prostate, benign prostate lesions do not overexpress B1R. Accordingly, certain embodiments of the invention contemplate that the radio-labelled B1R compounds will find use as probes for the diagnosis of early stage breast cancer, prostate cancer and other malignancies. Based on the data provided in the Examples, radio-labelled B1R compounds are expected to show high contrast, rapid renal clearance, minimal non-target organ uptake, and high tumour to normal tissue ratios, which properties make these compounds well-suited for use as imaging agents for cancer diagnosis, including diagnosis of early stage cancer.

Certain embodiments of the invention contemplate the use of the radio-labelled B1R compounds as adjunct imaging agents for the diagnosis of breast cancer. In some embodiments, the radio-labelled B1R compounds can be labelled with positron emitters and could be used with positron emission mammography (or breast gamma imaging) to detect abnormal breast lesions at an early stage, and/or be used to characterize equivocal lesions on mammography or breast MRI, which would be followed up with repeat examinations rather than biopsy.

Certain embodiments of the invention contemplate that the radio-labelled B1R compounds may be used as probes to localize primary or recurrent prostate cancers in patients with elevated tumour markers (such as elevated PSA). Such imaging agents could find use, for example, to confirm the diagnostic of malignancy, guide focal ablative treatment if the disease is localized, or guide salvage treatment in the case of prostate cancer recurrence.

In some embodiments of the invention, it is contemplated that the radio-labelled B1R compounds may be used as PET/SPECT imaging probes to assist with precise localization of primary or recurrent prostate cancer in order to guide and assist with focal ablative therapies.

In some embodiments, the invention contemplates that the radio-labelled B1R compounds could be used to monitor response to therapy, by providing an independent assessment of the residual cellular content of a tumour known to overexpress B1R. Overexpression of B1R may be an indicator of angiogenesis in tumours, as B1R is known to have antiangiogenic activity. In certain embodiments, therefore, the radio-labelled B1R compounds could find use to predict or monitor response to anti-angiogenic medications, such as Avastin.

There is some evidence that B1R antagonists might cause growth inhibition in some cancers. In certain embodiments, B1R expression and receptor blockage could be detected by imaging with the radio-labelled B1R compounds, which could then act as a predictive biomarker for treatment success.

In some embodiments, the use of the radio-labelled B1R compounds in multimodality imaging of cancers is contemplated, for example, combined functional imaging and anatomical imaging, such as PET/CT or SPECT/ST. Multimodality imaging may be useful in situations in which a cancer is present, but the uptake of imaging agent is low.

Inflammation

Inflammation and infection can cause local tissue damage, which leads to the overexpression of B1R, which involved in the inflammatory and nociceptive response. Certain embodiments of the invention contemplate that the radio-labelled B1R compounds could be used to provide images outlining sites of active inflammation or infection, and a quantitative assessment disease involvement, in inflammatory disorders of the joints. In some embodiments, the radio-labelled B1R compounds could be used to monitor inflammatory disease activity and response to therapy.

Cardiovascular Disease

B1R has been reported to be overexpressed when the endovascular intima is damaged. Certain embodiments contemplate the use of the radio-labelled B1R compounds to detect endovascular damage, such as can occur with autoimmune vasculitis or atherosclerosis. Some embodiments of the invention contemplate that the radio-labelled B1R compounds could be used, for example, to guide intervention in patients with abdominal aortic aneurysm—the evidence of intimal damage could be a precursor for aneurysm rupture, as a predictor of unstable plaques in coronary artery disease, in order to predict the likelihood of myocardial infarction in patients with borderline coronary stenoses and/or as a guide to whether carotid endarterectomy is needed in patients with stenotic carotid arteries.

Certain embodiments of the invention relate to a peptidic B1R specific imaging probe comprised of the following amino acid sequence: D-Pra-Ahx-Lys-Arg-Pro-Hyp-Gly-Cha-Ser-Pro-D-Phe [SEQ ID NO: 33]. Depending on the particular radio-imaging procedure/application, a chosen radio-label can be incorporated into the probe via reaction of an appropriate radio-labelled synthon with the D-Pra moiety at the N-terminus. In certain embodiments, the radioactive label is $^{18}$F, the synthon is 1-azido-3-[$^{18}$F]fluoropropane and the imaging procedure is positron emission tomography (PET). This probe is useful for specifically imaging cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to a peptidic B1R specific imaging probe comprised of the following amino acid sequence: DTPA-Ahx-Lys-Arg-Pro-Hyp-Gly-Cha-Ser-Pro-D-Phe [DEQ ID NO: 34]. Depending on the particular radio-imaging procedure/application, a chosen radio-label can be incorporated into the probe via reaction of an appropriate radio-labelled synthon with the DTPA moiety at the N-terminus. In some embodiments, the radioactive label is $^{111}$In, the synthon is $^{111}$InCl$_3$ and the imaging procedure is single-photon emission computed tomography (SPECT). This probe is useful for specifically imaging cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to a peptidic B1R specific imaging probe comprised of the following amino acid sequence: DTPA-Ahx-Lys-Arg-Pro-Hyp-Gly-Cha-Ser-Pro-D-Phe [SEQ ID NO: 34]. Depending on the particular radio-imaging procedure/application, a chosen radio-label can be incorporated into the probe via reaction of an appropriate radio-labelled synthon with the DTPA moiety at the N-terminus. In some embodiments, the radioactive label is $^{99m}$Tc, the synthon is $^{99m}$Tc(CO)$_3$(H$_2$O)$_3^+$ and the imaging procedure is SPECT. This probe is useful for specifically imaging cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to a peptidic B1R specific imaging probe comprised of the following amino acid sequence: Ga-DOTA-PEG2-Lys-Arg-Pro-Hyp-Gly-Cha-Ser-Pro-Leu. [SEQ ID NO:10]. Depending on the particular radio-imaging procedure/application, a chosen radio-label can be incorporated into the probe via reaction of an appropriate radio-labelled synthon with the DOTA moiety at the N-terminus. In some embodiments, the radioactive isotope labels include but are not limited to $^{111}$In, $^{68}$Ga, $^{64}$Cu, $^{61}$Cu, $^{86}$Y and $^{44}$Sc and the procedure is diagnostic PET or SPECT imaging. This probe is useful for specifically imaging cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to a peptidic B1R specific imaging probe comprised of the following amino acid sequence: Ga-DOTA-Ahx-Lys-Arg-Pro-Pro-Gly-Phe-Ser-Pro-Leu [SEQ ID NO: 49]. Depending on the particular radio-imaging procedure/application, a chosen radio-label can be incorporated into the probe via reaction of an appropriate radio-labelled synthon with the DOTA moiety at the N-terminus. In some embodiments, the radioactive isotope labels include but are not limited to $^{68}$Ga, $^{64}$Cu, $^{61}$Cu, $^{86}$Y and $^{44}$Sc and the procedure is diagnostic PET or SPECT imaging. This probe is useful for specifically imaging cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to a $^{68}$Ga-labelled peptidic B1R specific imaging probe comprised of the following amino acid sequence: $^{68}$Ga-DOTA-PEG2-Lys-Arg-Pro-Hyp-Gly-Cha-Ser-Pro-Leu [SEQ ID NO:10]. This probe is especially useful for specifically imaging (using PET or SPECT) cancers (including but not limited to cancers of the breast, prostate or lung) or other disease conditions or tissues (including but not limited to inflammation, infection and cardiovascular disease) whereby the tumour or affected/diseased tissue expresses B1R.

Certain embodiments of the invention relate to the small molecule B1R targeting compound Compound 6 (see Scheme 1 for synthetic route and structure). This compound incorporates a 2-fluoroethyl group to facilitate radio-labelling with $^{18}$F-containing synthons for example. In some embodiments, Compound 6 is useful for non-invasive in vivo diagnostic imaging (using techniques including but not limited to PET or SPECT) of cancer (including but not limited to breast, prostate, lung and brain), inflammatory conditions, cardiovascular disease or other conditions whereby the tissue or cells of interest express B1R.

Certain embodiments of the invention relate to the small molecule B1R targeting compound Compound 7 (see Scheme 2 for synthetic route and structure). This compound incorporates a 2-fluoroethyl group to facilitate radio-labelling with $^{18}$F-containing synthons for example. In some embodiments, Compound 7 is useful for non-invasive in vivo diagnostic imaging (using techniques including but not limited to PET or SPECT) of cancer (including but not limited to breast, prostate, lung and brain), inflammatory conditions, cardiovascular disease or other conditions whereby the tissue or cells of interest express B1R.

Certain embodiments of the invention relate to the small molecule B1R targeting compound Compound 8 (see Scheme 3 for synthetic route and structure). This compound incorporates a 2-fluoroethyl group to facilitate radio-labelling with $^{18}$F-containing synthons for example. In some embodiments, Compound 8 is useful for non-invasive in vivo diagnostic imaging (using techniques including but not limited to PET or SPECT) of cancer (including but not limited to breast, prostate, lung and brain), inflammatory conditions, cardiovascular disease or other conditions whereby the tissue or cells of interest express B1R.

Therapeutic Applications

Certain embodiments relate to therapeutic applications of the radio-labelled B1R targeting compounds in cancer. Cancers that are B1R positive could be amenable to treatment by radionuclide therapy. In such applications, the radio-labelled B1R targeting compound would incorporate a radioisotope that delivers a high local dose of radiation. Therapeutic radioisotopes include but are not restricted to $^{177}$Lu, $^{90}$Y, $^{225}$Ac and $^{64}$Cu. A dose of the compound calculated to deliver an effective radiation dose to the tumour, while avoiding or minimizing normal organ damage, is administered to the patient. The accumulated radioactivity in the tumour can lead to cell death and tumour regression. In certain cases, this type of systemic therapy can be effective even in the metastatic setting.

Pharmaceutical Packs or Kits

Certain embodiments of the invention relate to pharmaceutical packs or kits containing one or more B1R targeting compounds, for example, therapeutic or diagnostic packs or kits. The compounds may be provided radio-labelled or as precursors suitable for radio-labelling, in which case the kit may optionally include additional reagents for radio-labelling the compounds.

In certain embodiments, one or more of the components of the kit can be lyophilized and the kit can additionally contain a suitable solvent for reconstitution of the lyophilized components. Individual components of the kit would typically be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

In certain embodiments, the compound(s) are provided in the kit in the form of pharmaceutical compositions suitable for administration to a subject. In this case, if desired, the container may itself be an inhalant, syringe, pipette, eye dropper, or other such like apparatus, from which the composition may be administered to the subject.

To gain a better understanding of the invention described herein, the following examples are set forth. It will be understood that these examples are intended to describe illustrative embodiments of the invention and are not intended to limit the scope of the invention in any way.

EXAMPLES

Example 1

Preparation of B1R Targeting Peptides

Modification at the N-terminus of B1R agonists and antagonists has been shown not to affect the overall binding affinity of these compounds to B1R (Levesque et al, 1995, ibid; Bawolak et al, 2009, ibid; Talbot et al, 2009, ibid; Gera et al, 2008, ibid). This methodology was applied to the design of peptidic B1R radiotracers as described below.

Two types of peptidic probes (Table 4) were designed and synthesized. The first type of probes is derived from a potent B1R agonist:

Sar-Lys-Arg-Pro-Hyp-Gly-Cha-Ser-Pro-(D-Phe) [SEQ ID NO:20]

($K_i$(B1R)=0.06 nM; $K_i$(B2R) >10,000 nM) (Cote et al, Peptides 2009, 30:788-795), and the second type of probe was derived from B1R antagonist sequences:

```
                                          [SEQ ID NO: 10]
       Lys-Arg-Pro-Hyp-Gly-Cha-Ser-Pro-Leu or

[SEQ ID NO: 2]
       Lys-Arg-Pro-Pro-Gly-Phe-Ser-Pro-Leu
```

A linker, 6-aminohexanoic acid (Ahx) or 3-[2-(2-aminoethoxy)ethoxy]propanoic acid (PEG2), was placed to separate the potential radio-labelling site from the C-terminal receptor binding domain in order to retain the binding affinity to B1R. For radio-labelling, a D-propargylglycine (D-Pra), (diethylenetriaminepentaacetic acid (DTPA), or 1,4,7,10-tetraazacyclododecane-1,4,7,10-tetraacetic acid (DOTA) was incorporated at the N-terminus. With an alkyne functional group, peptides incorporating D-Pra can be radio-labelled with $^{18}$F for PET imaging via a click chemistry reaction with $^{18}$F-labelled synthons containing an azide moiety such as 1-azido-3-[$^{18}$F]fluoropropane. The peptides incorporating DTPA can be radio-labelled with $^{111}$In (using $^{111}$InCl$_3$) or with $^{99m}$Tc using $^{99m}$Tc(CO)$_3$(H$_2$O)$_3^+$) for SPECT imaging. The peptides incorporating DOTA can be radio-labelled with various diagnostic PET/SPECT isotopes including $^{111}$In $^{68}$Ga, $^{64}$Cu and $^{44}$Sc for imaging, or $^{177}$Lu and $^{90}$Y for radiotherapy. Other chelators could be incorporated using similar methodology to attach various radiometals, including NOTA, NODAGA, TE2A, PCTA, DO3A and DEDPA.

Peptides were synthesized via the N$^\alpha$-Fmoc solid-phase peptide synthesis strategy starting from Fmoc-D-Phe-Wang resin (for agonist sequence) or Fmoc-Leu-Wang resin (for antagonist sequence). The resin was treated with 20% piperidine to remove the N$^\alpha$-Fmoc protecting group. The amino acids used for coupling were Fmoc-Pro-OH, Fmoc-Ser(tBu)-OH, Fmoc-Cha-OH, Fmoc-Gly-OH, Fmoc-Hyp(tBu)-OH, Fmoc-Arg(Pbf)-OH, Fmoc-Lys(Boc), Fmoc-6-Ahx-OH, Fmoc-D-Pra-OH, and Fmoc-PEG2-OH. The coupling was carried out with standard in situ activating reagents O-benzotriazole-N,N,N',N'-tetramethyl-uronium-hexafluoro-phosphate (HBTU) in the presence of diisopropylethyamine. For coupling of DOTA, the tri-t-butyl ester was used. For the coupling of DTPA, the tetra-t-butyl ester was used. The peptides were deprotected and cleaved from the resin by trifluoroacetic acid with addition of scavengers, and then purified by reversed phase HPLC. The formation of Ga peptide complexes (Peptides 3, 4, 8, 10 and 12) was performed by mixing GaCl$_3$ (5 equivalents) with DOTA-incorporated peptides in 0.1M NaOAc buffer (pH 4.0-4.5) at 80° C. for 15 min, followed by purification by HPLC. The formation of In peptide complex (Peptide 14) was performed by mixing InCl$_3$ (3 equivalents) with the DTPA-incorporated peptide in 0.1 M NaOAc buffer (pH 5.0) at 50° C. for 60 min, followed by purification by HPLC. The formation of Re peptide complex (Peptide 16) was performed by mixing [Re(CO)$_3$(H$_2$O)$_3$]$^+$Br$^-$ (3 equivalents) with the DTPA-incorporated peptide in 0.1M NaCO$_3$ buffer (pH 10.0) at 70° C. for 60 min, followed by purification by HPLC. The formation of Peptide 18 was performed by mixing the NOTA-incorporated peptide with AlCl$_3$ (2.5 equivalents) and KF (5 equivalents) in 0.05M NaOAc buffer (pH 4.2) at 100° C. for 30 min, followed by purification by HPLC.

TABLE 4

B1R Targeting Peptides

| Peptide | Sequence | Mass Analysis* Calculated | Found |
|---|---|---|---|
| 1 | D-Pra-Ahx-Lys-Arg-Pro-Hyp-Gly-Cha-Ser-Pro-(D-Phe)[SEQ ID NO: 33] | [M + H]$^+$:1262.80 | 1263.50 |
| 2 | DPA-Ahx-Lys-Arg-Pro-Hyp-Gly-Cha-Ser-Pro-(D-Phe)[SEQ ID NO: 34] | [M + H]$^+$:1542.90 | 1543.20 |
| 3 | Ga-DOTA-PEG2-Lys-Arg-Pro-Hyp-Gly-Cha-Ser-Pro-Leu[SEQ ID NO: 10] | [M + 2H]$^{2+}$:816.44 | 816.53 |
| 4 | Ga-DOTA-Ahx-Lys-Arg-Pro-Pro-Gly-Phe-Ser-Pro-Leu[SEQ ID NO: 35] | [M + 2H]$^{2+}$:782.42 | 782.66 |
| 8 | Ga-DOTA-Gly-Gly-Lys-Arg-Pro-Hyp-Gly-Cha-Ser-Pro-Leu[SEQ ID NO: 29] | [M + H]$^+$:1587.70 | 1588.80 |
| 10 | Ga-DOTA-Ahx-Lys-Arg-Pro-Hyp-Gly-Cha-Ser-Pro-Leu[SEQ ID NO: 36] | [M + 2H]$^{2+}$:793.44 | 793.66 |
| 12 | Ga-DOTA-Ahx-Lys-Arg-Pro-Hyp-Gly-Cha-Ser-Pro-(D-Phe)[SEQ ID NO: 34] | [M + H]$^+$:1619.76 | 1620.30 |
| 14 | In-DTPA-Ahx-Lys-Arg-Pro-Hyp-Gly-Cha-Ser-Pro-Leu[SEQ ID NO: 36] | [M + H]$^+$:1620.71 | 1621.90 |
| 16 | Re(CO)$_3$-DTPA-Ahx-Lys-Arg-Pro-Hyp-Gly-Cha-Ser-Pro-Leu[SEQ ID NO: 36] | [M + H]$^+$:1778.76 | 1779.00 |
| 18 | Al-F-NOTA-Ahx-Lys-Arg-Pro-Hyp-Gly-Cha-Ser-Pro-Leu[SEQ ID NO: 36] | [M + H]$^+$:1405.70 | 1406.00 |
| BK-ANT | Lys-Arg-Pro-Pro-Gly-Phe-Ser-Pro-Leu (Bachem H-2582)[SEQ ID NO: 2] | | |
| BK-AG | Lys-Arg-Pro-Pro-Gly-Phe-Ser-Pro-Phe (Bachem H-3122)[SEQ ID NO: 4] | | |

*For peptides 3-18, the mass data are for metal-chelated peptides, but the metals (Ga, In and Re) are not radioactive.

Example 2

Preparation of B1R Targeting Small Molecule Compounds

An arylsulfonamide dihydroquinoxalinone derivative (compound 1; see FIG. 1) developed by Merck (Su et al, *Journal of American Chemical Society* 2003, 125:7516-7517) was selected as the pharmacophore. This compound is very selective for B1R ($K_i$=0.034 nM) versus B2R ($K_i$>10,000 nM). In addition, in a panel of assays representing 170 enzymes, receptors, and transporters, Compound 1 exhibited over 5000-fold selectivity for the human B1R receptor. Currently, the derivatives of compound 1 are among the B1R-targeting small molecule antagonists with the best binding affinity to B1R.

The structure-activity relationship of compound 1 (Ransom et al, *European Journal of Pharmacology* 2004, 499: 77-84) suggests that modification of the 3,4-dichlorophenyl group is tolerable as the replacement of the 3,4-dichlorophenyl group with a 2-naphthyl group generates a new derivative with even better binding affinity ($K_i$ =0.016 nM) to B1R. Besides, the 3,4-dichlorophenyl group was replaced with a 4-methylphenyl group in a compound developed by Amgen. In addition, the modification of 4-(4,5-dihydro-1H-imidazol-2-yl)phenylethyl in compound 1 is tolerable as well. As demonstrated by compounds 3-5, changing the length between the 4-dihydroimidazolphenyl group and the amide linkage from 0 in 4 to 2C in 1, or replacing the 4-dihydroimidazolphenyl group in 4 with a 4-aminoethyl group in 3 or a 4-aminopropyl group in 5 did not significantly affect the binding affinity to B1R. However, the 4-dihydroimidazol group (in 1 and 4) or its 4-aminoalkyl replacement (in 3 and 5) is crucial for binding to B1R, and presumably interacts with Glu273 and Asp291 located at the extra-cellular loops of B1R (Su et al, 2003, ibid). Based on this observation, three potential small molecule B1R antagonists (Compounds 6, 7 and 8, see FIG. 1), which are amenable for radio-labelling with $^{18}$F, were prepared. In these three compounds, the 3,4-dichlorophenyl group in Compound 1 was replaced with a 4-methylphenyl group to reduce overall lipophilicity, and the 4-(4,5-dihydro-1H-imidazol-2-yl)phenylethyl in Compound 1 was replaced with a 4-(2-fluoroethylamino)phenylethyl group (in Compound 6), 4-(2-fluoroethylamino)phenylmethyl group (in Compound 8) or a 4-(2-fluoroethyl)-1-piperazinyl]phenyl group (in Compound 7). The 2-fluoroethyl group in these compounds was added for potential $^{18}$F labelling.

Preparation of Compound 6

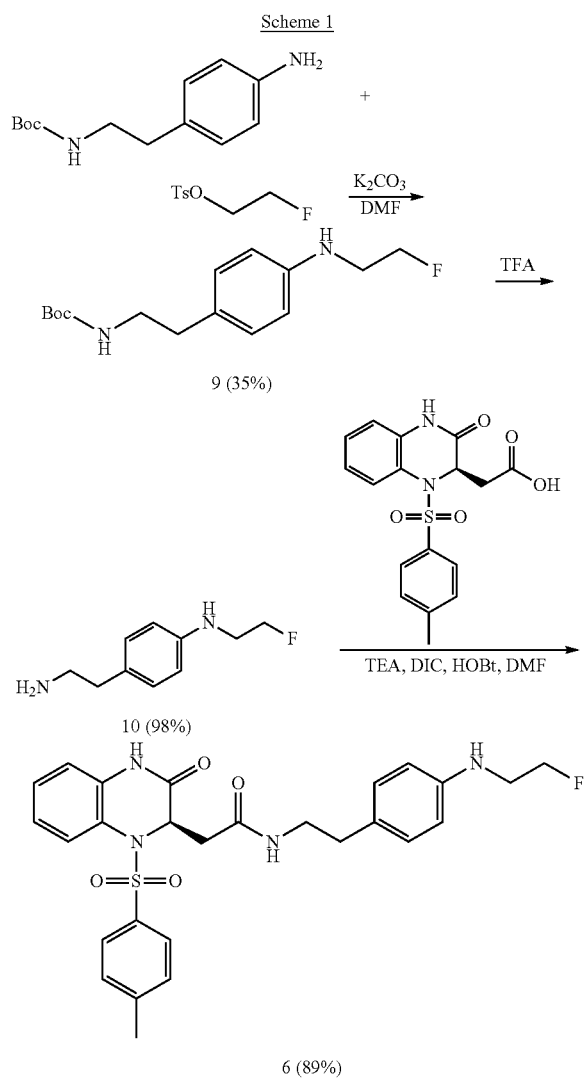

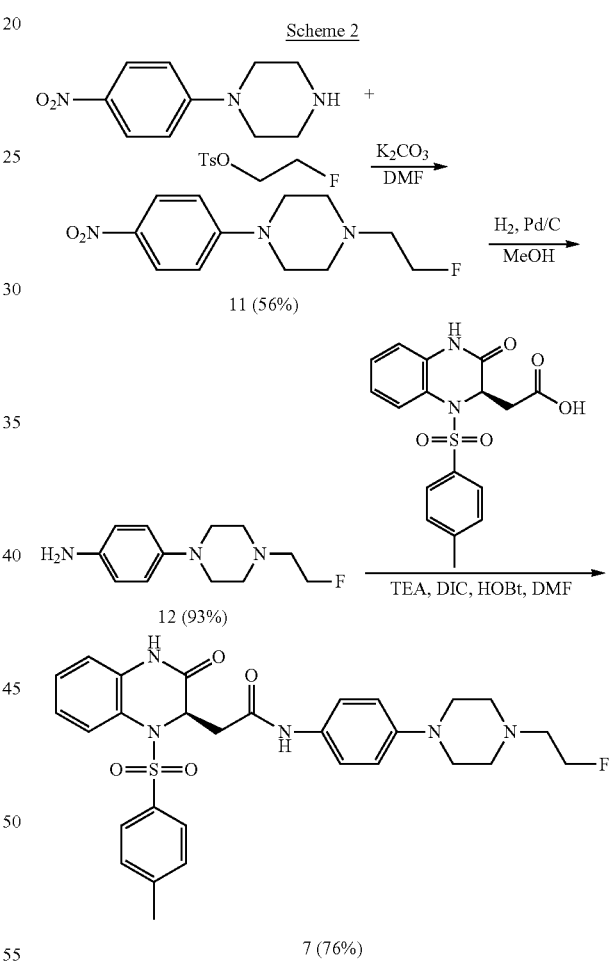

Compound 9: A solution of N-Boc-4-aminophenethylamine (758 mg, 3.2 mmol), 1-fluoro-2-tosyloxyethane (700 mg, 3.2 mmol) and K$_2$CO$_3$ (2.21 g, 16 mmol) in DMF (10 mL) was heated at 70° C. for 2 days. After cooling to room temperature, the mixture was diluted with EtOAc (50 mL) and washed with water (50 mL). The EtOAc fraction was dried over anhydrous MgSO$_4$, concentrated, and chromatographed on silica gel with 1:9 EtOAc/hexanes to obtain Compound 9 as a yellow solid (319 mg, 35%).

Compound 10: A solution of Compound 9 (113 mg, 0.4 mmol) in TFA (1 mL) was stirred at room temperature for one hour. After removing TFA under reduced pressure, CH$_2$Cl$_2$ (25 mL) was added to the residue, and the resulted solution was washed with 1 N NaOH (25 mL). The CH$_2$Cl$_2$ fraction was dried over anhydrous MgSO$_4$, and evaporated to obtain Compound 10 as a yellow oil (71.4 mg, 98%).

Compound 6: A solution of Compound 10 (71.4 mg, 0.39 mmol), 1,2,3,4-tetrahydro-1-[(4-methylphenyl)sulfonyl]-3-oxo-(2R)-2-quinoxalineacetic acid (108 mg, 0.3 mmol), TEA (91 mg, 0.9 mmol), DIC (76 mg, 0.6 mmol), and HOBt.H$_2$O (92 mg, 0.6 mmol) in DMF (2 mL) was stirred at room temperature for 18 hours. After diluting with EtOAc (25 mL), the resulting solution was washed with water (25 mL). The EtOAc fraction was dried over anhydrous MgSO$_4$, concentrated, and chromatographed on silica gel with 8:2 EtOAc/hexanes to obtain Compound 6 as a yellow oil (140 mg, 89%). $^1$H NMR (DMSO-d6) δ 2.33 (s, 3H), 3.08 (m, 1H), 3.17 (m, 1H), 3.30-3.40 (m, 6H), 4.54 (dt, J=47.6, 5.0 Hz, 2H), 4.98 (dd, J=9.0, 5.1 Hz, 1H), 6.59 (d, J=7.9 Hz, 2H), 6.77 (d, J=7.9 Hz, 1H), 6.93 (d, J=8.2 Hz, 2H), 7.10 (t, J=7.6 Hz, 1H), 7.29-7.19 (m, 5H), 7.47 (d, J=7.9 Hz, 1H), 7.92 (t, J=5.4 Hz, 1H), 7.95 (s, 1H), 10.31 (s, 1H).

Preparation of Compound 7

Compound 11: A solution of 1-(4-nitrophenyl)piperazine (995 mg, 4.8 mmol), 1-fluoro-2-tosyloxyethane (1.05 g, 4.8 mmol) and K$_2$CO$_3$ (1.99 g, 14.4 mmol) in DMF (10 mL) was heated at 50° C. for 2 days. After cooling to room temperature, the mixture was diluted with EtOAc (100 mL) and washed with water (100 mL). The EtOAc fraction was dried over anhydrous MgSO$_4$, concentrated, and chromatographed on silica gel with 3:7 EtOAc/hexanes to obtain Compound 11 as a yellow solid (684 mg, 56%).

Compound 12: A solution of Compound 11 (684 mg, 2.7 mmol) in methanol (15 mL) was added to 10% Pd/C (69 mg) and hydrogenated at room temperature under 1 atm for 18 hours. The solution was filtered through celite and evaporated to obtain Compound 12 as a thick oil (559 mg, 93%).

Compound 7: A solution of Compound 12 (112 mg, 0.5 mmol), 1,2,3,4-tetrahydro-1-[(4-methylphenyl)sulfonyl]-3-oxo-(2R)-2-quinoxalineacetic acid (108 mg, 0.3 mmol), TEA (91 mg, 0.9 mmol), DIC (76 mg, 0.6 mmol), and HOBt.H$_2$O (92 mg, 0.6 mmol) in DMF (2 mL) was stirred at room temperature for 1 day, at 50° C. for 1 day, and at 70° C. for 1 day. After diluting with EtOAc (50 mL), the resulting solution was washed with water (50 mL×2). The EtOAc fractions were collected, combined, dried over anhydrous MgSO$_4$, concentrated, and chromatographed on silica gel with 1:9 MeOH/ether to obtain Compound 7 as a yellow solid (130 mg, 76%). $^1$H NMR (DMSO-d6) δ 2.33 (s, 3H), 2.67 (dt, J=28.7, 4.9 Hz, 2H), 3.33-3.34 (m, 10 H), 4.57 (dt, J=47.8, 4.9 Hz, 2H), 5.06 (dd, J=9.2, 5.2 Hz, 1H), 6.81 (d, J=7.9 Hz, 1H), 6.87 (d, J=9.0 Hz, 2H), 7.11 (t, J=8.2 Hz, 1H), 7.21 (d, J=8.3 Hz, 2H), 7.25-7.29 (m, 3H), 7.36 (d, J=9.0 Hz, 2H), 7.48 (d, J=7.2 Hz, 1H), 9.72 (s, 1H), 10.37 (s, 1H).

Preparation of Compound 8

Scheme 3

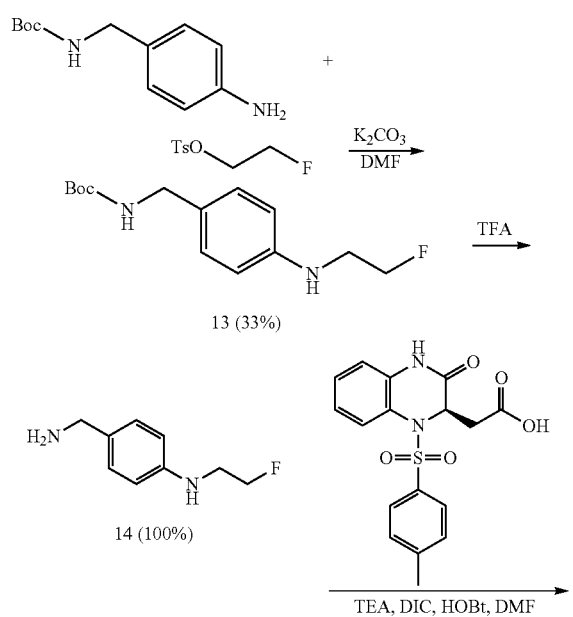

13 (33%)

14 (100%)

TEA, DIC, HOBt, DMF

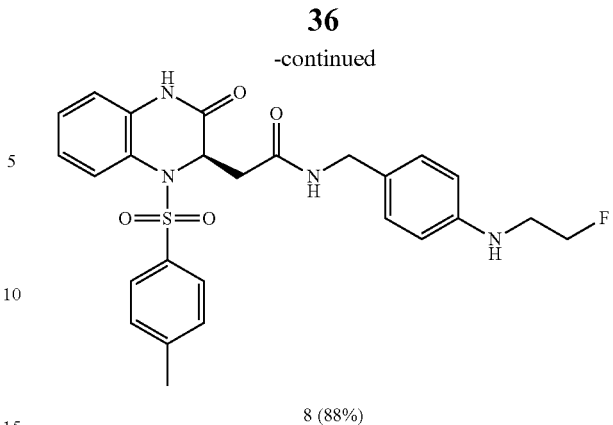

8 (88%)

Compound 13: A solution of 4-(N-Boc-aminomethyl) aniline (1.45 g, 6.5 mmol), 1-fluoro-2-tosyloxyethane (1.42 g, 6.5 mmol) and K$_2$CO$_3$ (4.49 g, 32.5 mmol) in DMF (20 mL) was heated at 70° C. for 5 days and 90° C. for 1 day. After cooling to room temperature, the mixture was diluted with EtOAc (50 mL) and washed with water (50 mL). The EtOAc fraction was dried over anhydrous MgSO$_4$, concentrated, and chromatographed on silica gel with 1:9 EtOAc/hexanes to obtain Compound 13 as a yellow solid (584 mg, 33%).

Compound 14: A solution of Compound 13 (107 mg, 0.4 mmol) in TFA (1 mL) was stirred at room temperature for one hour. After removing TFA under reduced pressure, CH$_2$Cl$_2$ (25 mL) was added to the residue, and the resulting solution was washed with 1 N NaOH (25 mL). The CH$_2$Cl$_2$ fraction was dried over anhydrous MgSO$_4$, and evaporated to obtain Compound 14 as a yellow oil (67.4 mg, 100%).

Compound 8: A solution of Compound 14 (67.4 mg, 0.4 mmol), 1,2,3,4-tetrahydro-1-[(4-methylphenyl)sulfonyl]-3-oxo-(2R)-2-quinoxalineacetic acid (108 mg, 0.3 mmol), TEA (91 mg, 0.9 mmol), DIC (76 mg, 0.6 mmol), and HOBt.H$_2$O (92 mg, 0.6 mmol) in DMF (2 mL) was stirred at room temperature for 23 hours. After diluting with EtOAc (25 mL), the resulted solution was washed with water (25 mL). The EtOAc fraction was dried over anhydrous MgSO$_4$, concentrated, and chromatographed on silica gel with 9:1 EtOAc/hexanes to obtain Compound 8 as a yellow solid (135 mg, 88%). $^1$H NMR (DMSO-d6) δ 2.34 (s, 3H), 3.30 (m, 1H), 3.31-3.34 (m, 4H), 3.36 (m, 1H), 4.53 (dt, J=42.6, 5.0 Hz, 2H), 5.01 (dd, J=9.3, 5.1 Hz, 1H), 5.71 (t, J=6.0 Hz, 1H), 6.57 (d, J=8.5 Hz, 2H), 6.76 (d, J=8.0 Hz, 1H), 6.98 (d, J=8.5 Hz, 2H), 7.08 (t, J=7.9 Hz, 1H), 7.20-7.28 (m, 5H), 7.46 (d, J=8.0 Hz, 1H), 8.18 (s, 1H), 10.31 (s, 1H).

Preparation of Compound 18

Scheme 4

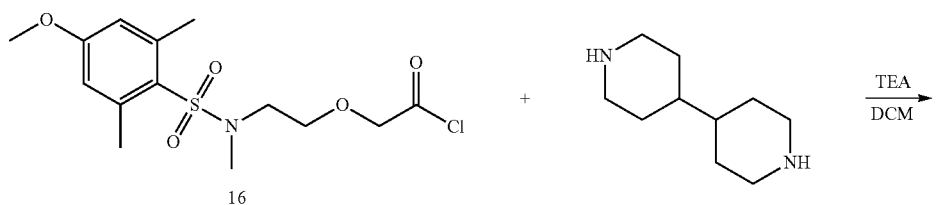

16

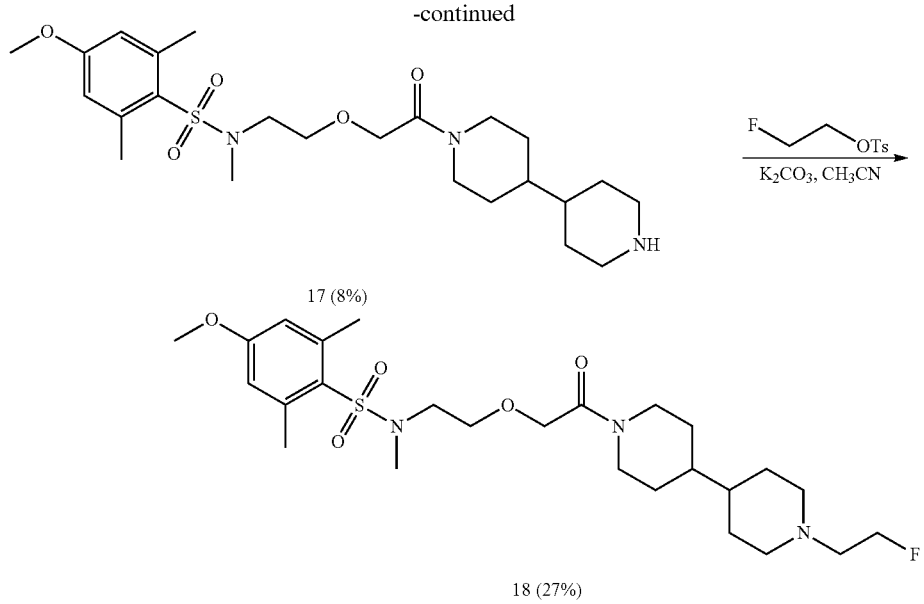

17 (8%)

18 (27%)

Compound 17: [2-[[(2,4-Dichloro-3-methylphenyl)sulfonyl]methylamino]-ethoxy]acetyl chloride (Compound 16) was synthesized according to literature procedure (International Patent Application No. PCT/EP2009/000191 (WO2009/090055). A solution of Compound 16 (0.66 g, 1.89 mmol) in 10 mL DCM was added dropwise to a mixture of 4,4'-bipiperidine (1.59 g, 9.45 mmol) and TEA (0.53 mL, 3.78 mmol) in 30 mL DCM at 0° C. The reaction mixture was allowed to slowly warm to room temperature and stirred overnight. After completion of the reaction, the solid was filtered off and the solvent was evaporated. The crude was purified by chromatography on silica gel with methanol (1% $NH_4OH$) to obtain Compound 17 as a white solid (69 mg, 8%).

Compound 18: A mixture of Compound 17 (50 mg, 0.1 mmol), 2-Fluoroethyl tosylate (27 mg, 0.12 mmol) and $K_2CO_3$ (29 mg, 0.2 mmol) in $CH_3CN$ (7 mL) was refluxed with stirring for 20 hours. After filtration and evaporation, the residue was purified by chromatography on silica gel with ethyl acetate/methanol (3/1, v/v) to obtain Compound 18 as a colorless oil (14 mg, 27%). $^1H$ NMR (300 MHz, $CDCl_3$) δ 6.64 (s, 2H), 4.86 (dd, J=47.4, 3.5 Hz, 2H), 4.61 (d, J=12.8 Hz, 1H), 4.12 (q, J=13.4 Hz, 2H), 3.89 (s, 1H), 3.82 (s, 3H), 3.71 (dd, J=13.7, 8.6 Hz, 4H), 3.39 (t, J=5.4 Hz, 3H), 3.31 (s, 1H), 2.94 (t, J=12.5 Hz, 1H), 2.79 (s, 3H), 2.71 (d, J=12.2 Hz, 1H), 2.61 (s, 6H), 2.50 (d, J=12.7 Hz, 1H), 1.96 (d, J=13.3 Hz, 2H), 1.78 (d, J=11.7 Hz, 4H), 1.55-0.97 (m, 5H); $^{19}F$ NMR (300 MHz, $CDCl_3$) δ 76.03; MS (ESI) Calcd. for $C_{26}H_{42}FN_3O_5S$: m/z 528.28 ([M+H]$^+$); Found: m/z 528.5 ([M+H]$^+$)

Example 3

Preparation of Cells Over-expressing B1R

Cell Culture: Human embryonic kidney cell line HEK293T was purchased as part of Lenti-X™ Expression System (Clontech Laboratories Inc., Mountain View, Calif.). Cells were cultured in high glucose DMEM or RPMI 1640 (StemCell Technologies, Vancouver, BC) supplemented by 10% FBS, 2 mM L-glutamine, 100 U/mL penicillin and 100 µg/mL streptomycin at 37° C. in a humidified incubator containing 5% $CO_2$. Cells at 80-90% confluences were washed with sterile phosphate-buffered saline (1×PBS pH7.4) and harvested with 0.25% trypsin. Number of cells collected was counted using a Scepter handheld automated cell counter (Millipore, Billerica, Mass.).

Gene Transfer and Expression Using Recombinant Lentiviruses: The Lenti-X Lentiviral Expression Systems (Clontech Laboratories Inc., Mountain View, Calif.) was used to induce expression of Green Fluorescent Protein (GFP) and human bradykinin B1 receptor (BKRB1) in human embryonic kidney cells (HEK293). The lentiviral expression vector carrying GFP, pGIPz (GFP) (Open Biosystems, Rockford, Ill.) was obtained from Dr. Samuel Aparicio's laboratory at BCCRC. pGIPz (GFP) carries a puromycin antibiotic resistance selection marker (PuroR). To generate recombinant lentivirus carrying GFP, Lenti-X HT Packaging Systems (Clontech Laboratories Inc.) were transfected together with pGIPz (GFP) into the HEK293T cell line. Cells were allowed to grow for 72 hours before growth medium containing lentiviruses were harvested and used to infect mammalian cells. In brief, 100,000 cells were cultured in 6-well plate up to 70% confluences. Hexadimethrine bromide (polybrene) (Sigma-Aldrich Canada Ltd, Oakville, ON) at 8 µg/mL final concentrations in 0.9% NaCl was used to reduce charge repulsion between the cell membrane and the lentivirus. Growth medium of the overnight cell culture was refreshed post-lentivirus infection and cells were allowed to grow for 48 hours before antibiotic (puromycin) screening started. Cells that survived in the presence 10 µg/mL of puromycin were cross-checked under fluorescence microscopy for green fluorescence detection.

Figure 2:
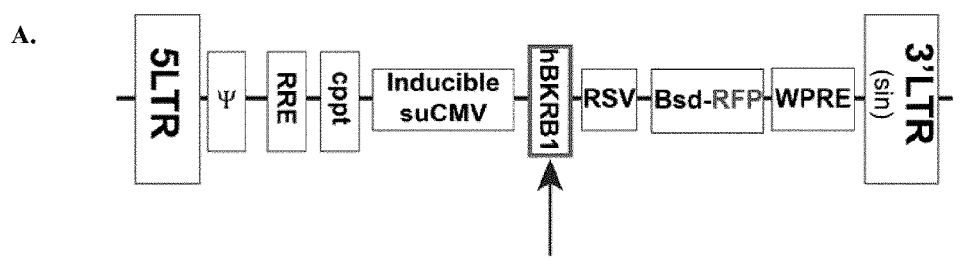
FIG. 2 presents (A) a schematic diagram of lentiviral vector carrying human B1R (BDKRB1) and fusion antibiotic Blasticidin (Bsd) and red fluorescence protein (RFP) dual markers, and fluorescence microscopy of HEK293T::GFP::hB1R cells using red (B) or yellow (C) filter (color not shown).
Figure 2:
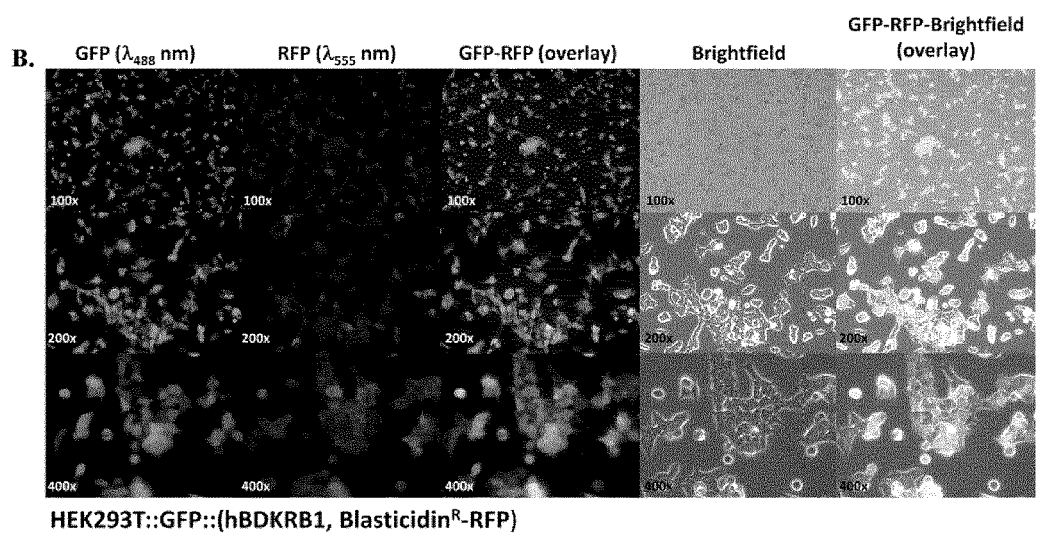

Pre-made inducible lentiviral particles at 1×10$^7$ IFU/mL for expressing human BDKRB1 (bradykinin B1 receptor/B1R) were obtained from GenTarget Inc., San Diego, Calif. (cat. no. LVP291). The B1R open reading frame is constitutively expressed under a tetracycline inducible suCMV promoter. An antibiotic blasticidin (Bsd)-RFP (red fluorescence protein) fusion marker under the RSV promoter is also present in the expression vector to allow for selection of successfully transduced cells. HEK293T::GFP cells were cultured in a 96-well microplate in quadruplicate with the following cell numbers: 1×(~20,000 cells/well), 1/2×, 1/4 ×, and 1/20× in 100 µL of RPMI growth medium with 1% FBS. Duplicate wells received 5×10$^4$ IFU lentivirus carrying human B1R and Bsd-RFP with or without 8 µg/mL of polybrene. The plate was briefly centrifuged at 500 rpm for 5 minutes and incubated at 37° C. for 6 hours before replacement of the culture medium. Blasticidin at 10 µg/mL final concentration was added to growth medium 72 hours later to select transduced cells. Growth medium was refreshed every two days in the presence of blasticidin for about a week before trypsinization and transfer of the cells in larger flasks, consecutively from 6-well plate, T25, T75, and T225. Cells resistant to blasticidin also expressed red fluorescence protein. FIG. 2A shows a schematic representation of the lentiviral vector carrying human B1R (BD-KRB1) provided by GenTarget Inc. Fluorescence microscopy of HEK293T::GFP::hB1R cells showed a membranous and cytoplasmic fluorescence of RFP, suggesting the localization of B1R over-expression (see FIGS. 2B and C).

Example 4

Evaluation of B1R Targeting Compounds In Vitro

The ability of the peptide and small molecule B1R targeting compounds to bind to B1R was assessed in competitive binding assay as described below.

Preparation of Cell Membranes: Ready to use cell membranes (12.5 µg/µL) from CHO-K1 cells over-expressing human B1R were obtained from Perkin Elmer Inc., Waltham, Mass. (cat. no. ES-091-M400UA). Binding using cell membranes from HEK293T::GFP::hB1R (from Example 3) was also tested. In the latter case, the membranes were prepared as follows: 90% confluent cells grown in large flask, T225, were detached and pelleted in a 50 mL conical tube using centrifuge at 1,200 rpm for 5 minutes. Afterward, cells were re-suspended in 20-30 mL of cold 50 mM Tris-HCl pH 7.4. Ice cold cells were disrupted for 15 seconds at 15,000 rpm with a Polytron PT3100 (Kinematica AG, Lucerne, Switzerland). The solution was aliquoted and centrifuged at 4° C. at 17,000×g for 30 minutes. The supernatant was discarded, and then the pellet was dissolved in 1-2 mL of cold salt solution containing 50 mM Tris-HCl pH 7.4 and 100 mM NaCl and incubated for 1 hour on ice. The cell membranes were pelleted by centrifugation at 4° C. at 17,000×g for 30 minutes and resuspended in 200-600 µL of 50 mM Tris-HCl pH 7.4. The cell membrane extract was stored at −80° C. Protein concentration was determined by Bradford assay (cat. no. R1271, Fermentas, Thermo Fisher Scientific, Burlington, ON). 50 ug of cell membranes per well was used for the competitive binding assay. The control was H-Lys-Arg-Pro-Pro-Gly-Phe-Ser-Pro-Leu-OH (BK-ANT; SEQ ID NO:2) obtained from Bachem Americas Inc., Torrance, Calif. (cat. no. H-2582). Radio-labelled control was H-3 labelled [Leu$^9$,des-Arg$^{10}$] kallidin obtained either from American Radiolabelled Chemicals Inc, St. Louis, Mo. (cat. no. ART1609, lot no. 111103, specific activity: 83.8 Ci/mmol, original dilution 1.0 µCi/µL, half-life: 4537 days, stock concentration: 11.906 µM) or Perkin Elmer Inc., Boston, Mass. (cat. no. NET1096250UC, lot no. 1586889, specific activity: 76.0 Ci/mmol, original dilution: 1.0 µCi/µL, half-life: 4537 days, stock concentration: 13.086 µM).

Saturation Binding Assays: Assays were done using 96-well MultiScreen$_{HTS}$ with glass fiber filter and PVDF support obtained from Millipore Corp, Billerica, Mass. (cat. no. MSFB N6B, lot no. R8AN42424). Wells of the Multi-Screen plate were pre-soaked with 0.5% of cold Poly(ethyleneimine) (PEI) (cat. no. P3143, Sigma-Aldrich, St. Louis, Mo.) for 30 minutes. Afterward, wells were washed once with 50 mM of Tris-HCl pH 7.4. Total volume per wells was 200 µL. Increasing concentrations of the radioligand (H-3 labelled [Leu$^9$,des-Arg$^{10}$]-kallidin) from 0.005 to 10 nM concentration were incubated in the presence of cell membranes (50 µg/well), with and without the addition of BK-ANT as a competitor (50 µM). The assay buffer contained 50 mM of Tris-HCl pH 7.4 and 5 mM of MgCl$_2$. The Multiscreen plate was incubated at 27° C. for 15 minutes. The assay was stopped by suctioning the reaction solution through the PVDF membrane filter, and washing the filter with ice cold 50 mM Tris-HCl pH 7.4. Scintillation fluid was added to each well, and the radioactivity was measured using a MicroBeta Trilux Microplate Scintillation and Luminescence Counter (Perkin Elmer Inc., Shelton, Conn.). Graphpad Prism 5 was used to calculate the affinity constant (Kd) and the receptor concentration (Bmax).

The Kd determined in these assays for $^3$H-Des-Arg$^{10}$, Leu$^9$-Kallidin binding to B1R was 6-fold lower in CHO-K1::hB1R cells (Kd=0.5742 nM) than in HEK293T::GFP::hB1R cells (Kd=3.459 nM).

Figure 3:
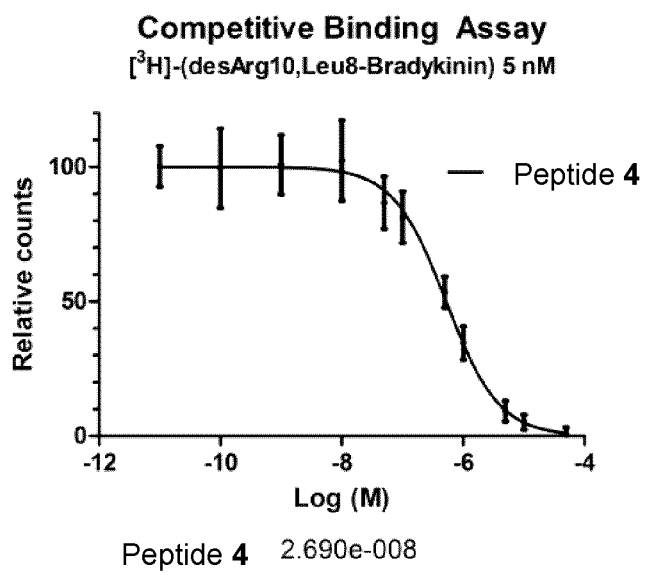
FIG. 3 presents results from representative competition binding assays for two B1R targeted peptides, Peptides 4 (FIG. 3A) and 3 (FIG. 3B).
Figure 3:
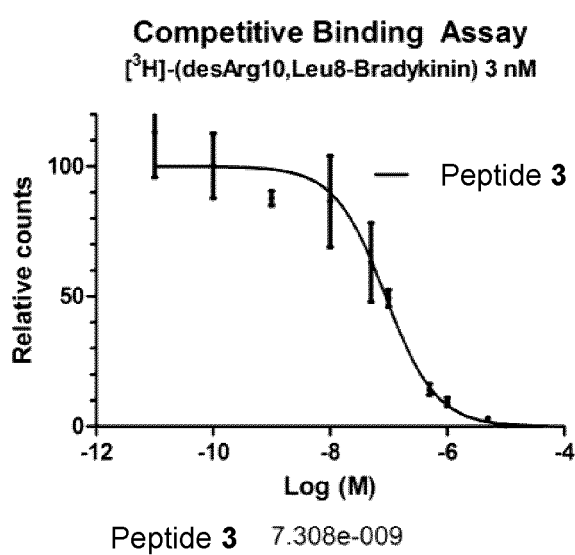

Competitive Binding Assays: Assays were performed using 96-well MultiScreen$_{HTS}$ with glass fiber filter and PVDF support obtained from Millipore Corp, Billerica, Mass. (cat. no. MSFB N6B, lot no. R8AN42424). Wells of the MultiScreen plate were pre-soaked with 0.5% of cold Poly(ethyleneimine) (PEI) (cat. no. P3143, Sigma-Aldrich, St. Louis, Mo.) for 30 minutes. Afterward, wells were washed once with 50 mM of Tris-HCl pH 7.4. Total volume per wells was 200 µL. A fixed concentration of the hot radioligand (1, 3, 5 or 12.5 nM depending on the radioligand; see Table 5) was incubated with progressively higher concentrations ($10^{-11}$ to $10^{-4}$ M) of the non-radioactive competitor of interest in the presence of cell membranes (50 µg/well) and the assay buffer (50 mM Tris-HCl pH 7.4, 5 mM MgCl$_2$). The MultiScreen plate was then incubated at 27° C. for 15 minutes with agitation at 300 rpm. The assay was stopped by suctioning the reaction solution through the bottom PVDF membrane filter and discarded. The membranes were washed 7× with 150 µL/well of cold 50 mM Tris-HCl pH 7.4. Radioactivity was counted using 1450 MicroBeta TriLux—Microplate Scintillation and Luminescence Counter (Perkin Elmer Inc., Shelton, Conn.). Results are shown in Tables 5 and 6 below. Representative competition binding assays for two peptides (Peptides 3 and 4) are shown in FIG. 3.

TABLE 5

Compilation of Results for Individual Competitive Binding Assays

| Compound | Ki (nM) | Hot (nM) | Ligand* | Membranes |
| --- | --- | --- | --- | --- |
| Peptide 1 | 10.9 | 12.5 | BK-AG-ARC | CHO-K1 |
| Compound 7 | 39.5 | 12.5 | BK-AG-ARC | CHO-K1 |
| Peptide 1 | 22.6 | 12.5 | BK-AG-ARC | CHO-K1 |
| Peptide 2 | 131 | 12.5 | BK-AG-ARC | CHO-K1 |
| Compound 7 | 260 | 12.5 | BK-AG-ARC | CHO-K1 |
| Compound 6 | 1007 | 12.5 | BK-AG-ARC | CHO-K1 |
| Compound 7 | 113 | 12.5 | BK-AG-ARC | CHO-K1 |
| Compound 8 | 6921 | 12.5 | BK-AG-ARC | CHO-K1 |
| Compound 7 | 20.7 | 12.5 | BK-ANT-ARC | CHO-K1 |
| Peptide 1 | 74.6 | 12.5 | BK-ANT-ARC | CHO-K1 |
| H-3122 | 0.19 | 4.6 | BK-ANT-ARC | CHO-K1 |
| Peptide 10 | 22.3 | 4.6 | BK-ANT-ARC | CHO-K1 |
| H-3122 | 0.29 | 4.6 | BK-ANT-ARC | CHO-K1 |
| Peptide 10 | 29.0 | 4.6 | BK-ANT-ARC | CHO-K1 |
| Peptide 18 | 8.91 | 4.6 | BK-ANT-ARC | CHO-K1 |

TABLE 5-continued

Compilation of Results for Individual Competitive Binding Assays

| Compound | Ki (nM) | Hot (nM) | Ligand* | Membranes |
|---|---|---|---|---|
| Peptide 3 | 13.3 | 4.6 | BK-ANT-ARC | CHO-K1 |
| H-2582 | 0.35 | 4.6 | BK-ANT-ARC | CHO-K1 |
| Peptide 4 | 2.47 | 4.6 | BK-ANT-ARC | CHO-K1 |
| Peptide 3 | 17.1 | 4.6 | BK-ANT-ARC | CHO-K1 |
| Peptide 18 | 23.8 | 4.6 | BK-ANT-ARC | CHO-K1 |
| Peptide 4 | 3.57 | 4.6 | BK-ANT-ARC | CHO-K1 |
| Peptide 3 | 17.6 | 4.6 | BK-ANT-ARC | CHO-K1 |
| Peptide 4 | 2.23 | 4.6 | BK-ANT-ARC | CHO-K1 |
| Peptide 3 | 16.0 | 4.6 | BK-ANT-ARC | CHO-K1 |
| H-3122 | 0.58 | 4.6 | BK-ANT-ARC | CHO-K1 |
| Peptide 10 | 32.0 | 4.6 | BK-ANT-ARC | CHO-K1 |
| Peptide 18 | 20.7 | 4.6 | BK-ANT-ARC | CHO-K1 |
| Peptide 4 | 1.93 | 4.6 | BK-ANT-ARC | CHO-K1 |
| H-3122 | 0.24 | 4.6 | BK-ANT-ARC | CHO-K1 |
| Peptide 12 | 19.7 | 4.6 | BK-ANT-ARC | CHO-K1 |
| Peptide 18 | 17.1 | 4.6 | BK-ANT-ARC | CHO-K1 |
| H-2582 | 0.29 | 4.6 | BK-ANT-ARC | CHO-K1 |
| Peptide 12 | 29.1 | 4.6 | BK-ANT-ARC | CHO-K1 |
| H-2582 | 0.49 | 4.6 | BK-ANT-ARC | CHO-K1 |
| Peptide 12 | 27.5 | 4.6 | BK-ANT-ARC | CHO-K1 |
| Peptide 8 | 13.5 | 4.6 | BK-ANT-ARC | CHO-K1 |
| H-2582 | 0.29 | 4.5 | BK-ANT-ARC | CHO-K1 |
| Peptide 8 | 8.63 | 4.5 | BK-ANT-ARC | CHO-K1 |
| Peptide 8 | 12.1 | 4.5 | BK-ANT-ARC | CHO-K1 |
| Peptide 14 | 36.5 | 4.5 | BK-ANT-ARC | CHO-K1 |
| Peptide 16 | 404 | 4.5 | BK-ANT-ARC | CHO-K1 |
| Peptide 14 | 42.6 | 4.5 | BK-ANT-ARC | CHO-K1 |
| Peptide 16 | 103 | 4.5 | BK-ANT-ARC | CHO-K1 |
| Peptide 14 | 24.5 | 4.5 | BK-ANT-ARC | CHO-K1 |
| Peptide 16 | 381 | 4.5 | BK-ANT-ARC | CHO-K1 |
| Compound 15 | 0.81 | 4.5 | BK-ANT-ARC | CHO-K1 |
| Peptide 14 | 32.1 | 4.5 | BK-ANT-ARC | CHO-K1 |

*BK-AG-ARC, BK-ANT-ARC and BK-ANT-PE are three $^3$H-labeled radioligands used for the binding affinity measurement.
BK-AG-ARC: [3,4-prolyl-3,4-3H(N)] [Des-Arg$^{10}$]Kallidin from American Radiolabeled Chemicals, Inc. (Cat#ART 1583).
BK-ANT-ARC: [3,4-prolyl-3,4-3H(N)] [Leu$^9$, Des-Arg$^{10}$]Kallidin from American Radiolabeled Chemicals, Inc. (Cat#ART 1609).
BK-ANT-PE is identical to BK-ANT-ARC but from PerkinElmer (Cat# NET1096250UC).

TABLE 6

Summary of Average Binding Constants (Ki) for B1R Targeting Compounds

| | Affinity Ki (nM) | |
|---|---|---|
| Compound | Average | St. Dev. |
| H-3122 | 0.32 | 0.17 |
| H-2582 | 0.35 | 0.10 |
| Peptide 1 | 32.21 | 28.72 |
| Peptide 2 | 131.00 | — |
| Peptide 3 | 16.0 | 1.93 |
| Peptide 4 | 2.55 | 0.71 |
| Peptide 8 | 11.4 | 2.51 |
| Peptide 10 | 27.8 | 4.93 |
| Peptide 12 | 25.4 | 5.06 |
| Peptide 14 | 33.9 | 7.64 |
| Peptide 15 | 295 | 168 |
| Peptide 18 | 18.3 | 6.49 |
| Compound 6 | 1007.00 | — |
| Compound 7 | 108.30 | 108.69 |
| Compound 8 | 6921.00 | — |
| Compound 15 | 0.81 | — |

Example 5

Evaluation of B1R Targeting Compounds In Vivo (Peptide 3)

Preparation of Ga-68 Labelled Peptide 3: Peptide 3 was shown in Example 4 to have a high binding affinity (32.76 nM) for B1R and was selected for radio-labelling and imaging/biodistribution studies. Ga-68 was obtained from a 30-mCi Ge-68/Ga-68 generator (model IGG100) purchased from Eckert & Ziegler. Ga-68 solution eluted from the generator with 0.1 N HCl (5 mL) was purified according to the procedures reported by Zhernosekov et al (*J Nucl Med* 2007, 48:1741-1748). The 97.6% acetone/0.05N HCl solution (0.4 mL) containing ~12 mCi Ga-68 was added to a solution of DOTA-PEG2-Lys-Arg-Pro-Hyp-Gly-Cha-Ser-Pro-Leu SEQ ID NO:10 (0.2 mg) in 0.1 M NaOAc buffer (2 mL, pH4). The resulting solution was heated at 110° C. for 10 min, and then the desired Ga-68 labelled Peptide 3 was purified using an Agilent 1200 HPLC system via an isocratic condition (78% H$_2$O containing 0.1% TFA and 22% CH$_3$CN containing 0.1% TFA) over the course of 25 min at a flow rate of 4.5 mL/min on a Phenomenex Luna C-18 semi-preparative column (250 mm×10 mm, 5 μm) monitored on-line for UV absorption at 220 nm. The fractions of product with a retention time of 14.3 min were collected, diluted with water (15 mL), and passed through a tC18 light sep-pak preactivated with ethanol (10 mL) and water (10 mL). After washing the tC18 light sep-pak with 10 mL water, the Ga-68 labelled Peptide 3 was eluted with ethanol (0.3 mL) and formulated with 3 mL isotonic saline for imaging/biodistribution studies. The radiochemical yield was >80% and the radiochemical purity of the Ga-68 labelled Peptide 3 was >99%.

Tumour Implantation: Imaging and biodistribution experiments were performed using NODSCID IL2RKO mice. Each cage, equipped with enrichments, contained three or four mice. The mice were maintained and the experiments were conducted in accordance with the guidelines established by Canadian Council on Animal Care and approved by Animal Ethics Committee of the University of British Columbia. Mice were housed under pathogen-free conditions and kept on twelve hour light and twelve hour dark cycle in the Animal Research Centre, British Columbia Cancer Research Centre, Vancouver, Canada.

Mice were anesthetised briefly with 2.5% isoflurane in 2.0 L/min of oxygen during cell implantation. After wiping the skin surrounding the injection site with an alcohol prep pad, a 31-Gauge needle was used to inject 10$^7$ HEK293T::GFP and HEK293T::hB1R cells in matrigel (1:1) on the back of the mouse. Imaging was performed once the tumour lump was visible. Tumour size was measured by CT and calculated using the ellipsoid formula: $V^3_{mm}$=width×length×thickness×0.524.

Figure 4:
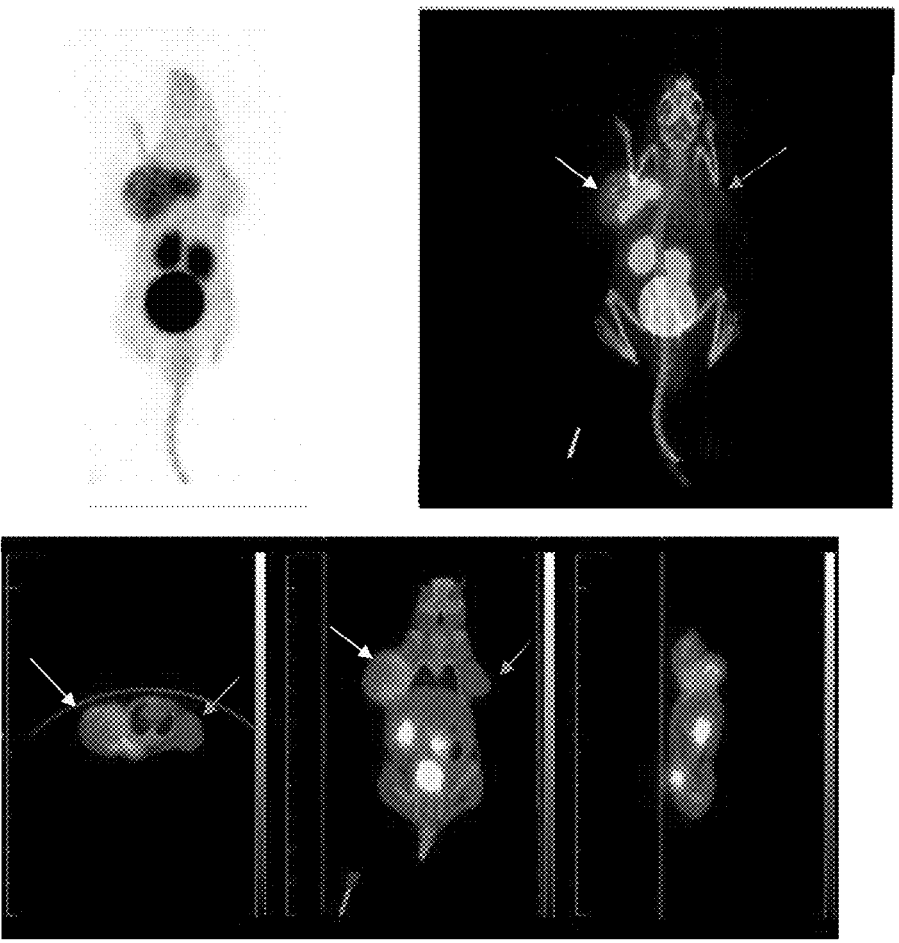
FIG. 4 presents reconstructed Ga-68 Peptide 3 images (1 h post-injection) of SCID IL2R KO mouse bearing tumours derived from HEK293T::GFP (B1R−; right arrows) and HEK293T::hB1R (B1R+; left arrows) cells.

PET/CT Imaging: Each tumour-bearing mouse was injected with ~3.7 MBq of Ga-68 labelled Peptide 3 through the tail vein. The mice were imaged using the BC Cancer Agency Inveon microPET/CT scanner that has a 1.3 mm spatial resolution and a high sensitivity. Briefly, a localization CT scan was first obtained using 3 overlapping positions to cover the entire mouse. This CT scan was used for attenuation and scatter correction after segmentation for reconstructing the PET images. A dynamic acquisition was then performed for 60 minutes, with the mouse under isoflurane sedation. The animals were kept warm by a monitoring system with an integrated heating pad and physiological acquisition system. At the end of the acquisition, the mice were euthanized, and major organs were collected, weighed, and counted to determine the % injected dose per gram of tissue (% ID/g). The biodistribution data are shown in Table 6. The images were reconstructed using OSEM/3DMAP iterative reconstruction, and representative images of Ga-68 labelled Peptide 3 at 1 h post-injection are shown in FIG. 4.

TABLE 6

Biodistribution of Ga-68 Peptide 3 in SCID IL2R
KO tumour-bearing mice at 1 h post-injection

| Tissue | Mouse 1 % ID/g | Mouse 2 % ID/g | Mouse 3 % ID/g | Mouse 4 % ID/g | Average | SD |
|---|---|---|---|---|---|---|
| Plasma | 0.94% | 0.40% | 0.63% | 1.09% | 0.77% | 0.31% |
| Blood | 0.22% | 0.18% | 0.21% | 0.44% | 0.26% | 0.12% |
| Tail | 0.32% | 0.70% | 0.41% | 0.38% | 0.45% | 0.17% |
| Muscle | 0.14% | 0.07% | 0.06% | 0.15% | 0.11% | 0.05% |
| Bone | 0.20% | 0.11% | 0.10% | 0.95% | 0.34% | 0.41% |
| Fat | 0.17% | 0.15% | 0.05% | 0.10% | 0.12% | 0.06% |
| Left Kidney | 4.21% | 4.02% | 7.37% | 4.96% | 5.14% | 1.54% |
| Right Kidney | 6.55% | 3.69% | 3.94% | 12.99% | 6.79% | 4.33% |
| Colon | 0.39% | 0.29% | 0.25% | 0.43% | 0.34% | 0.08% |
| Small Intestine | 0.32% | 0.08% | 0.13% | 0.28% | 0.20% | 0.11% |
| Stomach | 0.10% | 0.06% | 0.10% | 0.17% | 0.11% | 0.05% |
| Spleen | 0.06% | 0.08% | 0.12% | 0.19% | 0.11% | 0.06% |
| Pancreas | 0.22% | 0.08% | 0.07% | 0.17% | 0.13% | 0.07% |
| Liver | 0.19% | 0.09% | 0.13% | 0.24% | 0.16% | 0.07% |
| Heart | 0.25% | 0.08% | 0.16% | 0.26% | 0.19% | 0.09% |
| Lungs | 0.63% | 0.22% | 0.33% | 0.52% | 0.43% | 0.18% |
| RIGHT Tumour (GFP) | 0.20% | 0.17% | 0.21% | 0.35% | 0.23% | 0.08% |
| LEFT Tumour (B1R) | 1.42% | 1.00% | 1.38% | 1.48% | 1.32% | 0.22% |
| Brain | 0.04% | 0.02% | 0.01% | 0.04% | 0.03% | 0.01% |

Discussion: The above Examples demonstrate the development of radiotracers for non-invasively imaging B1R expression in cancers with positron emission tomography (PET) which is considered one of the most powerful molecular imaging modalities due to its quantitative capability and high sensitivity to detect pico- to nano-molar concentrations of molecules. The successfully developed B1R PET imaging agents have potential for early diagnosis of breast, prostate and lung cancers that often over-express B1R. It is worth noting that the most popular cancer imaging agent 2-deoxy-2-[$^{18}$F]fluoro-D-glucose ($^{18}$F-FDG) has not been very successful for use in imaging prostate cancer due to poor image contrast. Since B1R is over-expressed in prostate cancers, but not in surrounding normal prostate tissues, higher image contrast should be obtained by using B1R-targeting radiotracers. If B1R antagonists prove to be effective for cancer therapy, the imaging agents described herein can also be used to identify B1R-positive cancer patients for clinical trials and to optimize the therapeutic dosage for complete blockade of B1R, as well as to select B1R-positive cancer patients who can benefit from B1R-targeted therapies and thus prevent futile treatment on B1R-negative cancer patients. The radio-labelled B1R peptidic and non-peptidic compounds described herein have potential use in both diagnosis and therapy. For diagnostic applications, a single-photon (such as $^{99m}$Tc) or positron emitting (such as $^{68}$Ga, $^{18}$F, $^{44}$Sc, $^{64}$Cu, $^{61}$Cu, $^{86}$Y) radioisotope may be attached to the compound, allowing non-invasive imaging of the abnormal expression of these receptors. For therapeutic applications, such as for cancer treatment, a radioisotope that delivers a high radiation dose (such as $^{177}$Lu, $^{90}$Y, $^{225}$Ac, $^{64}$Cu) can be attached to the compound thus allowing targeted delivery of radiotherapy to the cancers.

Example 5

Evaluation of B1R Targeting Compounds In Vivo
(Peptide 4)

$^{68}$Ga labeling of Peptide 4 was performed in NaOAc buffer (pH 4.1) at 110° C. for 10 min, and [$^{68}$Ga]P03083 was purified by HPLC. PET imaging and biodistribution studies were performed in NODSCID/IL2RKO mice bearing both B1R-negative HEK293T:GFP tumour and B1R-positive HEK293T:hB1R tumour.

Results: The radio-labelling precursor DOTA-Ahx-Lys-[Leu8,desArg9]BK (Peptide 7) was obtained in 37% isolated yield with >99% purity. Peptide 4 binds B1R with high affinity (Ki=12.4 nM), and [$^{68}$Ga]-Peptide 4 could be prepared in high radiochemical yield (92±3%) with >99% radiochemical purity. PET imaging and biodistribution studies showed that the radioactivity was mainly excreted through the renal pathway (kidney uptake: 74.9±29.2% ID/g, 1h post-injection). No specific uptake of [$^{68}$Ga]-peptide 4 to B1R in tumours was observed as the uptakes in both B1R-negative and B1R-positive tumors were comparable (1.1±0.4% ID/g, 1 h post-injection).

Conclusions: [$^{68}$Ga]-Peptide 4 is a potent B1R-targeting PET tracer. The lack of specific uptake in B1R-positive tumours is likely due to the low in vivo stability of this peptide. Modifications were therefore made to improve the in vivo stability of this peptide including replacement of the amino acids adjacent to the sites targeted by the peptidases with unnatural amino acids resulting in Peptide 10, which is predicted to show better in vivo stability and, therefore, might generate higher specific uptake in B1R-positive tumours.

Example 6

Evaluation of B1R Targeting Compounds In Vivo
(Peptides 3, 8, 10 and 12)

For in vivo imaging, HEK-293 and HEK-293 cells stably transfected with the human bradykinin receptor B1 (HEK-293/BKRB1) were inoculated in the flank of immunodeficient mice (NODSCID IL2rKO). PET/CT images were obtained 60 minutes after the intravenous injection of 1-5 MBq of $^{68}$Ga-labelled peptides. A computer tomography image of the mouse was obtained for organ localization and attenuation correction, followed by PET imaging, using a Siemens Inveon multimodality preclinical scanner. Images were acquired over 10-15 minutes for each animal. The results are shown in FIGS. 5-8.

Figure 5:
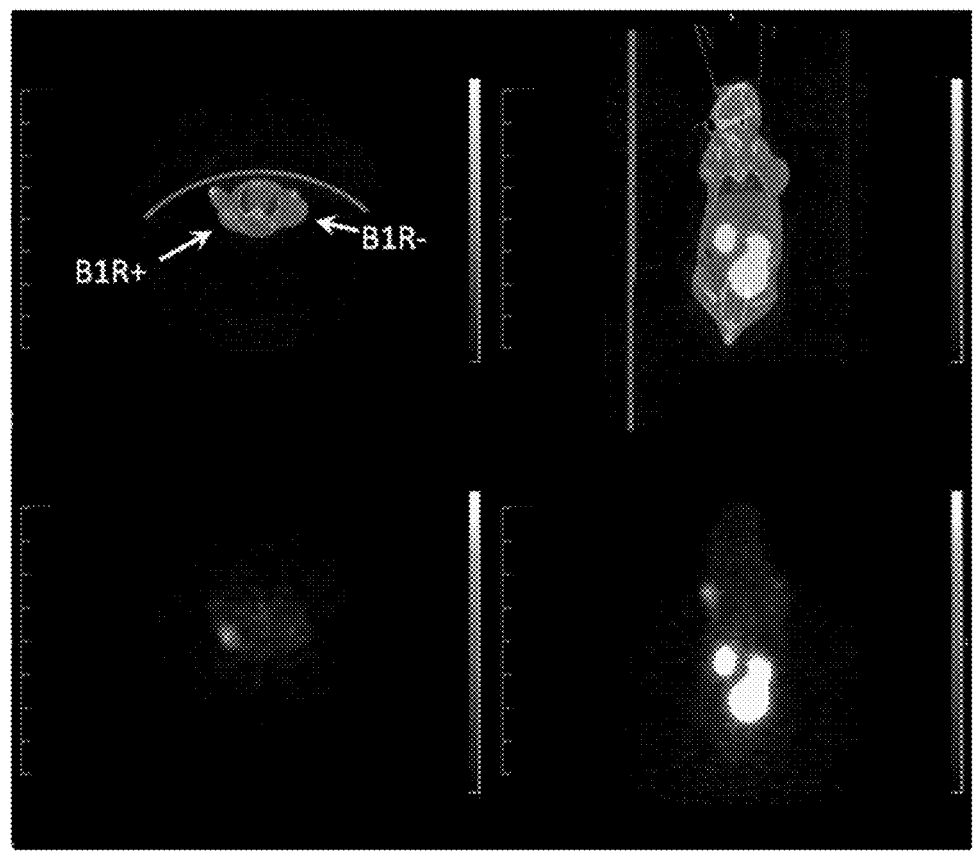
FIG. 5 presents reconstructed Ga-68 Peptide 3 images (1 h post-injection) of SCID IL2R KO mouse bearing tumours derived from HEK293T::GFP (B1R−) and HEK293T::hB1R (B1R+) cells.

FIG. 5 shows the results for Peptide 3: $^{68}$Ga-DOTA-PEG2-Lys-Arg-Pro-Hyp-Gly-Cha-Ser-Pro-Leu [SEQ ID NO:10]

The image represents a mouse with a bradykinin receptor expressing (B1R+) tumour with a comparable negative control (B1R−; arrowed), showing specific receptor-mediated uptake in the B1R and no uptake of the radio-labelled compound in the negative control. There is very low background activity with the exception of renal and bladder clearance of the radio-labelled compound.

Figure 6:
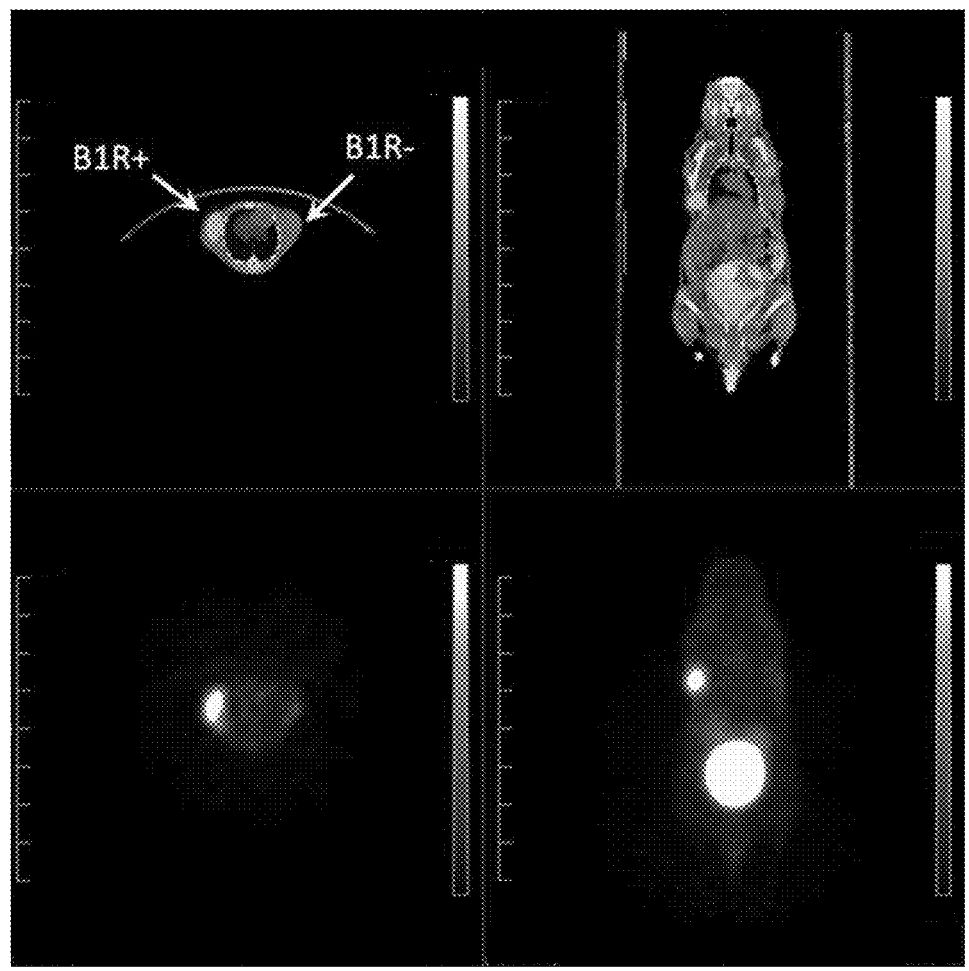
FIG. 6 presents reconstructed Ga-68 Peptide 8 images (1 h post-injection) of SCID IL2R KO mouse bearing tumours derived from HEK293T::GFP (B1R−) and HEK293T::hB1R (B1R+) cells.

FIG. 6 shows the results for Peptide 8: $^{68}$Ga-DOTA-Gly-Gly-Lys-Arg-Pro-Hyp-Gly-Cha-Ser-Pro-Leu [SEQ ID NO:29]

This image demonstrates that substituting the PEG2 linker in Peptide 3 with two glycine amino acids also led to good visualization of B1R+ expressing cells, with essentially negligible non-specific uptake in the control tumour. Clearance remained predominantly via the kidneys and bladder.

Figure 7:
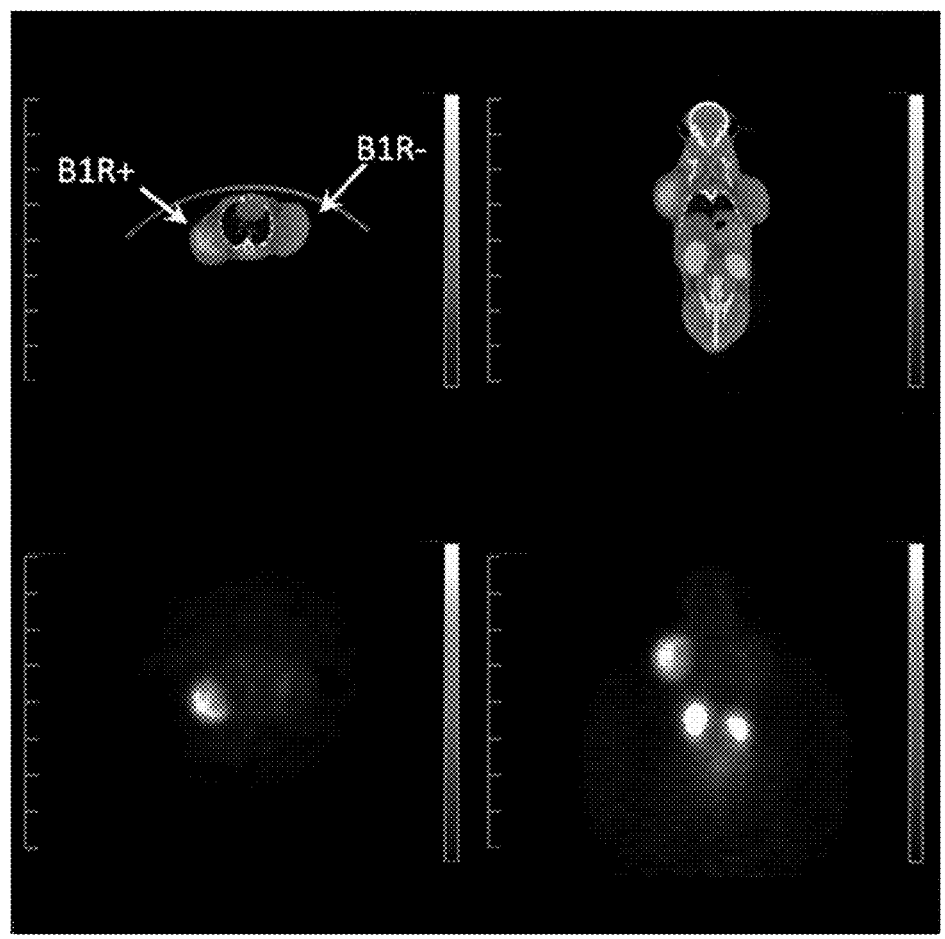
FIG. 7 presents reconstructed Ga-68 Peptide 10 images (1 h post-injection) of SCID IL2R KO mouse bearing tumours derived from HEK293T::GFP (B1R−) and HEK293T::hB1R (B1R+) cells.

FIG. 7 shows the results from Peptide 10: $^{68}$Ga-DOTA-Ahx-Lys-Arg-Pro-Hyp-Gly-Cha-Ser-Pro-Leu [SEQ ID NO:36]

This image demonstrates that by substituting the PEG2 linker of Peptide 3 with an aminohexanoic linker, excellent visualization of B1R+ cells was also obtained, with lower background uptake. This result also demonstrates that replacing key amino acid residues of Peptide 4 with non-naturally occurring amino acids provided much greater in vivo stability to the peptide, resulting in higher uptake in the B1R+ tumour (compare to Example 5).

Figure 8:
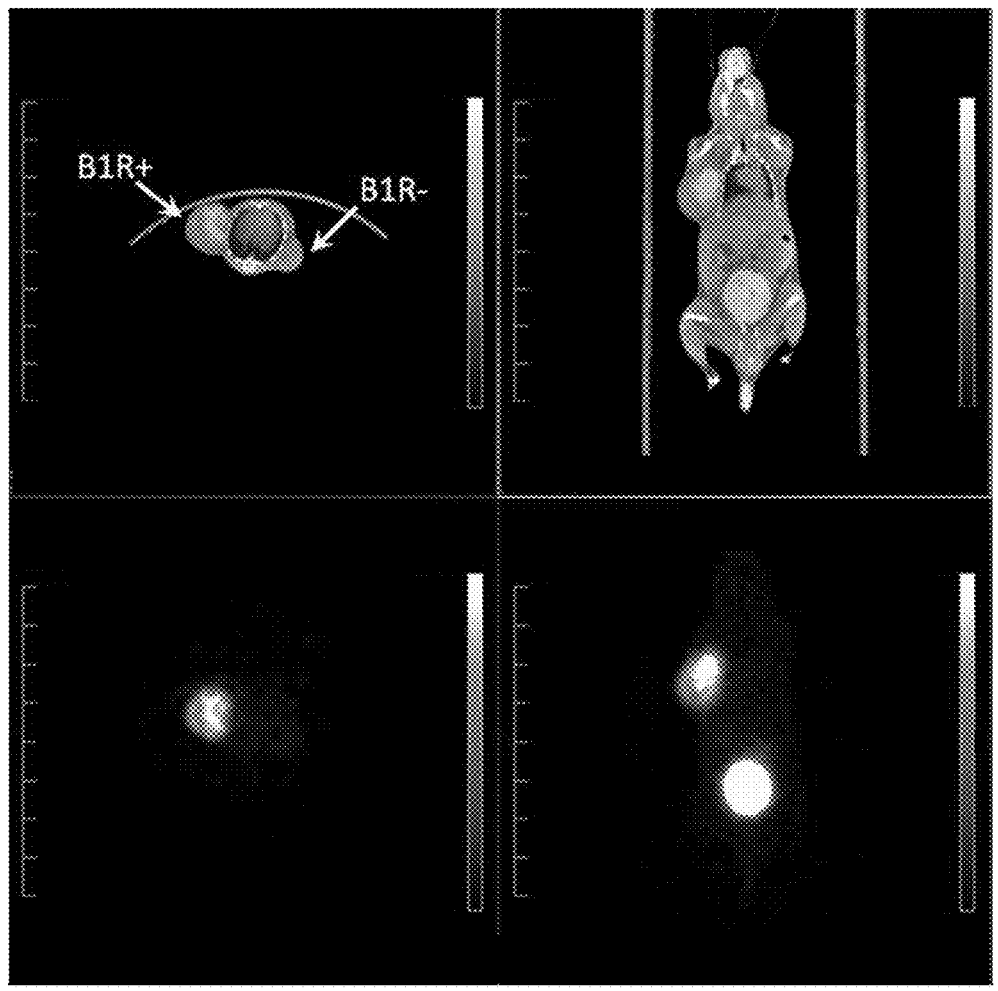
FIG. 8 presents reconstructed Ga-68 Peptide 12 images (1 h post-injection) of SCID IL2R KO mouse bearing tumours derived from HEK293T::GFP (B1R−) and HEK293T::hB1R (B1R+) cells.

FIG. 8 shows the results with Peptide 12: $^{68}$Ga-DOTA-Ahx-Lys-Arg-Pro-Hyp-Gly-Cha-Ser-Pro-(D-Phe) [SEQ ID NO:34]

Peptide 12 is an agonist version of Peptide 3 that was developed by substituting the C-terminal Leu residue with a D-Phe residue. Slightly higher tumour uptake of Peptide 12 was obtained, also with minimal background activity, no non-specific tumour uptake, and good clearance through the kidneys and bladder. Biodistribution data for Peptide 12 is provided in Table 7 below.

TABLE 7

Biodistribution of Ga-68 Peptide 12 in SCID IL2R KO tumour-bearing mice at 1 h post-injection

| Organ | Average | St. Dev |
|---|---|---|
| Blood | 0.039 | 0.002 |
| Plasma | 0.473 | 0.021 |
| Fat | 0.039 | 0.011 |
| Seminal glands | 0.230 | 0.255 |
| Testes | 0.132 | 0.001 |
| Large intestine | 0.149 | 0.045 |
| Small intestine | 0.208 | 0.025 |
| Spleen | 0.127 | 0.090 |
| Liver | 0.129 | 0.019 |
| Pancreas | 0.069 | 0.013 |
| Adrenal glands | 0.001 | 0.000 |
| Kidney | 6.436 | 0.732 |
| Lungs | 0.800 | 0.330 |
| Heart | 0.150 | 0.014 |
| Left tumour | 0.194 | 0.015 |
| Right tumour | 7.909 | 2.428 |
| Skin | 0.223 | 0.027 |
| Muscle | 0.056 | 0.003 |
| Bone | 0.093 | 0.032 |
| Brain | 0.009 | 0.004 |
| Tail | 0.226 | 0.015 |

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A bradykinin B1 receptor (B1R) targeting compound that selectively binds to B1R, comprising: a peptidic compound having general Formula (I) or a non-peptidic compound having general Formula (III):

B-L-Xaa¹-Xaa²-Arg-Pro-Xaa³-Gly-Xaa⁴-Ser-Xaa⁵-Xaa⁶ (I)

wherein:
B is a radio-labelled moiety, radiometal chelating agent, N-succinimidyl-4-[$^{18}$F]fluorobenzoate (SFB), D-Pra,

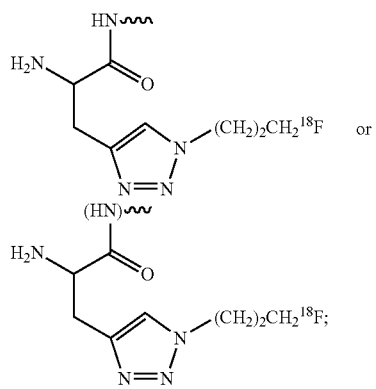

L is a linker;
Xaa¹ is Lys or Sar;
Xaa² is Lys or D-Arg;
Xaa³ is Pro or Hyp;
Xaa⁴ is Phe, Cha, Thi, (α-Me)Phe, Igl or Cpg;
Xaa⁵ is Pro, D-Tic, D-Hyp, D-βNal or D-Igl, and
Xaa⁶ is Leu, Ile, D-Phe, Cpg or Oic [SEQ ID NO: 31], wherein Xaa⁶ is not peptide-bonded to Arg, and
wherein when B is a radiometal chelating agent, it is optionally chelated to a radiolabel;

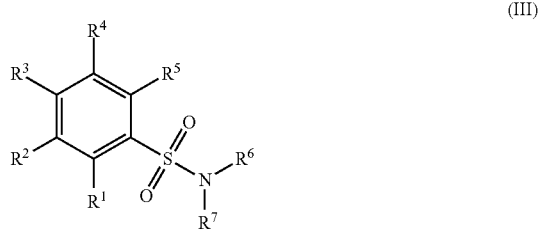

wherein:
R¹, R⁴ and R⁵ are each independently H or Me;
R² is H or halo;
R³ is H, Me, halo or OMe;
~NR⁶R⁷ is:

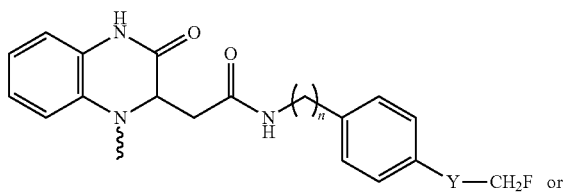

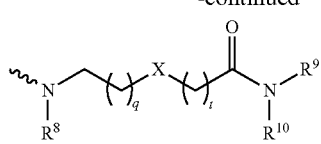

Y is (CH$_2$)$_m$NHR or

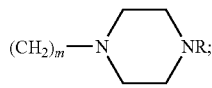

R is (CH$_2$)$_p$;
R⁸ is Me or Et;
X is O or CH$_2$;
NR⁹R¹⁰ is

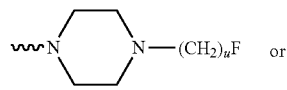

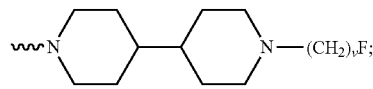

n, m, p, q and t are each independently 0, 1 or 2, and
u and v are each independently 1 or 2, and
wherein F is optionally $^{18}$F.

2. The B1R targeting compound, according to claim 1, wherein the B1R targeting compound has general formula (I).

3. The B1R targeting compound, according to claim 2, wherein the radiometal chelating agent is selected from the group consisting of: DTPA, DOTA, NOTA, NODAGA, TE2A, PCTA, DO3A, DEDPA and TETA.

4. The B1R targeting compound, according to claim 2, wherein the linker is selected from the group consisting of: Abu, Aba, Aib, 5-Ava, Ahx, 7-aminoheptanoic acid, 8-Aoc, 9-aminononanoic acid, 10-aminodecanoic acid, 11-Aun, a glycine linker, mini-PEG, mini-PEG3, PEG2 and PEG4.

5. The B1R targeting compound according to claim 2, wherein B is DTPA, DOTA or NOTA chelated to a radiolabel selected from the group consisting of: $^{99m}$T, $^{111}$In, $^{68}$Ga, $^{66}$Ga, $^{64}$Cu, $^{67}$Cu, $^{90}$Y, $^{213}$Bi, $^{177}$Lu, Al—$^{18}$F, $^{186}$Re, $^{188}$Re and $^{44}$Sc.

6. The B1R targeting compound, according to claim 1, wherein the B1R targeting compound has general formula (III).

7. The B1R targeting compound according to claim 6, wherein the B1R targeting compound has general formula (VI):

(VI)

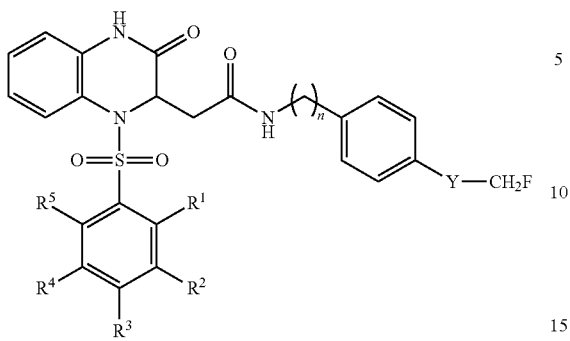

wherein:
$R^1$, $R^4$ and $R^5$ are each independently H or Me;
$R^2$ is H or halo;
$R^3$ is H, Me, halo or OMe;
Y is $(CH_2)_m NHR$ or

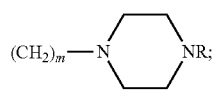

R is $(CH_2)_p$;
n, m and p are each independently 0, 1 or 2, and
wherein F is optionally $^{18}F$.

8. The B1R targeting compound according to claim 6, wherein the B1R targeting compound has general formula (VII):

(VII)

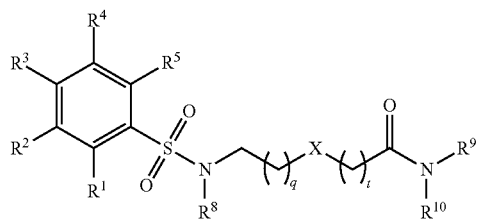

wherein:
$R^1$, $R^4$ and $R^5$ are each independently H or Me;
$R^2$ is H or halo;
$R^3$ is H, Me, halo or OMe;
$R^8$ is Me or Et;
X is O or $CH_2$;
~$NR^9R^{10}$ is

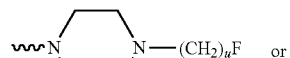

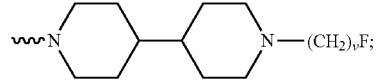

q and t are each independently 0, 1 or 2;
u and v are each independently 1 or 2;
wherein F is optionally $^{18}F$.

9. The B1R targeting compound according to claim 7 which is selected from the group consisting of:

5

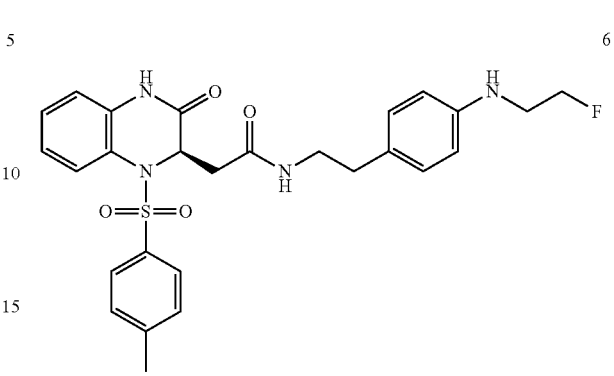

6

7

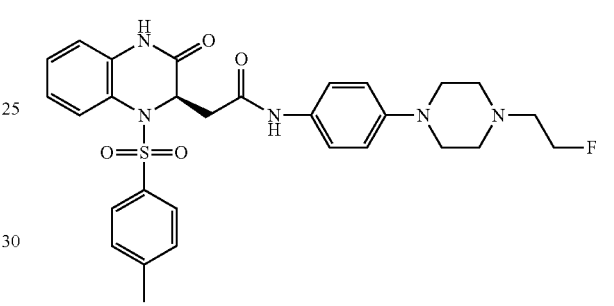

8

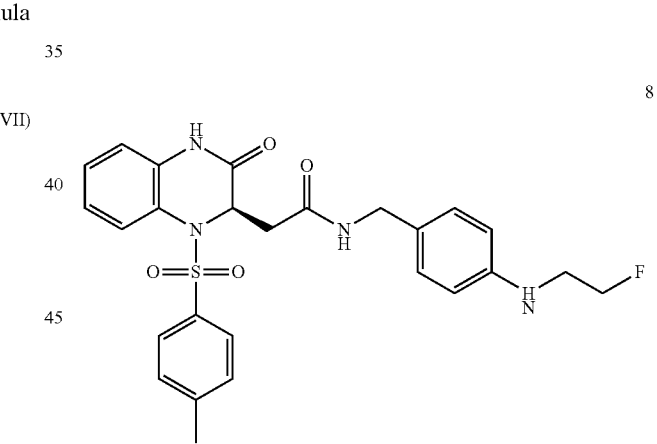

6a

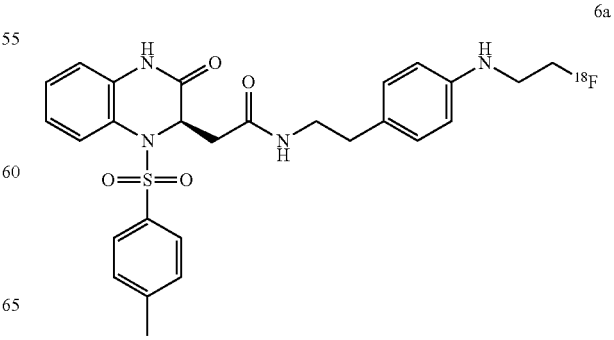

-continued
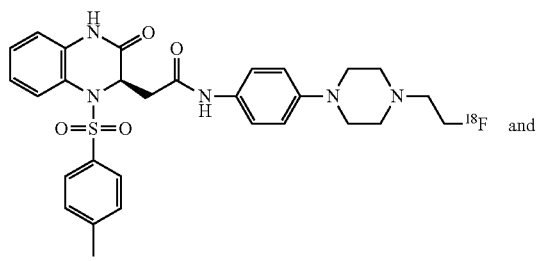
7a
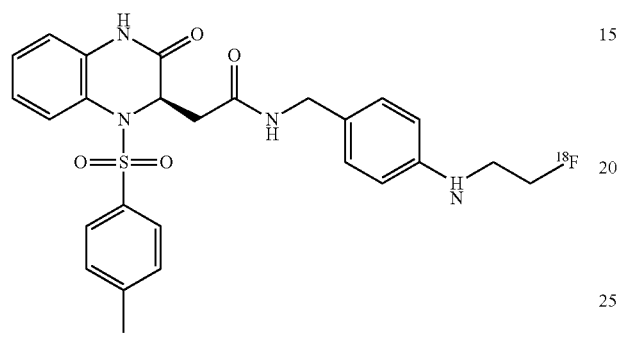
8a
10. The B1R targeting compound according to claim 8 which is:
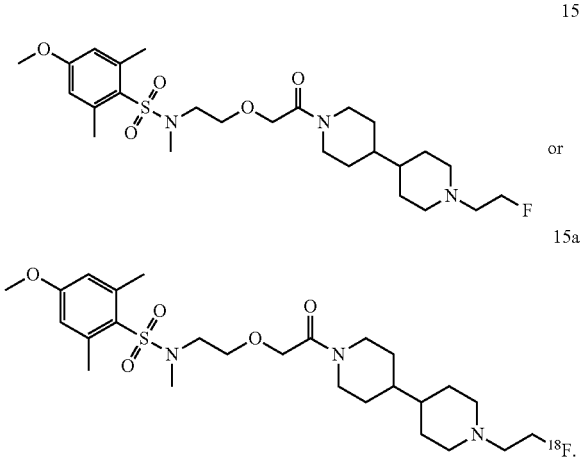
11. The B1R targeting compound according to claim 2, wherein Xaa$^1$ is Lys, Xaa$^2$ is Lys, Xaa$^3$ is Hyp, Xaa$^4$ is Cpg, Xaa$^5$ is D-Tic and Xaa$^6$ is Cpg [SEQ ID NO:17].
* * * * *